US012708429B2

(12) United States Patent
Shelton, IV et al.

(10) Patent No.: US 12,708,429 B2
(45) Date of Patent: Aug. 18, 2026

(54) SURGICAL DEVICES, SYSTEMS, AND METHODS FOR CONTROL OF ONE VISUALIZATION WITH ANOTHER

(71) Applicant: Cilag GmbH International, Zug (CH)

(72) Inventors: Frederick E. Shelton, IV, Hillsboro, OH (US); Jason L. Harris, Lebanon, OH (US); Daniel J. Mumaw, Cincinnati, OH (US); Shane R. Adams, Lebanon, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 331 days.

(21) Appl. No.: 17/494,438

(22) Filed: Oct. 5, 2021

(65) Prior Publication Data

US 2023/0101639 A1 Mar. 30, 2023

Related U.S. Application Data

(60) Provisional application No. 63/249,658, filed on Sep. 29, 2021.

(51) Int. Cl.
*A61B 18/14* (2006.01)
*A61B 1/00* (2006.01)
(Continued)

(52) U.S. Cl.
CPC ...... *A61B 18/1482* (2013.01); *A61B 1/00148* (2022.02); *A61B 1/045* (2013.01);
(Continued)

(58) Field of Classification Search
CPC ..... A61B 18/1482; A61B 18/00; A61B 18/14; A61B 18/1442; A61B 18/1445;
(Continued)

(56) References Cited

U.S. PATENT DOCUMENTS 5,188,104 A 2/1993 Wernicke et al.
5,231,988 A 8/1993 Wernicke et al.
(Continued)

FOREIGN PATENT DOCUMENTS

CN 113384343 A 9/2021
EP 1719471 A2 11/2006
(Continued)

OTHER PUBLICATIONS

"Fiber Bragg Gatings," RP Photonics Encyclopedia, available at <https://www.rp-photonics.com/fiber_bragg_gratings.html>, dated no later than Apr. 5, 2021 (12 pages).
(Continued)

*Primary Examiner* — Sean D Mattson
(74) *Attorney, Agent, or Firm* — Condo Roccia Koptiw LLP

(57) ABSTRACT

In general, devices, systems, and methods for control of one visualization with another are provided. In one aspect, a surgical system is provided that in one embodiment includes a first surgical device, an imaging device, and a controller. The first surgical device includes a distal portion configured to be advanced into a patient's first anatomic space, and includes a plurality of electrodes configured to delivery energy to tissue. The imaging device includes a distal portion configured to be advanced into a second, different anatomic space of the patent and, with the electrodes delivering the energy to the tissue and with the imaging device's image sensor located in the second anatomic space, gather images using the image sensor. The controller is configured to, with the electrodes delivering the energy to the tissue, control location and movement of the electrodes.

20 Claims, 37 Drawing Sheets

(51) Int. Cl.

| | |
|---|---|
| ***A61B 1/045*** | (2006.01) |
| ***A61B 1/273*** | (2006.01) |
| ***A61B 1/313*** | (2006.01) |
| ***A61B 18/00*** | (2006.01) |
| ***A61B 34/20*** | (2016.01) |
| ***A61B 34/30*** | (2016.01) |
| ***A61N 1/05*** | (2006.01) |
| *A61B 1/05* | (2006.01) |
| *A61B 17/00* | (2006.01) |
| *A61B 18/12* | (2006.01) |
| *A61B 34/00* | (2016.01) |

(52) U.S. Cl.

CPC ............ *A61B 1/273* (2013.01); *A61B 1/3132* (2013.01); *A61B 18/00* (2013.01); *A61B 18/14* (2013.01); *A61B 18/1442* (2013.01); *A61B 34/20* (2016.02); *A61B 34/30* (2016.02); *A61N 1/0509* (2013.01); *A61B 1/00027* (2013.01); *A61B 1/00045* (2013.01); *A61B 1/00057* (2013.01); *A61B 1/05* (2013.01); *A61B 2017/00017* (2013.01); *A61B 2017/00022* (2013.01); *A61B 2017/00026* (2013.01); *A61B 2018/00071* (2013.01); *A61B 2018/0016* (2013.01); *A61B 2018/0022* (2013.01); *A61B 2018/00494* (2013.01); *A61B 2018/00577* (2013.01); *A61B 2018/00595* (2013.01); *A61B 2018/00601* (2013.01); *A61B 2018/0063* (2013.01); *A61B 2018/00696* (2013.01); *A61B 2018/00702* (2013.01); *A61B 2018/00732* (2013.01); *A61B 2018/00767* (2013.01); *A61B 2018/00779* (2013.01); *A61B 2018/00791* (2013.01); *A61B 2018/00845* (2013.01); *A61B 2018/00875* (2013.01); *A61B 2018/00916* (2013.01); *A61B 18/1206* (2013.01); *A61B 2018/1467* (2013.01); *A61B 2034/2057* (2016.02); *A61B 34/70* (2016.02); *A61B 2218/002* (2013.01)

(58) Field of Classification Search

CPC . A61B 18/1492; A61B 1/00148; A61B 1/045; A61B 1/273; A61B 1/3132; A61B 34/20; A61B 34/30; A61B 34/37; A61B 2018/0016; A61B 2018/0022; A61B 2018/00494; A61B 2018/00577; A61B 2018/00595; A61B 2018/00601; A61B 2018/0063; A61B 2018/00696; A61B 2018/00702; A61B 2018/00732; A61B 2018/00767; A61B 2018/00791; A61B 2018/00845; A61B 2018/00875; A61B 2018/1467; A61B 2018/00267; A61B 2018/00291; A61B 2018/00482; A61B 2018/00541; A61B 2018/00654; A61B 2018/00678; A61B 2018/00708; A61B 2018/00744; A61B 2018/1475; A61B 2018/00023; A61B 2034/2057; A61B 2034/105; A61B 2034/302; A61B 2218/002; A61B 17/07292; A61B 2017/00026; A61B 2090/061; A61B 2090/065; A61B 2090/3784; A61B 2090/3954; A61B 90/361; A61N 1/0509; A61N 1/3605; A61N 1/3606

See application file for complete search history.

(56) References Cited

U.S. PATENT DOCUMENTS

| | | | | |
|---|---|---|---|---|
| 5,256,149 | A | 10/1993 | Banik et al. | |
| 5,263,480 | A | 11/1993 | Wernicke et al. | |
| 5,540,730 | A | 7/1996 | Terry, Jr. et al. | |
| 5,558,671 | A | 9/1996 | Yates | |
| 6,086,528 | A | 7/2000 | Adair | |
| 6,740,082 | B2 | 5/2004 | Shadduck | |
| 7,143,925 | B2 | 12/2006 | Shelton, IV et al. | |
| 7,585,290 | B2 | 9/2009 | Kathrani et al. | |
| 7,601,118 | B2 | 10/2009 | Smith et al. | |
| 8,068,649 | B2 | 11/2011 | Green | |
| 8,317,070 | B2 | 11/2012 | Hueil et al. | |
| 8,352,026 | B2 | 1/2013 | DiUbaldi | |
| 8,393,514 | B2 | 3/2013 | Shelton, IV et al. | |
| 8,517,933 | B2 | 8/2013 | Mohr | |
| 8,521,291 | B1 | 8/2013 | Cholette et al. | |
| 8,545,515 | B2 | 10/2013 | Prisco et al. | |
| 8,551,115 | B2 | 10/2013 | Steger et al. | |
| 8,623,028 | B2 | 1/2014 | Rogers et al. | |
| 8,632,462 | B2 | 1/2014 | Yoo et al. | |
| 8,636,751 | B2 | 1/2014 | Albrecht et al. | |
| 8,656,144 | B2 | 2/2014 | Kang | |
| 8,734,478 | B2 | 5/2014 | Widenhouse et al. | |
| 8,753,338 | B2 | 6/2014 | Widenhouse et al. | |
| 8,771,180 | B2 | 7/2014 | Mohr | |
| 8,812,100 | B2 | 8/2014 | Voegele et al. | |
| 8,831,782 | B2 | 9/2014 | Itkowitz | |
| 8,888,789 | B2 | 11/2014 | Prisco et al. | |
| 8,919,348 | B2 | 12/2014 | Williams et al. | |
| 8,961,406 | B2 | 2/2015 | Ortiz et al. | |
| 9,044,606 | B2 | 6/2015 | Harris et al. | |
| 9,072,535 | B2 | 7/2015 | Shelton, IV et al. | |
| 9,072,536 | B2 | 7/2015 | Shelton, IV et al. | |
| 9,204,879 | B2 | 12/2015 | Shelton, IV | |
| 9,216,062 | B2 | 12/2015 | Duque et al. | |
| 9,254,178 | B2 | 2/2016 | Prisco et al. | |
| 9,274,047 | B2 | 3/2016 | Velten et al. | |
| 9,283,050 | B2 | 3/2016 | Prisco et al. | |
| 9,320,416 | B2 | 4/2016 | Cooper et al. | |
| 9,339,341 | B2 | 5/2016 | Cooper | |
| 9,358,074 | B2 | 6/2016 | Schena et al. | |
| 9,393,017 | B2 | 7/2016 | Flanagan et al. | |
| 9,561,038 | B2 | 2/2017 | Shelton, IV et al. | |
| 9,572,481 | B2 | 2/2017 | Duindam et al. | |
| 9,636,186 | B2 | 5/2017 | Kumar et al. | |
| 9,757,128 | B2 | 9/2017 | Baber et al. | |
| 9,962,161 | B2 | 5/2018 | Scheib et al. | |
| 10,092,738 | B2 | 10/2018 | Harris et al. | |
| 10,179,024 | B2 | 1/2019 | Yeung | |
| 10,206,682 | B2 | 2/2019 | Bakos et al. | |
| 10,245,069 | B2 | 4/2019 | Rogers et al. | |
| 10,492,788 | B2 | 12/2019 | Swayze et al. | |
| 10,517,600 | B2 | 12/2019 | Beisel et al. | |
| 10,569,071 | B2 | 2/2020 | Harris et al. | |
| 10,716,564 | B2 | 7/2020 | Shelton, IV et al. | |
| 10,751,117 | B2 | 8/2020 | Witt et al. | |
| 10,779,831 | B2 | 9/2020 | Lukin et al. | |
| 10,792,034 | B2 | 10/2020 | Scheib et al. | |
| 10,856,928 | B2 | 12/2020 | Shelton, IV et al. | |
| 10,925,598 | B2 | 2/2021 | Scheib et al. | |
| 11,033,272 | B2 | 6/2021 | Fegelman et al. | |
| 11,051,876 | B2 | 7/2021 | Shelton, IV et al. | |
| 2005/0277998 | A1 | 12/2005 | Tracey et al. | |
| 2006/0106375 | A1* | 5/2006 | Werneth ............ | A61B 18/1492 606/41 |
| 2006/0195146 | A1 | 8/2006 | Tracey et al. | |
| 2006/0195153 | A1 | 8/2006 | DiUbaldi et al. | |
| 2007/0043338 | A1 | 2/2007 | Moll et al. | |
| 2007/0185541 | A1 | 8/2007 | DiUbaldi et al. | |
| 2007/0208339 | A1 | 9/2007 | Arts et al. | |
| 2007/0265598 | A1 | 11/2007 | Karasik | |
| 2008/0132962 | A1 | 6/2008 | DiUbaldi et al. | |
| 2008/0147146 | A1 | 6/2008 | Wahlgren et al. | |
| 2008/0312652 | A1 | 12/2008 | Bell et al. | |
| 2009/0062792 | A1 | 3/2009 | Vakharia et al. | |
| 2009/0132018 | A1 | 5/2009 | DiUbaldi et al. | |

(56) References Cited

U.S. PATENT DOCUMENTS

2009/0149918 A1 6/2009 Krulevitch et al.
2009/0157149 A1 6/2009 Wahlgren et al.
2010/0036378 A1* 2/2010 Savery .............. A61B 18/1206 606/42
2010/0161001 A1 6/2010 DiUbaldi et al.
2010/0161005 A1 6/2010 Wahlgren et al.
2010/0168624 A1* 7/2010 Sliwa ...................... A61B 7/00 601/3
2010/0191267 A1 7/2010 Fox
2010/0239648 A1 9/2010 Smith et al.
2011/0094773 A1 4/2011 Bare et al.
2011/0118708 A1 5/2011 Burbank et al.
2011/0251607 A1* 10/2011 Kruecker ........... A61B 18/1815 600/407
2011/0288544 A1* 11/2011 Verin ................ A61B 18/1492 606/41
2012/0083780 A1 4/2012 Shadduck
2012/0099974 A1 4/2012 Wolf
2012/0150192 A1 6/2012 Dachs, II et al.
2012/0197061 A1* 8/2012 Requarth ............ A61B 17/1114 600/12
2012/0209314 A1 8/2012 Weir et al.
2013/0096549 A1* 4/2013 Organ ................ A61B 18/1206 606/41
2013/0105545 A1 5/2013 Burbank
2013/0105552 A1 5/2013 Weir et al.
2013/0146643 A1 6/2013 Schmid et al.
2013/0221065 A1 8/2013 Aronhalt et al.
2013/0256377 A1 10/2013 Schmid et al.
2013/0261368 A1 10/2013 Schwartz
2013/0345670 A1* 12/2013 Rajagopalan ........ A61B 18/042 606/1
2014/0066717 A1 3/2014 Rogers et al.
2014/0121678 A1 5/2014 Trusty et al.
2015/0016700 A1 1/2015 Drozdzal et al.
2015/0057570 A1* 2/2015 Chin ...................... A61B 90/11 606/46
2015/0105773 A1 4/2015 Weber et al.
2015/0129634 A1 5/2015 Shelton, IV et al.
2015/0133995 A1 5/2015 Shelton, IV et al.
2015/0133996 A1 5/2015 Shelton, IV et al.
2015/0134076 A1 5/2015 Shelton, IV et al.
2015/0134077 A1 5/2015 Shelton, IV et al.
2015/0141987 A1* 5/2015 Caplan ................... A61B 18/14 606/41
2015/0150466 A1 6/2015 Abi-jaoudeh et al.
2015/0164357 A1 6/2015 Zeng et al.
2015/0238268 A1 8/2015 Weir et al.
2015/0257841 A1 9/2015 Dachs, II
2015/0257842 A1 9/2015 Dachs, II
2015/0272575 A1 10/2015 Leimbach et al.
2015/0351758 A1 12/2015 Shelton, IV et al.
2015/0359594 A1 12/2015 Ben-oren et al.
2016/0015259 A1 1/2016 Mody et al.
2016/0030108 A1* 2/2016 Lupotti ................ A61B 5/0066 600/407
2016/0228175 A1 8/2016 Sliwa
2016/0256071 A1 9/2016 Shelton, IV et al.
2016/0262761 A1 9/2016 Beisel et al.
2016/0303743 A1 10/2016 Rockrohr
2016/0331473 A1 11/2016 Yamamura
2017/0035425 A1 2/2017 Fegelman et al.
2017/0055819 A1 3/2017 Hansen et al.
2017/0055986 A1 3/2017 Harris et al.
2017/0071693 A1 3/2017 Taylor et al.
2017/0128041 A1 5/2017 Hasser et al.
2017/0128144 A1 5/2017 Hasser et al.
2017/0128145 A1 5/2017 Hasser et al.
2017/0202591 A1 7/2017 Shelton, IV et al.
2017/0251900 A1 9/2017 Hansen et al.
2017/0265866 A1 9/2017 Ryou et al.
2017/0340383 A1 11/2017 Bloom et al.
2018/0049820 A1 2/2018 Widenhouse et al.
2018/0177556 A1 6/2018 Noonan
2018/0228537 A1 8/2018 Dong et al.
2018/0256208 A1 9/2018 Altschul et al.
2018/0271577 A1* 9/2018 Bharat .................. A61B 34/10
2018/0353174 A1 12/2018 Widenhouse et al.
2019/0059980 A1 2/2019 Shelton, IV et al.
2019/0099209 A1 4/2019 Witt et al.
2019/0125431 A1 5/2019 Shelton, IV et al.
2019/0125455 A1* 5/2019 Shelton, IV ......... A61B 17/072
2019/0200844 A1 7/2019 Shelton, IV et al.
2019/0200905 A1 7/2019 Shelton, IV et al.
2019/0200981 A1 7/2019 Harris et al.
2019/0201046 A1 7/2019 Shelton, IV et al.
2019/0201088 A1 7/2019 Shelton, IV et al.
2019/0201114 A1 7/2019 Shelton, IV et al.
2019/0201136 A1 7/2019 Shelton, IV et al.
2019/0201140 A1 7/2019 Yates et al.
2019/0204201 A1 7/2019 Shelton, IV et al.
2019/0206004 A1 7/2019 Shelton, IV et al.
2019/0206050 A1 7/2019 Yates et al.
2019/0206555 A1 7/2019 Morgan et al.
2019/0207857 A1 7/2019 Shelton, IV et al.
2019/0262074 A1* 8/2019 Kusumoto ........... A61B 5/0035
2020/0000530 A1 1/2020 DeFonzo et al.
2020/0015668 A1 1/2020 Scheib
2020/0015897 A1 1/2020 Scheib et al.
2020/0015898 A1 1/2020 Scheib et al.
2020/0015899 A1 1/2020 Scheib et al.
2020/0015900 A1 1/2020 Scheib et al.
2020/0015901 A1 1/2020 Scheib et al.
2020/0015902 A1 1/2020 Scheib et al.
2020/0015903 A1 1/2020 Scheib et al.
2020/0015906 A1 1/2020 Scheib et al.
2020/0015907 A1 1/2020 Scheib
2020/0015914 A1 1/2020 Scheib et al.
2020/0015923 A1 1/2020 Scheib et al.
2020/0015924 A1 1/2020 Scheib et al.
2020/0015925 A1 1/2020 Scheib
2020/0069192 A1 3/2020 Sanborn et al.
2020/0078109 A1 3/2020 Steger et al.
2020/0085516 A1 3/2020 DeFonzo et al.
2020/0170720 A1 6/2020 Ummalaneni
2020/0188043 A1 6/2020 Yu et al.
2020/0188046 A1 6/2020 Overmyer et al.
2020/0214709 A1 7/2020 Motai
2020/0289223 A1* 9/2020 Denlinger .............. A61B 34/77
2020/0315723 A1 10/2020 Hassan et al.
2020/0405417 A1 12/2020 Shelton, IV et al.
2021/0068895 A1 3/2021 Panescu et al.
2021/0196108 A1 7/2021 Shelton, IV
2021/0196109 A1 7/2021 Shelton, IV et al.
2021/0196381 A1 7/2021 Eckert et al.
2021/0196383 A1 7/2021 Shelton, IV et al.
2021/0196384 A1 7/2021 Shelton, IV et al.
2021/0196385 A1 7/2021 Shelton, IV et al.
2021/0196386 A1 7/2021 Shelton, IV et al.
2021/0196423 A1 7/2021 Shelton, IV et al.
2021/0196424 A1 7/2021 Shelton, IV et al.
2021/0196425 A1 7/2021 Shelton, IV et al.
2021/0199557 A1 7/2021 Shelton, IV et al.
2021/0212792 A1 7/2021 Shelton, IV et al.
2022/0184339 A1 6/2022 Rajagopalan et al.
2023/0093944 A1 3/2023 Maples et al.
2023/0094434 A1 3/2023 Shelton, IV et al.
2023/0095790 A1 3/2023 Shelton, IV et al.
2023/0099253 A1 3/2023 Shelton, IV et al.
2023/0101750 A1 3/2023 Shelton, IV et al.
2023/0103875 A1 4/2023 Shelton, IV et al.
2023/0312700 A1 10/2023 Jones et al.

FOREIGN PATENT DOCUMENTS

EP 1829494 A1 9/2007
EP 1824405 B1 1/2011
EP 1886711 B1 4/2018
EP 3714826 A1 9/2020
EP 3750500 A1 12/2020
EP 3845193 A1 7/2021
JP 2012-099974 A 5/2012
WO WO-2010007600 A1 1/2010

(56) References Cited

FOREIGN PATENT DOCUMENTS

| | | | |
|---|---|---|---|
| WO | WO-2011143468 | A2 | 11/2011 |
| WO | WO-2012007052 | A1 | 1/2012 |
| WO | WO-2013143608 | A1 | 10/2013 |
| WO | WO-2014026055 | A1 | 2/2014 |
| WO | WO-2014118738 | A1 | 8/2014 |
| WO | WO-2014151621 | A1 | 9/2014 |
| WO | WO-2015142814 | A1 | 9/2015 |
| WO | WO-2015153636 | A1 | 10/2015 |
| WO | WO-2015153642 | A1 | 10/2015 |
| WO | WO-2016144937 | A1 | 9/2016 |
| WO | WO-2016144998 | A1 | 9/2016 |
| WO | WO-2016183054 | A1 | 11/2016 |
| WO | WO-2016205266 | A1 | 12/2016 |
| WO | WO-2016205452 | A1 | 12/2016 |
| WO | WO-2016209769 | A1 | 12/2016 |
| WO | WO-2017044406 | A1 | 3/2017 |
| WO | WO-2017053358 | A1 | 3/2017 |
| WO | WO-2017053363 | A1 | 3/2017 |
| WO | WO-2017053507 | A1 | 3/2017 |
| WO | WO-2017053698 | A1 | 3/2017 |
| WO | WO-2017075121 | A1 | 5/2017 |
| WO | WO-2017116793 | A1 | 7/2017 |
| WO | WO-2019164842 | A1 | 8/2019 |
| WO | WO-2019168816 | A1 | 9/2019 |
| WO | WO-2020260999 | A1 | 12/2020 |
| WO | WO-2021168061 | A1 | 8/2021 |

OTHER PUBLICATIONS

"Ion by Intuitive," available at <https://www.intuitive.com/en-us/products-and-services/ion>, dated no later than Apr. 5, 2021 (5 pages).

Aisu et al., Laparoscopic and endoscopic cooperative surgery for gastric tumors: Perspective for actual practice and oncological benefits,: World J Gastrointest Oncol, Nov. 15, 2018, 10(11): 381-397.

Akirov, "Duodenal Mucosal Resurfacing May Safely Improve Glycemic Control in T2D," Aug. 19, 2019, Haymarket Media, Inc., 14 pages.

Brace et al., "Thermal Tumor Ablation in Clinical Use," IEEE Pulse, 2011, 2(5):28-38.

Carlota V., "4D printing reconfigurable materials for use in aerospace, medical and robotics fields," Apr. 3, 2019, available at <https://www.3dnatices.com/en/4d-printing-materials-030420195/> (7 pages).

Chauhan et al., "Enteroscopy," Gastrointestinal Endoscopy, 2015, vol. 82, No. 6, 975-990.

Conway et al., "Endoscopic hemostatic devices," Gastrointestinal Endoscopy, 2009, vol. 69, No. 6, 987-996.

Dunkin et al., "Thin-layer ablation of human esophagael epithelium using a bipolar radiofrequency balloon device," Surg Endosc (2006) 20: 125-130.

Ethicon, "Laparoscopic Sizing Tool: LINX® Reflux Management System," 2019 (6 pages).

Fried et al., "A novel approach to glycemic control in type 2 diabetes mellius, partial jejunal diversion: pre-clinical to clinical pathway," BMJ Open Diab Res Care 2017; 5:e000431.doi:10.1136*BMJdrc-2017000431.

Garvey, "Ablation of the Duodenal Mucosa as a Strategy for Glycemic Control in Diabetes: Role of Nutrient Signaling or Simple Weight Loss," Diabetes Care 2016; 39:2108-2110.

Gioux et al., "Image-Guided Surgery using Invisible Near-Infrared Light: Fundamental of Clinical Translation," Mol Imaging, Oct. 2010, 9)5): 237-255.

Gupta, "Understanding Image Recognition and Its Uses," eInfochips, available at <http://www.einfochips.com/blog/understanding-image-recognition-and-its-uses/>, Dec. 11, 2019.

Hiki et al., "Laparoscopic and endoscopic cooperative surgery for gastrointestinal stromal tumor dissection," Surg Endosc (2008) 22:1729-1735.

Intuitive Surgical, "Da Vinci Xi Single-Site Technology: Solutions For Single-Incision Surgery," 2016 (10 pages).

Kurata et al., "Time-Of-Flight Near-Infrared Spectroscopy For Nondestructive Measurement Of Internal Quality In Grapefruit," Journal of the American Society for Horticultural Science, May 2013 vol. 138 No. 3 225-228.

Machytka et al., "Partial jejunal diversion using an incisionless magnetic anastomosis system: 1-year interim results in patients with obesity and diabetes," Gastrointestinal Endoscopy, 2017, vol. 86, No. 5, 904-912.

Matsuda et al., "Laparoscopic endoscopic cooperative surgery (LECS) for the upper gastrointestinal tract," Transl Gastroenterol Hepatol 2017, 2:40 (6 pages).

Miklavcic et al., "Electric Properties of Tissues," Wiley Encyclopedia of Biomedical Engineering, 2006, 1-12.

Sculpteo, "4D Printing: A technology coming from the future," 3D Learning Hub, dated no later than Aug. 26, 2021 (12 pages).

Seeley et al., "The Role of Gut Adaptation in the Potent Effects of Multiple Bariatric Surgeries on Obesity and Diabetes," Cell Metabolism 21, Mar. 3, 2015, 369-378.

Tamegai et al., "Laparoscopic and endoscopic cooperative surgery (LECS) to overcome the limitations of endoscopic resection for colorectal tumors," Endosc Int Open, Dec. 2018, 6(12): E1477-E1485.

Tokar et al., "Electrosurgical generators," Gastrointestinal Endoscopy, 2013, vol. 78, No. 2, 197-208.

Tomie et al., "Blue Laser Imaging-Bright Improves Endoscopic Recognition of Superficial Esophagael Squamous Cell Carcinoma," Gastroenterology Research and Practice, vol. 2016, Article ID 6140854, 7 pages.

Toposens, "Advanced Ultrasonic Sensors: What Makes Them Different? " available at <https://toposens.com/technology/>, 2020.

Toposens, "Beacon Based 3D Tracking System," available at <https://toposens.com/beacon-based-3d-ttracking-system/>, 2020.

U.S. Appl. No. 17/449,765 entitled "Cooperative Access Hybrid Procedures" filed Oct. 1, 2021.

U.S. Appl. No. 17/450,020 entitled "Methods for Controlling Cooperative Surgical Instruments" filed Oct. 5, 2021.

U.S. Appl. No. 17/450,025 entitled "Methods for Controlling Cooperative Surgical Instruments" filed Oct. 5, 2021.

U.S. Appl. No. 17/450,027 entitled "Methods for Controlling Cooperative Surgical Instruments" filed Oct. 5, 2021.

U.S. Appl. No. 17/493,913 entitled "Surgical Methods Using Fiducial Identification and Tracking" filed Oct. 5, 2021.

U.S. Appl. No. 17/493,904 entitled "Surgical Methods Using Multi-Source Imaging" filed Oct. 5, 2021.

U.S. Appl. No. 17/068,857 entitled "Adaptive Responses From Smart Packaging Of Drug Delivery Absorbable Adjuncts" filed Oct. 13, 2020.

U.S. Appl. No. 17/068,858 entitled "Drug Administration Devices That Communicate With Surgical Hubs" filed Oct. 13, 2020.

U.S. Appl. No. 17/068,859 entitled "Controlling Operation Of Drug Administration Devices Using Surgical Hubs" filed Oct. 13, 2020.

U.S. Appl. No. 17/068,863 entitled "Patient Monitoring Using Drug Administration Devices" filed Oct. 13, 2020.

U.S. Appl. No. 17/068,865 entitled "Monitoring And Communicating Information Using Drug Administration Devices" filed Oct. 13, 2020.

U.S. Appl. No. 17/068,867 entitled "Aggregating And Analyzing Drug Administration Data" filed Oct. 13, 2020.

Van Baar et al., "Endoscopic duodenal mucosal resurfacing for the treatment of type 2 diabetes mellitus: one year results from the first international, open label, prospective, multicentre study," Gut 2020, 69:295-303.

Yang et al., "4d printing reconfigurable, deployable and mechanically tunable materials," Material Science, 2019 (33 pages).

Zuo et al., "Pulmonary Intersegmental Places: Imaging Appearance and Possible Reasons Leading to Their Visualization," Radiology, vol. 267, No. 1, Apr. 2013, 267-275.

Aswathy SH, et al. Commercial hydrogels for biomedical applications. Heliyon. Apr. 7, 2020;6(4):e03719. doi: 10.1016/j.heliyon. 2020. e03719. PMID: 32280802; PMCID: PMC7138915. (Year: 2020).

(56) References Cited

OTHER PUBLICATIONS

Miwa H, Kondo T, Oshima T, Fukui H, Tomita T, Watari J. Esophageal sensation and esophageal hypersensitivity—overview from bench to bedside. J Neurogastroenterol Motil. Oct. 2010;16(4):353-62. doi: 10.5056/jnm.2010.16.4.353. Epub Oct. 30, 2010. PMID: 21103417; PMCID: PMC2978388. (Year: 2010).
Rønnestad I, Akiba Y, Kaji I, Kaunitz JD. Duodenal luminal nutrient sensing. Curr Opin Pharmacol. Dec. 2014;19:67-75. doi: 10.1016/j.coph.2014.07.010. Epub Aug. 9, 2014. PMID: 25113991; PMCID: PMC4845631. (Year: 2014).
International Search Report and Written Opinion for Intl. Pat. App. No. PCT/IB2022/059097 mailed Jan. 3, 2023.
Fang et al., "Intramucosal nerve cells in human small intestine," Journal of the autonomic nervous system 44.2-3 (1993): 129-136.
International Search Report and Written Opinion for Intl. Pat. App. No. PCT/IB2022/059087 mailed Jan. 2, 2023.
International Search Report and Written Opinion for Intl. Pat. App. No. PCT/IB2022/059095 mailed Jan. 2, 2023.
International Search Report and Written Opinion for Intl. Pat. App. No. PCT/IB2022/059091 mailed Jan. 3, 2023.
International Search Report and Written Opinion for Intl. Pat. App. No. PCT/IB2022/059093 mailed Jan. 5, 2023.
International Search Report and Written Opinion for Intl. Pat. App. No. PCT/IB2022/059086 mailed Feb. 14, 2023.
International Search Report and Written Opinion for Intl. Pat. App. No. PCT/IB2022/059085 mailed Mar. 15, 2023.

* cited by examiner 200
220
202
223
203
205
201a
201b
206
dw
de
dt
dA

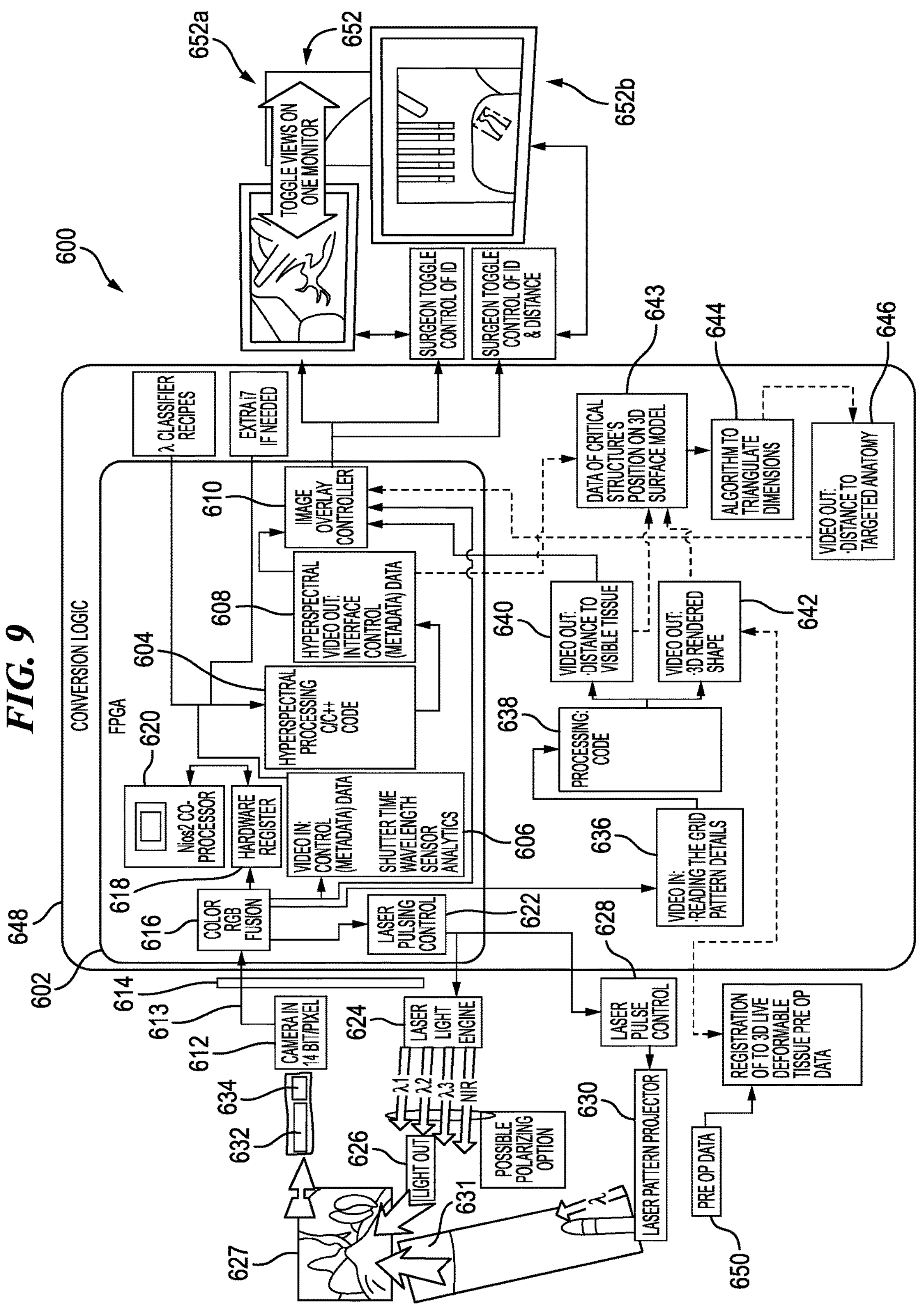
FIG. 9
600
CONVERSION LOGIC
FPGA
648
602
652a
652
652b
TOGGLE VIEWS ON ONE MONITOR
SURGEON TOGGLE CONTROL OF ID
SURGEON TOGGLE CONTROL OF ID & DISTANCE
λ CLASSIFIER RECIPES
EXTRA i7 IF NEEDED
610
IMAGE OVERLAY CONTROLLER
608
HYPERSPECTRAL VIDEO OUT: INTERFACE CONTROL (METADATA) DATA
604
HYPERSPECTRAL PROCESSING C/C++ CODE
620
Nios2 CO-PROCESSOR
HARDWARE REGISTER
VIDEO IN: CONTROL (METADATA) DATA
SHUTTER TIME WAVELENGTH SENSOR ANALYTICS
606
618
616
COLOR RGB FUSION
LASER PULSING CONTROL
622
643
DATA OF CRITICAL STRUCTURE'S POSITION ON 3D SURFACE MODEL
644
ALGORITHM TO TRIANGULATE DIMENSIONS
646
VIDEO OUT: ·DISTANCE TO TARGETED ANATOMY
640
VIDEO OUT: ·DISTANCE TO VISIBLE TISSUE
642
VIDEO OUT: ·3D RENDERED SHAPE
638
PROCESSING: CODE
636
VIDEO IN: ·READING THE GRID PATTERN DETAILS
628
614
613
612
CAMERA IN 14 BIT/PIXEL
624
LASER LIGHT ENGINE
λ1
λ2
λ3
NIR
LASER PULSE CONTROL
REGISTRATION OF TO 3D LIVE DEFORMABLE TISSUE PRE OP DATA
634
632
626
LIGHT OUT
POSSIBLE POLARIZING OPTION
630
LASER PATTERN PROJECTOR
PRE OP DATA
650
627
631

300
302
304
306
306
308
310
312
314
316
Absorption Coefficient μa [cm-1]
Wavelength λ [μm]
0.1
0.3
3
10
10^0
10^1
10^2
10^3
10^4
10^5
10^6

407c
408
425
404
409
d
403
401
406
424
407
402
410
405

430
OBJECT
EMITTED WAVE
RECEIVED WAVE
t
DELAY
q1
q2
DELAY IS A FUNCTION OF DISTANCE
RATIO OF "ON" LIGHT TO "OFF" LIGHT
c = SPEED OF LIGHT
t = LENGTH OF PULSE
q1 = ACCUMULATED CHARGE WHILE LIGHT IS EMITTED
q2 = ACCUMULATED CHARGE WHILE LIGHT IS NOT BEING EMITTED
$d = \frac{ct}{2} \cdot \frac{q_2}{q_1 + q_2}$ 700
704
713
705
702
706
HUB
708
VISUALIZATION SYSTEM
710
ROBOTIC SYSTEM
712
INTELLIGENT INSTRUMENT
702
706
HUB
708
VISUALIZATION SYSTEM
710
ROBOTIC SYSTEM
712
INTELLIGENT INSTRUMENT 1426W
1426L
1435
1432
DOSE
DOSE
1430a
1428
1426
1434
1430
1428b
1428a
1430b 1450a
1452t
1456
1452
1454

1456
1450
1450a

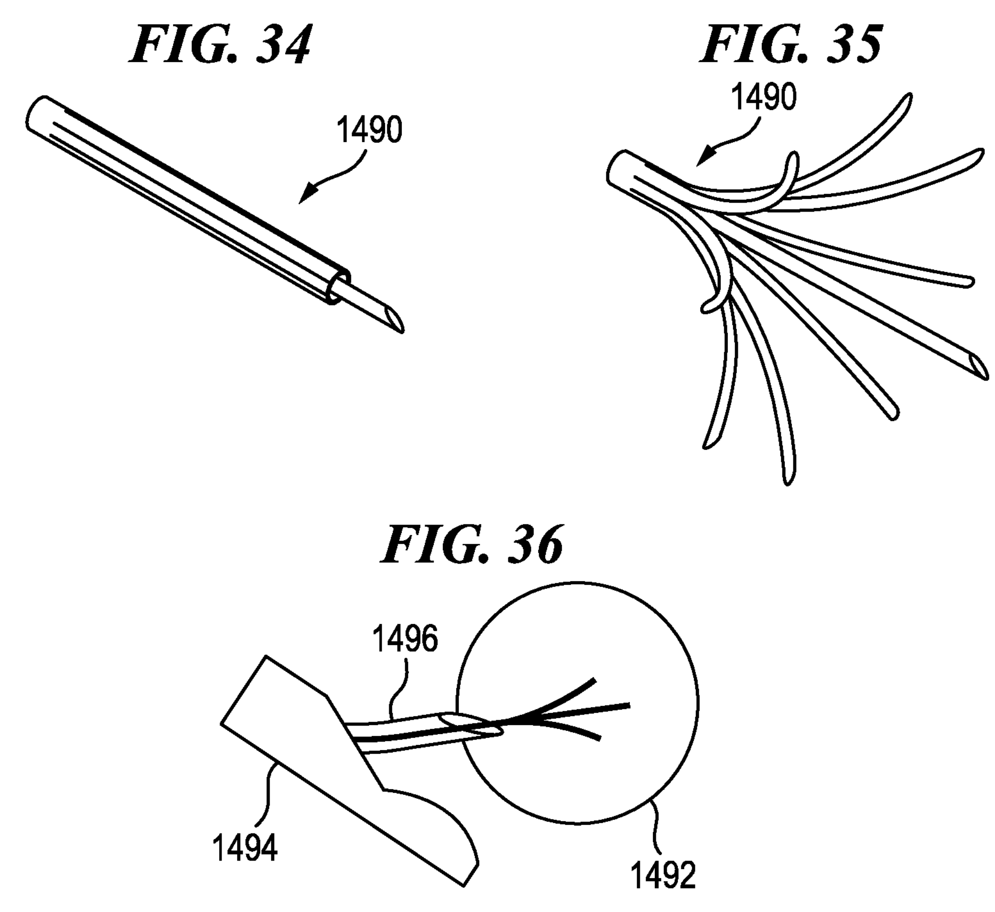
FIG. 34
1490
FIG. 35
1490
FIG. 36
1496
1494
1492
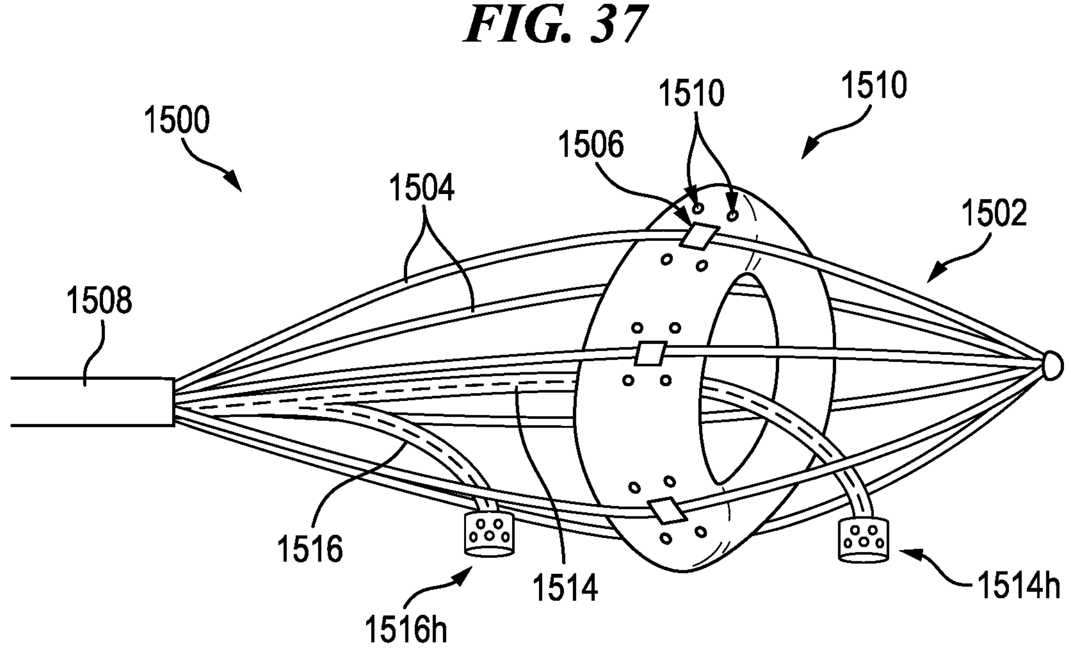
FIG. 37
1500
1510
1510
1506
1504
1502
1508
1516
1514
1516h
1514h 1560
1558
1566
1556
1550
1554
1552
1568
1562

FIG. 47
FIG. 48
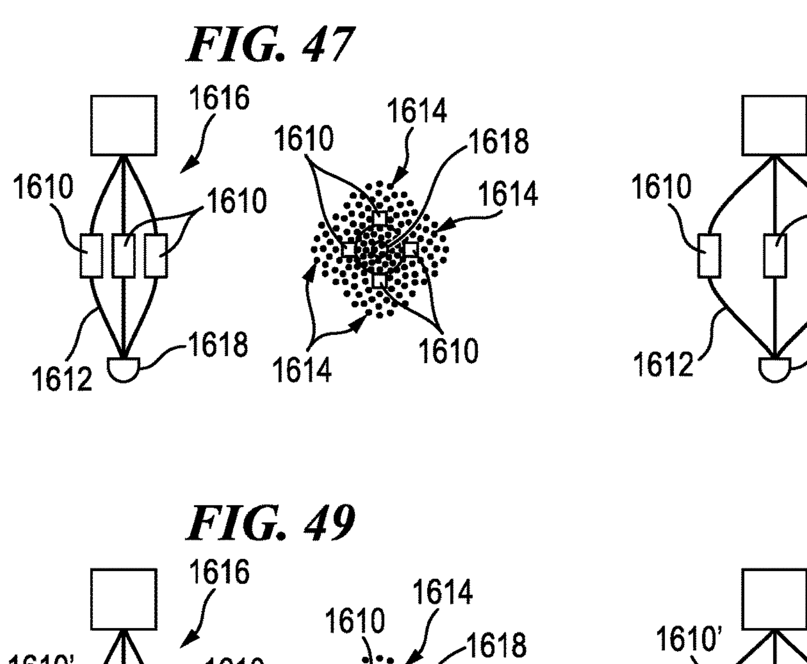
FIG. 49
FIG. 50
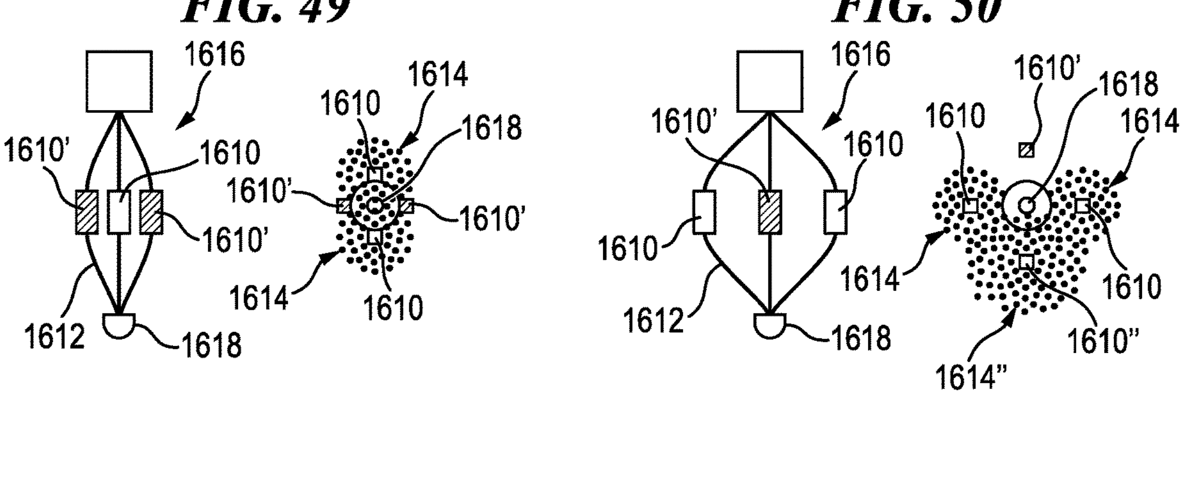
FIG. 51
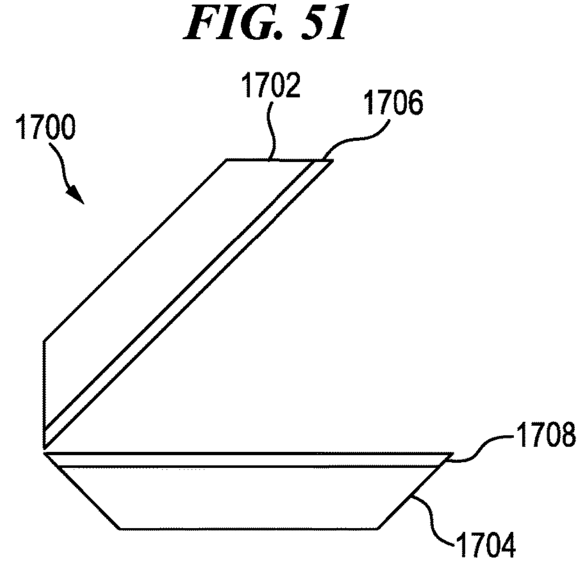

1710
1712
1716
1714

1718
1718
1718
1712
1718
1716
1720
1720
1714
1720
1720

1718
Voltage Source (+)
Rsense
SPST1
1716
SPST2
Rsense
Voltage Return (-)
1720
1718
1720

1718
1718
1720
1720
1716

FIG. 61
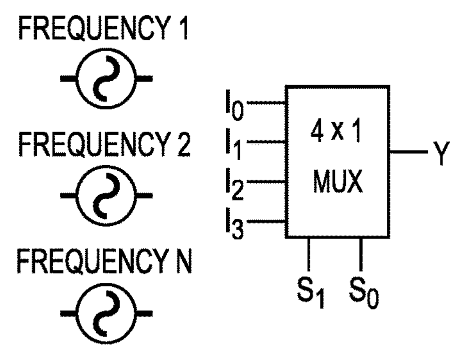
FIG. 62
RSENSE
JAW CHASSIS
1702, 1704
1706
1748
VOLTAGE SOURCE (+)
RSENSE
POSITIVE ELECTRODE
TISSUE
1708
RSENSE
VOLTAGE RETURN (-)
NEGATIVE ELECTRODE
1750
FIG. 63
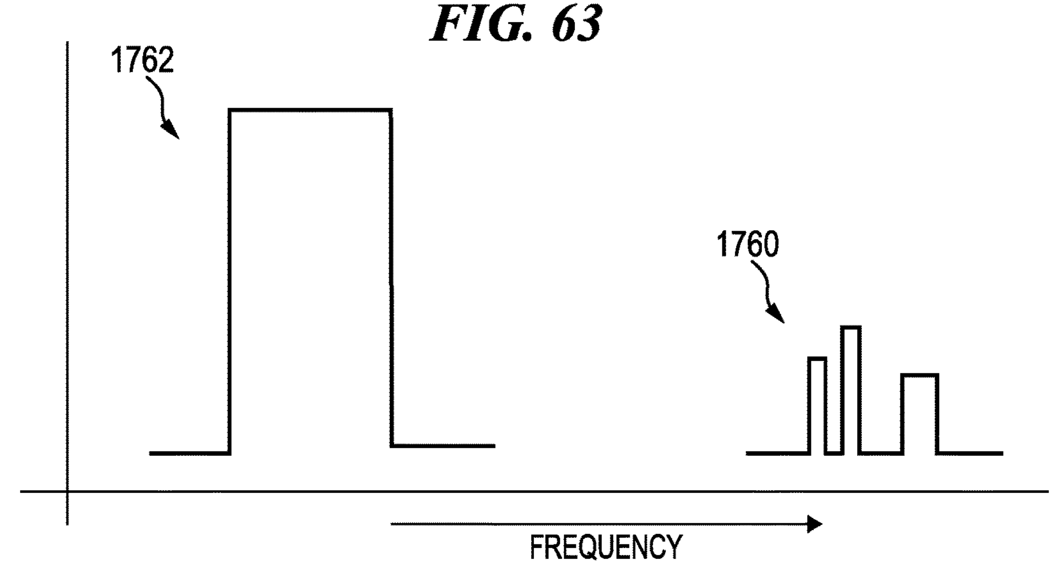

APPLIED SIGNAL
THERAPEUTIC SIGNAL
1782
MEASUREMENT FREQUENCIES
1780
TIME
APPLIED SIGNAL
FREQ 1
FREQ 2
FREQ 3
FREQ 4
TIME

FIG. 75
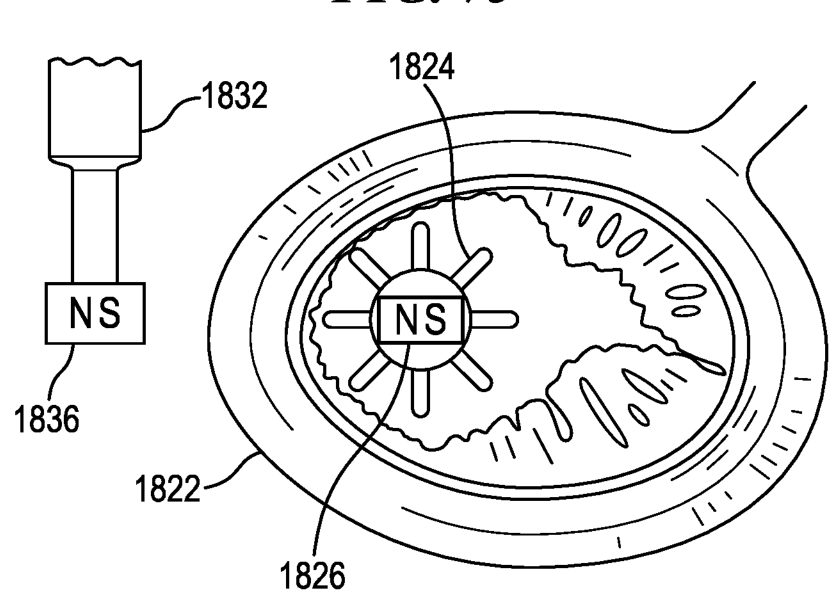
FIG. 76
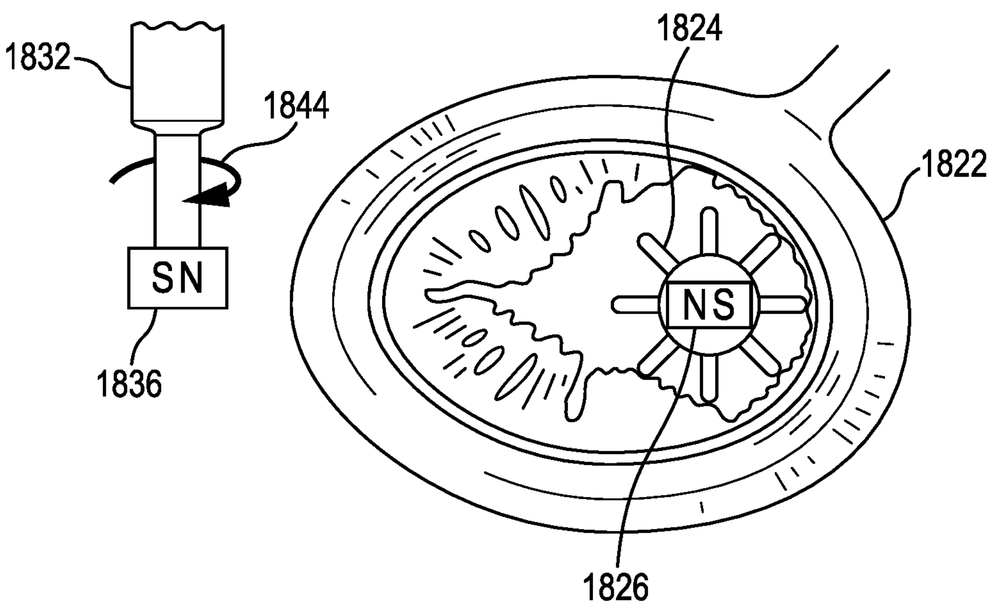

SURGICAL DEVICES, SYSTEMS, AND METHODS FOR CONTROL OF ONE VISUALIZATION WITH ANOTHER

CROSS REFERENCE TO RELATED APPLICATIONS

The present application claims priority to U.S. Prov. Pat. App. No. 63/249,658 entitled "Surgical Devices, Systems, And Methods For Control Of One Visualization With Another" filed Sep. 29, 2021, which is hereby incorporated by reference in its entirety.

FIELD

The present disclosure relates generally to surgical devices, systems, and methods for control of one visualization with another.

BACKGROUND

Surgical systems often incorporate an imaging system, which can allow medical practitioners to view a surgical site and/or one or more portions thereof on one or more displays, e.g., a monitor, a computer tablet screen, etc. The display(s) can be local and/or remote to a surgical theater. The imaging system can include a scope with a camera that views the surgical site and transmits the view to the one or more displays viewable by medical practitioner(s).

Imaging systems can be limited by the information that they are able to recognize and/or convey to the medical practitioner(s). For example, certain concealed structures, physical contours, and/or dimensions within a three-dimensional space may be unrecognizable intraoperatively by certain imaging systems. For another example, certain imaging systems may be incapable of communicating and/or conveying certain information to the medical practitioner(s) intraoperatively.

Accordingly, there remains a need for improved surgical imaging.

SUMMARY

In general, devices, systems, and methods for control of one visualization with another are provided.

In one aspect, a surgical method is provided that in one embodiment includes advancing a distal portion of a surgical device into a first anatomic space of a patient. The surgical device includes a plurality of electrodes in the distal portion thereof. The method also includes advancing a distal portion of an imaging device into a second, different anatomic space of a patient, and delivering energy to tissue with the plurality of electrodes located in the first anatomic space. The method also includes, with the plurality of electrodes delivering the energy to the tissue, gathering images with an imaging device using an image sensor of the imaging device located in the second anatomic space. The method also includes, with the plurality of electrodes delivering the energy to the tissue, controlling, with a controller, location and movement of the plurality of electrodes based on the images gathered by the imaging device.

The method can have any number of variations. For example, the control includes at least one of activating a first number of the plurality of electrodes to deliver the energy, a remaining number of the plurality of electrodes not delivering energy; preventing a temperature of the tissue from exceeding a predetermined threshold; and preventing an impedance of the tissue from being below a predetermined threshold. For another example, the movement control can include controlling longitudinal and multi-axial movement of the plurality of electrodes. For yet another example, the tissue can be mucosal tissue that is irregular longitudinally and circumferentially, and the control can ensure full thickness full circumferential mucosal ablation. For still another example, the gathered images can include infrared images indicating a thermal effect of the tissue, and the control can include controlling a retraction rate of the plurality of electrodes based on the thermal effect. For another example, the surgical device can include an expandable balloon, the plurality of electrodes can be printed on an exterior of the balloon, and the control can include controlling expansion of the balloon. For yet another example, the surgical device can include an ablation device, the plurality of electrodes can be attached to an expandable basket of the ablation device, and the control can include controlling expansion of the basket. For another example, the surgical device can include a magnet, a magnetic element can be positioned in the second anatomic space, and the method can further include determining a thickness of the tissue based on a magnetic attraction between the magnet and the magnetic element. For yet another example, the surgical device can include a magnetic collar, a magnetic element can be positioned in the second anatomic space, and the gathered images can include video images showing movement of the magnetic element as a proxy for movement of the plurality of electrodes in the first anatomic space. For still another example, the control can include controlling radial rotation of the electrode array. For another example, a surgical hub can include the controller. For yet another example, a robotic surgical system can include the controller, and the surgical device and the imaging device can each be releasably coupled to and be controlled by the robotic surgical system.

In another aspect, a surgical system is provided that in one embodiment includes a first surgical device including a distal portion configured to be advanced into a first anatomic space of a patient. The surgical device also includes a plurality of electrodes configured to delivery energy to tissue with the plurality of electrodes of the surgical device located in the first anatomic space. The system also includes an imaging device including a distal portion configured to be advanced into a second, different anatomic space of the patient and, with the plurality of electrodes delivering the energy to the tissue and with an image sensor of the imaging sensor of the imaging device located in the second anatomic space, gather images using the image sensor. The system also includes a controller configured to, with the plurality of electrodes delivering the energy to the tissue, control location and movement of the plurality of electrodes based on the images gathered by the imaging device.

The system can vary in any number of ways. For example, the control can include at least one of activating a first number of the plurality of electrodes to deliver the energy, a remaining number of the plurality of electrodes not delivering energy, preventing a temperature of the tissue from exceeding a predetermined threshold, and preventing an impedance of the tissue from being below a predetermined threshold. For another example, the movement control can include controlling longitudinal and multi-axial movement of the plurality of electrodes. For yet another example, the tissue can be mucosal tissue that is irregular longitudinally and circumferentially, and the control can also ensure full thickness full circumferential mucosal ablation. For still another example, the controller can also be configured to control movement and position of the imaging device. For another example, the gathered images can include infrared images indicating a thermal effect of the tissue, and the control can include controlling a retraction rate of the plurality of electrodes based on the thermal effect. For yet another example, the surgical device can include an expandable balloon, the plurality of electrodes can be printed on an exterior of the balloon, and the control can include controlling expansion of the balloon. For still another example, the surgical device can include an ablation device, the plurality of electrodes can be attached to an expandable basket of the ablation device, and the control can include controlling expansion of the basket. For another example, the surgical device can include a magnet, the surgical system can further include a magnetic element configured to be positioned in the second anatomic space, and the controller can be configured to determine a thickness of the tissue based on a magnetic attraction between the magnet and the magnetic element.

For yet another example, the surgical device can include a magnet, the surgical system can further include a magnetic element configured to be positioned in the second anatomic space, and the gathered images can include video images showing movement of the magnetic element as a proxy for movement of the plurality of electrodes in the first anatomic space. The controller can be configured to determine a thickness of the tissue based on the video images showing the movement of the magnetic element.

For another example, the control can includes controlling radial rotation of the plurality of electrodes. For still another example, a surgical hub can include the controller. For yet another example, a robotic surgical system can include the controller, and the surgical device and the imaging device can each be configured to releasably couple to and be controlled by the robotic surgical system.

BRIEF DESCRIPTION OF DRAWINGS

The present invention is described by way of reference to the accompanying figures which are as follows:

FIG. 9 is a schematic view of another embodiment of a control system for a surgical visualization system;

FIG. 34 is a perspective view of a distal portion of one embodiment of an ablation device in a compressed configuration;

FIG. 35 is a perspective view of the distal portion the ablation device of FIG. 34 in an expanded configuration;

FIG. 36 is a perspective view of the ablation device of FIG. 35 positioned relative to a tumor;

FIG. 37 is a perspective view of a distal portion of another embodiment of an ablation device;

FIG. 47 is a schematic view of one embodiment of an ablation device in a first state of expansion and with four electrodes of the ablation device delivering energy;

FIG. 48 is a schematic view of the ablation device of FIG. 47 in a second state of expansion and with the four electrodes delivering energy;

FIG. 49 is a schematic view of the ablation device of FIG. 47 in the first state of expansion and with two of the four electrodes delivering energy;

FIG. 50 is a schematic view of the ablation device of FIG. 47 in the second state of expansion and with three of the four electrodes delivering energy;

FIG. 51 is a side schematic view of one embodiment of an end effector including upper and lower jaws;

FIG. 61 is a schematic diagram showing one embodiment of multi-frequency application in the process of FIG. 60;

FIG. 62 is a schematic diagram of the process of FIG. 60;

FIG. 63 illustrates one embodiment of a variable frequency measurement pulse and a therapeutic treatment pulse that can be applied to tissue;

FIG. 75 is a cross-sectional view of the first magnet of FIG. 73 in an attraction configuration in the duodenum;

FIG. 76 is a cross-sectional view of the first magnet of FIG. 73 in a repulsion configuration in the duodenum;

DETAILED DESCRIPTION

Figure 1:
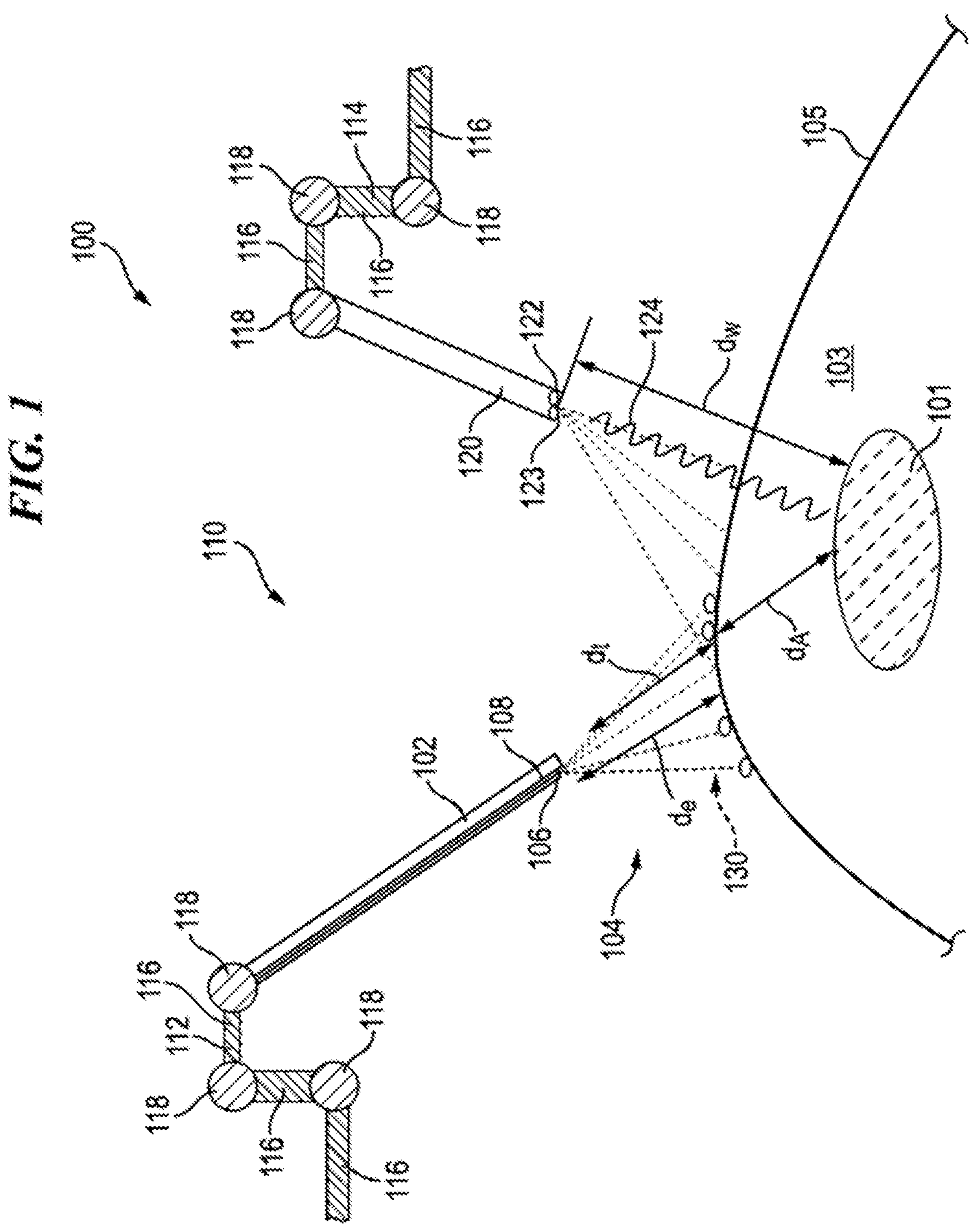
FIG. 1 is a schematic view of one embodiment of a surgical visualization system.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Surgical Visualization

In general, a surgical visualization system is configured to leverage "digital surgery" to obtain additional information about a patient's anatomy and/or a surgical procedure. The surgical visualization system is further configured to convey data to one or more medical practitioners in a helpful manner. Various aspects of the present disclosure provide improved visualization of the patient's anatomy and/or the surgical procedure, and/or use visualization to provide improved control of a surgical tool (also referred to herein as a "surgical device" or a "surgical instrument").

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization systems described herein can be used in combination with a robotic surgical system, surgical visualization systems are not limited to use with a robotic surgical system. In certain instances, surgical visualization using a surgical visualization system can occur without robotics and/or with limited and/or optional robotic assistance. Similarly, digital surgery can occur without robotics and/or with limited and/or optional robotic assistance.

In certain instances, a surgical system that incorporates a surgical visualization system may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, a surgical fastener, a clip, a tack, a bougie, a band, a plate, and other foreign structures. Critical structures can be determined on a patient-by-patient and/or a procedure-by-procedure basis. Smart dissection technology may provide, for example, improved intraoperative guidance for dissection and/or may enable smarter decisions with critical anatomy detection and avoidance technology.

A surgical system incorporating a surgical visualization system may enable smart anastomosis technologies that provide more consistent anastomoses at optimal location(s) with improved workflow. Cancer localization technologies may be improved with a surgical visualization platform. For example, cancer localization technologies can identify and track a cancer location, orientation, and its margins. In certain instances, the cancer localization technologies may compensate for movement of a surgical instrument, a patient, and/or the patient's anatomy during a surgical procedure in order to provide guidance back to the point of interest for medical practitioner(s).

A surgical visualization system may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies may be utilized without ionizing radiation and/or contrast agents. With respect to lymph node diagnostics and mapping, a surgical visualization platform may, for example, preoperatively locate, map, and ideally diagnose the lymph system and/or lymph nodes involved in cancerous diagnosis and staging.

During a surgical procedure, information available to a medical practitioner via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move pre-operatively (e.g., before a surgical procedure but after a preoperative scan) and/or intraoperatively. In such instances, the medical practitioner can be unable to accurately determine the location of a critical structure intraoperatively.

When the position of a critical structure is uncertain and/or when the proximity between the critical structure and a surgical tool is unknown, a medical practitioner's decision-making process can be inhibited. For example, a medical practitioner may avoid certain areas in order to avoid inadvertent dissection of a critical structure; however, the avoided area may be unnecessarily large and/or at least partially misplaced. Due to uncertainty and/or overly/excessive exercises in caution, the medical practitioner may not access certain desired regions. For example, excess caution may cause a medical practitioner to leave a portion of a tumor and/or other undesirable tissue in an effort to avoid a critical structure even if the critical structure is not in the particular area and/or would not be negatively impacted by the medical practitioner working in that particular area. In certain instances, surgical results can be improved with increased knowledge and/or certainty, which can allow a surgeon to be more accurate and, in certain instances, less conservative/more aggressive with respect to particular anatomical areas.

A surgical visualization system can allow for intraoperative identification and avoidance of critical structures. The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

Surgical visualization systems are described in detail below. In general, a surgical visualization system can include a first light emitter configured to emit a plurality of spectral waves, a second light emitter configured to emit a light pattern, and a receiver, or sensor, configured to detect visible light, molecular responses to the spectral waves (spectral imaging), and/or the light pattern. The surgical visualization system can also include an imaging system and a control circuit in signal communication with the receiver and the imaging system. Based on output from the receiver, the control circuit can determine a geometric surface map, e.g., three-dimensional surface topography, of the visible surfaces at the surgical site and a distance with respect to the surgical site, such as a distance to an at least partially concealed structure. The imaging system can convey the geometric surface map and the distance to a medical practitioner. In such instances, an augmented view of the surgical site provided to the medical practitioner can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of a surgical tool to the visible and obstructing tissue and/or to the at least partially concealed structure and/or a depth of the concealed structure below the visible surface of the obstructing tissue. For example, the visualization system can determine a distance with respect to the augmented line on the surface of the visible tissue and convey the distance to the imaging system.

Throughout the present disclosure, any reference to "light," unless specifically in reference to visible light, can include electromagnetic radiation (EMR) or photons in the visible and/or non-visible portions of the EMR wavelength spectrum. The visible spectrum, sometimes referred to as the optical spectrum or luminous spectrum, is that portion of the electromagnetic spectrum that is visible to (e.g., can be detected by) the human eye and may be referred to as "visible light" or simply "light." A typical human eye will respond to wavelengths in air that are from about 380 nm to about 750 nm. The invisible spectrum (e.g., the non-luminous spectrum) is that portion of the electromagnetic spectrum that lies below and above the visible spectrum. The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

FIG. 1 illustrates one embodiment of a surgical visualization system 100. The surgical visualization system 100 is configured to create a visual representation of a critical structure 101 within an anatomical field. The critical structure 101 can include a single critical structure or a plurality of critical structures. As discussed herein, the critical structure 101 can be any of a variety of structures, such as an anatomical structure, e.g., a ureter, an artery such as a superior mesenteric artery, a vein such as a portal vein, a nerve such as a phrenic nerve, a vessel, a tumor, or other anatomical structure, or a foreign structure, e.g., a surgical device, a surgical fastener, a surgical clip, a surgical tack, a bougie, a surgical band, a surgical plate, or other foreign structure. As discussed herein, the critical structure 101 can be identified on a patient-by-patient and/or a procedure-by-procedure basis. Embodiments of critical structures and of identifying critical structures using a visualization system are further described in U.S. Pat. No. 10,792,034 entitled "Visualization Of Surgical Devices" issued Oct. 6, 2020, which is hereby incorporated by reference in its entirety.

In some instances, the critical structure 101 can be embedded in tissue 103. The tissue 103 can be any of a variety of tissues, such as fat, connective tissue, adhesions, and/or organs. Stated differently, the critical structure 101 may be positioned below a surface 105 of the tissue 103. In such instances, the tissue 103 conceals the critical structure 101 from the medical practitioner's "naked eye" view. The tissue 103 also obscures the critical structure 101 from the view of an imaging device 120 of the surgical visualization system 100. Instead of being fully obscured, the critical structure 101 can be partially obscured from the view of the medical practitioner and/or the imaging device 120.

The surgical visualization system 100 can be used for clinical analysis and/or medical intervention. In certain instances, the surgical visualization system 100 can be used intraoperatively to provide real-time information to the medical practitioner during a surgical procedure, such as real-time information regarding proximity data, dimensions, and/or distances. A person skilled in the art will appreciate that information may not be precisely real time but nevertheless be considered to be real time for any of a variety of reasons, such as time delay induced by data transmission, time delay induced by data processing, and/or sensitivity of measurement equipment. The surgical visualization system 100 is configured for intraoperative identification of critical structure(s) and/or to facilitate the avoidance of the critical structure(s) 101 by a surgical device. For example, by identifying the critical structure 101, a medical practitioner can avoid maneuvering a surgical device around the critical structure 101 and/or a region in a predefined proximity of the critical structure 101 during a surgical procedure. For another example, by identifying the critical structure 101, a medical practitioner can avoid dissection of and/or near the critical structure 101, thereby helping to prevent damage to the critical structure 101 and/or helping to prevent a surgical device being used by the medical practitioner from being damaged by the critical structure 101.

The surgical visualization system 100 is configured to incorporate tissue identification and geometric surface mapping in combination with the surgical visualization system's distance sensor system 104. In combination, these features of the surgical visualization system 100 can determine a position of a critical structure 101 within the anatomical field and/or the proximity of a surgical device 102 to the surface 105 of visible tissue 103 and/or to the critical structure 101. Moreover, the surgical visualization system 100 includes an imaging system that includes the imaging device 120 configured to provide real-time views of the surgical site. The imaging device 120 can include, for example, a spectral camera (e.g., a hyperspectral camera, multispectral camera, or selective spectral camera), which is configured to detect reflected spectral waveforms and generate a spectral cube of images based on the molecular response to the different wavelengths. Views from the imaging device 120 can be provided in real time to a medical practitioner, such as on a display (e.g., a monitor, a computer tablet screen, etc.). The displayed views can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intraoperatively provide advanced data synthesis and integrated information to the medical practitioner.

The imaging device 120 can be configured to detect visible light, spectral light waves (visible or invisible), and a structured light pattern (visible or invisible). Examples of the imaging device 120 includes scopes, e.g., an endoscope, an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, or an exoscope. Scopes can be particularly useful in minimally invasive surgical procedures. In open surgery applications, the imaging device 120 may not include a scope.

The tissue identification subsystem can be achieved with a spectral imaging system. The spectral imaging system can rely on imaging such as hyperspectral imaging, multispectral imaging, or selective spectral imaging. Embodiments of hyperspectral imaging of tissue are further described in U.S. Pat. No. 9,274,047 entitled "System And Method For Gross Anatomic Pathology Using Hyperspectral Imaging" issued Mar. 1, 2016, which is hereby incorporated by reference in its entirety.

The surface mapping subsystem can be achieved with a light pattern system. Various surface mapping techniques using a light pattern (or structured light) for surface mapping can be utilized in the surgical visualization systems described herein. Structured light is the process of projecting a known pattern (often a grid or horizontal bars) on to a surface. In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Embodiments of surface mapping and a surgical system including a light source and a projector for projecting a light pattern are further described in U.S. Pat. Pub. No. 2017/0055819 entitled "Set Comprising A Surgical Instrument" published Mar. 2, 2017, U.S. Pat. Pub. No. 2017/0251900 entitled "Depiction System" published Sep. 7, 2017, and U.S. Pat. Pub. No. 2021/0196385 entitled "Surgical Systems For Generating Three Dimensional Constructs Of Anatomical Organs And Coupling Identified Anatomical Structures Thereto" published Jul. 1, 2021, which are hereby incorporated by reference in their entireties.

The distance determining system can be incorporated into the surface mapping system. For example, structured light can be utilized to generate a three-dimensional (3D) virtual model of the visible surface 105 and determine various distances with respect to the visible surface 105. Additionally or alternatively, the distance determining system can rely on time-of-flight measurements to determine one or more distances to the identified tissue (or other structures) at the surgical site.

The surgical visualization system 100 also includes a surgical device 102. The surgical device 102 can be any suitable surgical device. Examples of the surgical device 102 includes a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. In some embodiments, the surgical device 102 includes an end effector having opposing jaws that extend from a distal end of a shaft of the surgical device 102 and that are configured to engage tissue therebetween.

The surgical visualization system 100 can be configured to identify the critical structure 101 and a proximity of the surgical device 102 to the critical structure 101. The imaging device 120 of the surgical visualization system 100 is configured to detect light at various wavelengths, such as visible light, spectral light waves (visible or invisible), and a structured light pattern (visible or invisible). The imaging device 120 can include a plurality of lenses, sensors, and/or receivers for detecting the different signals. For example, the imaging device 120 can be a hyperspectral, multispectral, or selective spectral camera, as described herein. The imaging device 120 can include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a 3D image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, a field of view of the imaging device 120 can overlap with a pattern of light (structured light) on the surface 105 of the tissue 103, as shown in FIG. 1.

As in this illustrated embodiment, the surgical visualization system 100 can be incorporated into a robotic surgical system 110. The robotic surgical system 110 can have a variety of configurations, as discussed herein. In this illustrated embodiment, the robotic surgical system 110 includes a first robotic arm 112 and a second robotic arm 114. The robotic arms 112, 114 each include rigid structural members 116 and joints 118, which can include servomotor controls. The first robotic arm 112 is configured to maneuver the surgical device 102, and the second robotic arm 114 is configured to maneuver the imaging device 120. A robotic control unit of the robotic surgical system 110 is configured to issue control motions to the first and second robotic arms 112, 114, which can affect the surgical device 102 and the imaging device 120, respectively.

In some embodiments, one or more of the robotic arms 112, 114 can be separate from the main robotic system 110 used in the surgical procedure. For example, at least one of the robotic arms 112, 114 can be positioned and registered to a particular coordinate system without a servomotor control. For example, a closed-loop control system and/or a plurality of sensors for the robotic arms 112, 114 can control and/or register the position of the robotic arm(s) 112, 114 relative to the particular coordinate system. Similarly, the position of the surgical device 102 and the imaging device 120 can be registered relative to a particular coordinate system.

Examples of robotic surgical systems include the Ottava™ robotic-assisted surgery system (Johnson & Johnson of New Brunswick, NJ), da Vinci® surgical systems (Intuitive Surgical, Inc. of Sunnyvale, CA), the Hugo™ robotic-assisted surgery system (Medtronic PLC of Minneapolis, MN), the Versius™ surgical robotic system (CMR Surgical Ltd of Cambridge, UK), and the Monarch™ platform (Auris Health, Inc. of Redwood City, CA). Embodiments of various robotic surgical systems and using robotic surgical systems are further described in U.S. Pat. Pub. No. 2018/0177556 entitled "Flexible Instrument Insertion Using An Adaptive Force Threshold" filed Dec. 28, 2016, U.S. Pat. Pub. No. 2020/0000530 entitled "Systems And Techniques For Providing Multiple Perspectives During Medical Procedures" filed Apr. 16, 2019, U.S. Pat. Pub. No. 2020/0170720 entitled "Image-Based Branch Detection And Mapping For Navigation" filed Feb. 7, 2020, U.S. Pat. Pub. No. 2020/0188043 entitled "Surgical Robotics System" filed Dec. 9, 2019, U.S. Pat. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical visualization system 100 also includes an emitter 106. The emitter 106 is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120. In one aspect, the projected light array 130 is employed by the surgical visualization system 100 to determine the shape defined by the surface 105 of the tissue 103 and/or motion of the surface 105 intraoperatively. The imaging device 120 is configured to detect the projected light arrays 130 reflected from the surface 105 to determine the topography of the surface 105 and various distances with respect to the surface 105.

As in this illustrated embodiment, the imaging device 120 can include an optical waveform emitter 123, such as by being mounted on or otherwise attached on the imaging device 120. The optical waveform emitter 123 is configured to emit electromagnetic radiation 124 (near-infrared (NIR) photons) that can penetrate the surface 105 of the tissue 103 and reach the critical structure 101. The imaging device 120 and the optical waveform emitter 123 can be positionable by the robotic arm 114. The optical waveform emitter 123 is mounted on or otherwise on the imaging device 120 but in other embodiments can be positioned on a separate surgical device from the imaging device 120. A corresponding waveform sensor 122 (e.g., an image sensor, spectrometer, or vibrational sensor) of the imaging device 120 is configured to detect the effect of the electromagnetic radiation received by the waveform sensor 122. The wavelengths of the electromagnetic radiation 124 emitted by the optical waveform emitter 123 are configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 can be variable. The waveform sensor 122 and optical waveform emitter 123 can be inclusive of a multispectral imaging system and/or a selective spectral imaging system, for example. In other instances, the waveform sensor 122 and optical waveform emitter 123 can be inclusive of a photoacoustic imaging system, for example.

The distance sensor system 104 of the surgical visualization system 100 is configured to determine one or more distances at the surgical site. The distance sensor system 104 can be a time-of-flight distance sensor system that includes an emitter, such as the emitter 106 as in this illustrated embodiment, and that includes a receiver 108. In other instances, the time-of-flight emitter can be separate from the structured light emitter. The emitter 106 can include a very tiny laser source, and the receiver 108 can include a matching sensor. The distance sensor system 104 is configured to detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104.

The receiver 108 of the distance sensor system 104 is positioned on the surgical device 102 in this illustrated embodiment, but in other embodiments the receiver 108 can be mounted on a separate surgical device instead of the surgical device 102. For example, the receiver 108 can be mounted on a cannula or trocar through which the surgical device 102 extends to reach the surgical site. In still other embodiments, the receiver 108 for the distance sensor system 104 can be mounted on a separate robotically-controlled arm of the robotic system 110 (e.g., on the second robotic arm 114) than the first robotic arm 112 to which the surgical device 102 is coupled, can be mounted on a movable arm that is operated by another robot, or be mounted to an operating room (OR) table or fixture. In some embodiments, the imaging device 120 includes the receiver 108 to allow for determining the distance from the emitter 106 to the surface 105 of the tissue 103 using a line between the emitter 106 on the surgical device 102 and the imaging device 120. For example, a distance $d_e$ can be triangulated based on known positions of the emitter 106 (on the surgical device 102) and the receiver 108 (on the imaging device 120) of the distance sensor system 104. The 3D position of the receiver 108 can be known and/or registered to the robot coordinate plane intraoperatively.

As in this illustrated embodiment, the position of the emitter 106 of the distance sensor system 104 can be controlled by the first robotic arm 112, and the position of the receiver 108 of the distance sensor system 104 can be controlled by the second robotic arm 114. In other embodiments, the surgical visualization system 100 can be utilized apart from a robotic system. In such instances, the distance sensor system 104 can be independent of the robotic system.

In FIG. 1, distance $d_e$ is emitter-to-tissue distance from the emitter 106 to the surface 105 of the tissue 103, and distance $d_t$ is device-to-tissue distance from a distal end of the surgical device 102 to the surface 105 of the tissue 103. The distance sensor system 104 is configured to determine the emitter-to-tissue distance $d_e$. The device-to-tissue distance $d_t$ is obtainable from the known position of the emitter 106 on the surgical device 102, e.g., on a shaft thereof proximal to the surgical device's distal end, relative to the distal end of the surgical device 102. In other words, when the distance between the emitter 106 and the distal end of the surgical device 102 is known, the device-to-tissue distance $d_t$ can be determined from the emitter-to-tissue distance $d_e$. In some embodiments, the shaft of the surgical device 102 can include one or more articulation joints and can be articulatable with respect to the emitter 106 and jaws at the distal end of the surgical device 102. The articulation configuration can include a multi-joint vertebrae-like structure, for example. In some embodiments, a 3D camera can be utilized to triangulate one or more distances to the surface 105.

In FIG. 1, distance $d_w$ is camera-to-critical structure distance from the optical waveform emitter 123 located on the imaging device 120 to the surface of the critical structure 101, and distance $d_A$ is a depth of the critical structure 101 below the surface 105 of the tissue 103 (e.g., the distance between the portion of the surface 105 closest to the surgical device 102 and the critical structure 101). The time-of-flight of the optical waveforms emitted from the optical waveform emitter 123 located on the imaging device 120 are configured to determine the camera-to-critical structure distance $d_w$.

Figure 2:
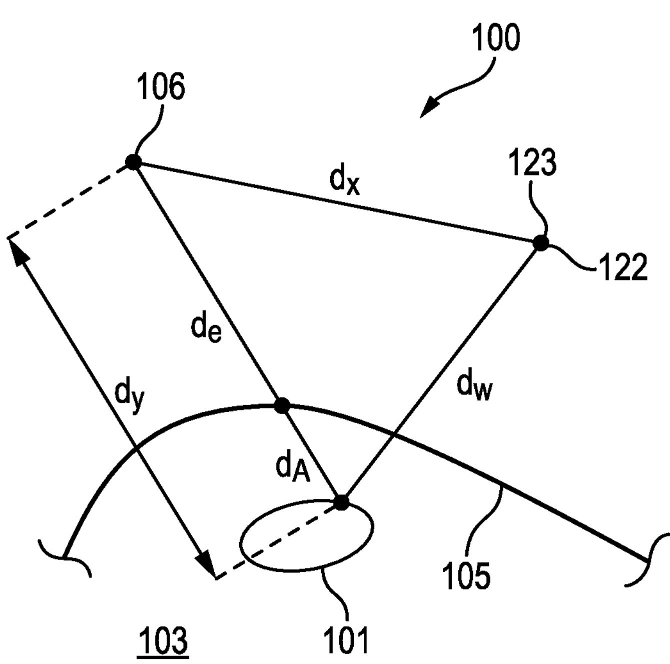
FIG. 2 is a schematic view of triangularization between a surgical device, an imaging device, and a critical structure of FIG. 1.

As shown in FIG. 2, the depth $d_A$ of the critical structure 101 relative to the surface 105 of the tissue 103 can be determined by triangulating from the camera-to-critical structure distance $d_w$ and known positions of the emitter 106 on the surgical device 102 and the optical waveform emitter 123 on the imaging device 120 (and, thus, the known distance $d_x$ therebetween) to determine distance $d_y$, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, the distance $d_A$ can be determined from an ultrasound, a registered magnetic resonance imaging (MRI), or computerized tomography (CT) scan. In still other instances, the distance $d_A$ can be determined with spectral imaging because the detection signal received by the imaging device 120 can vary based on the type of material, e.g., type of the tissue 103. For example, fat can decrease the detection signal in a first way, or a first amount, and collagen can decrease the detection signal in a different, second way, or a second amount.

Figure 3:
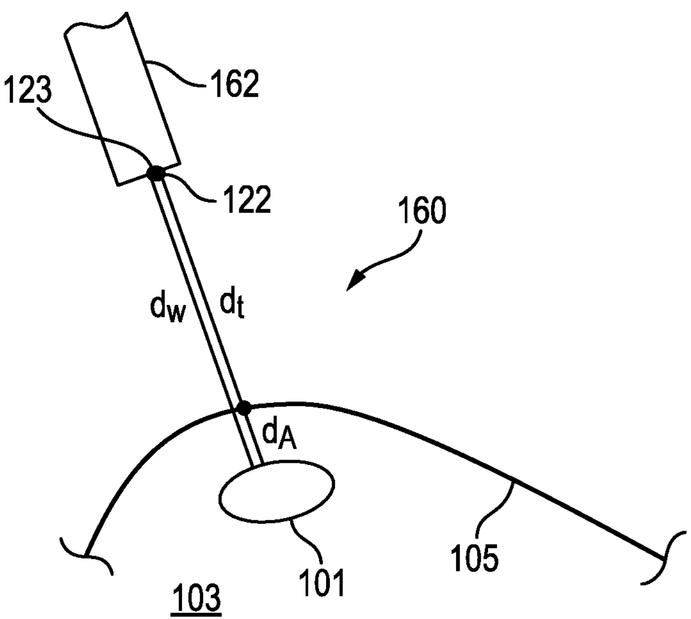
FIG. 3 is a schematic view of another embodiment of a surgical visualization system.

In another embodiment of a surgical visualization system 160 illustrated in FIG. 3, a surgical device 162, and not the imaging device 120, includes the optical waveform emitter 123 and the waveform sensor 122 that is configured to detect the reflected waveforms. The optical waveform emitter 123 is configured to emit waveforms for determining the distances $d_t$ and $d_w$ from a common device, such as the surgical device 162, as described herein. In such instances, the distance $d_A$ from the surface 105 of the tissue 103 to the surface of the critical structure 101 can be determined as follows:

$$d_A = d_w - d_t$$

Figure 4:
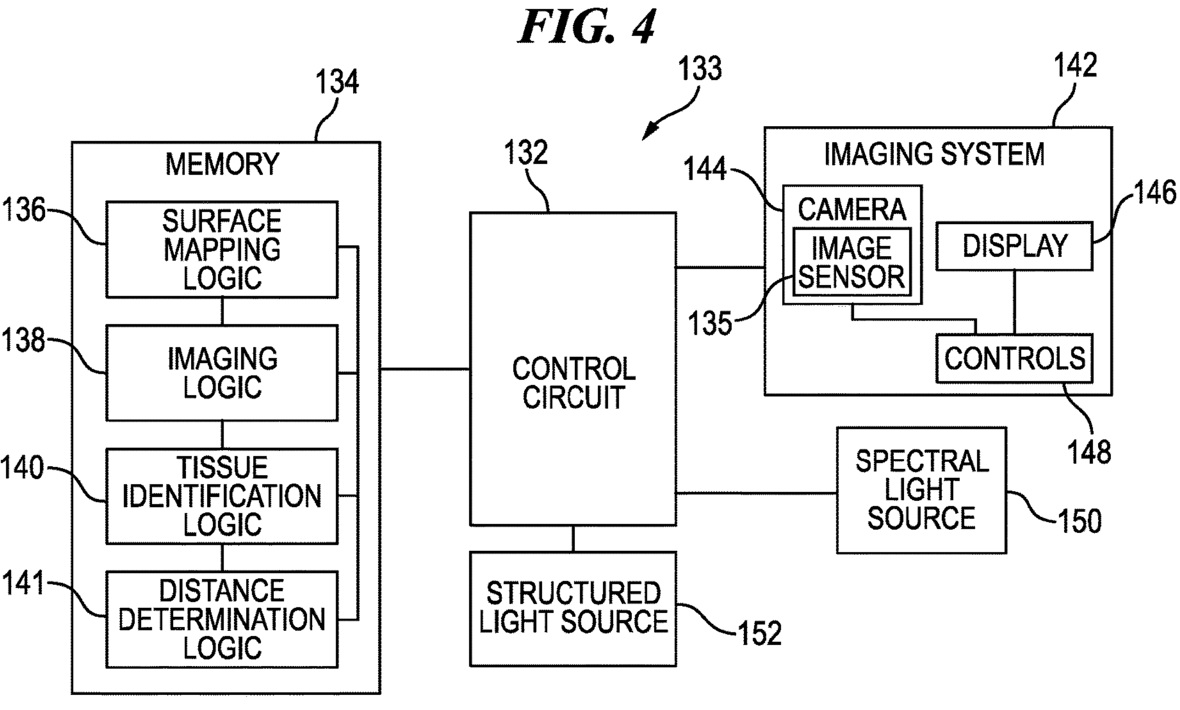
FIG. 4 is a schematic view of one embodiment of a control system for a surgical visualization system.

The surgical visualization system 100 includes a control system configured to control various aspects of the surgical visualization system 100. FIG. 4 illustrates one embodiment of a control system 133 that can be utilized as the control system of the surgical visualization system 100 (or other surgical visualization system described herein). The control system 133 includes a control circuit 132 configured to be in signal communication with a memory 134. The memory 134 is configured to store instructions executable by the control circuit 132, such as instructions to determine and/or recognize critical structures (e.g., the critical structure 101 of FIG. 1), instructions to determine and/or compute one or more distances and/or three-dimensional digital representations, and instructions to communicate information to a medical practitioner. As in this illustrated embodiment, the memory 134 can store surface mapping logic 136, imaging logic 138, tissue identification logic 140, and distance determining logic 141, although the memory 134 can store any combinations of the logics 136, 138, 140, 141 and/or can combine various logics together. The control system 133 also includes an imaging system 142 including a camera 144 (e.g., the imaging system including the imaging device 120 of FIG. 1), a display 146 (e.g., a monitor, a computer tablet screen, etc.), and controls 148 of the camera 144 and the display 146. The camera 144 includes an image sensor 135 (e.g., the waveform sensor 122) configured to receive signals from various light sources emitting light at various visible and invisible spectra (e.g., visible light, spectral imagers, three-dimensional lens, etc.). The display 146 is configured to depict real, virtual, and/or virtually-augmented images and/or information to a medical practitioner.

In an exemplary embodiment, the image sensor 135 is a solid-state electronic device containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of the image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors are sensitive to wavelengths in a range of about 350 nm to about 1050 nm, such as in a range of about 400 nm to about 1000 nm. A person skilled in the art will appreciate that a value may not be precisely at a value but nevertheless considered to be about that value for any of a variety of reasons, such as sensitivity of measurement equipment and manufacturing tolerances. CMOS sensors are, in general, more sensitive to IR wavelengths than CCD sensors. Solid state image sensors are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g., Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes an emitter (e.g., the emitter 106) including a spectral light source 150 and a structured light source 152 each operably coupled to the control circuit 133. A single source can be pulsed to emit wavelengths of light in the spectral light source 150 range and wavelengths of light in the structured light source 152 range. Alternatively, a single light source can be pulsed to provide light in the invisible spectrum (e.g., infrared spectral light) and wavelengths of light on the visible spectrum. The spectral light source 150 can be, for example, a hyperspectral light source, a multispectral light source, and/or a selective spectral light source. The tissue identification logic 140 is configured to identify critical structure(s) (e.g., the critical structure 101 of FIG. 1) via data from the spectral light source 150 received by the image sensor 135 of the camera 144. The surface mapping logic 136 is configured to determine the surface contours of the visible tissue (e.g., the tissue 103) based on reflected structured light. With time-of-flight measurements, the distance determining logic 141 is configured to determine one or more distance(s) to the visible tissue and/or the critical structure. Output from each of the surface mapping logic 136, the tissue identification logic 140, and the distance determining logic 141 is configured to be provided to the imaging logic 138, and combined, blended, and/or overlaid by the imaging logic 138 to be conveyed to a medical practitioner via the display 146 of the imaging system 142.

Figure 5:
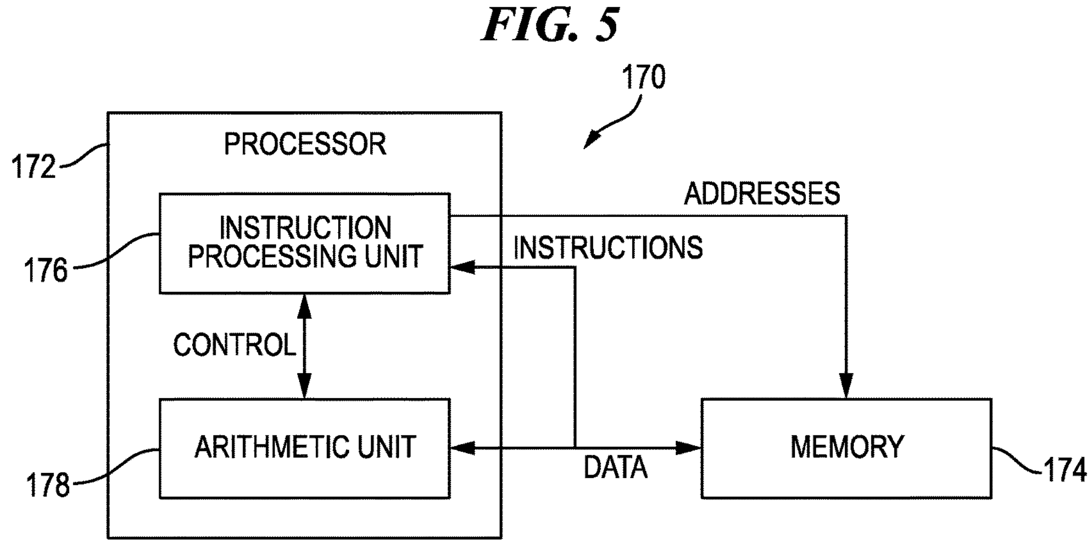
FIG. 5 is a schematic view of one embodiment of a control circuit of a control system for a surgical visualization system.

The control circuit 132 can have a variety of configurations. FIG. 5 illustrates one embodiment of a control circuit 170 that can be used as the control circuit 132 configured to control aspects of the surgical visualization system 100. The control circuit 170 is configured to implement various processes described herein. The control circuit 170 includes a microcontroller that includes a processor 172 (e.g., a microprocessor or microcontroller) operably coupled to a memory 174. The memory 174 is configured to store machine-executable instructions that, when executed by the processor 172, cause the processor 172 to execute machine instructions to implement various processes described herein. The processor 172 can be any one of a number of single-core or multicore processors known in the art. The memory 174 can include volatile and non-volatile storage media. The processor 172 includes an instruction processing unit 176 and an arithmetic unit 178. The instruction processing unit 176 is configured to receive instructions from the memory 174.

Figure 6:
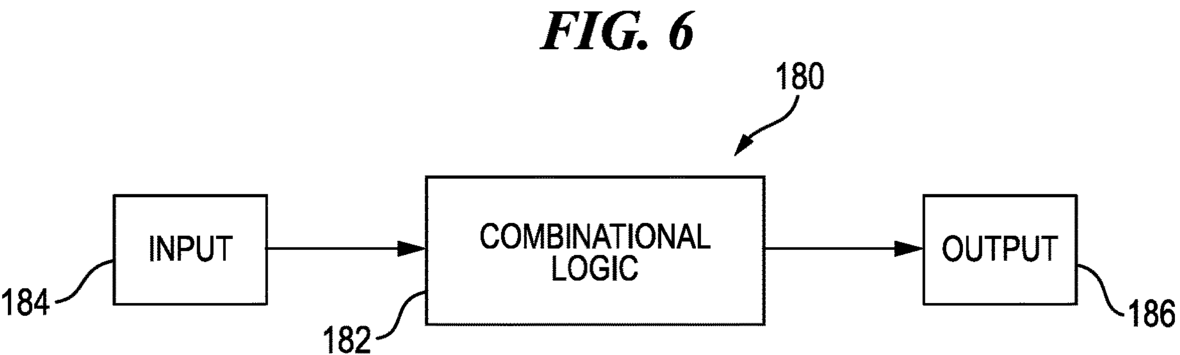
FIG. 6 is a schematic view of one embodiment of a combinational logic circuit of a surgical visualization system.

The surface mapping logic 136, the imaging logic 138, the tissue identification logic 140, and the distance determining logic 141 can have a variety of configurations. FIG. 6 illustrates one embodiment of a combinational logic circuit 180 configured to control aspects of the surgical visualization system 100 using logic such as one or more of the surface mapping logic 136, the imaging logic 138, the tissue identification logic 140, and the distance determining logic 141. The combinational logic circuit 180 includes a finite state machine that includes a combinational logic 182 configured to receive data associated with a surgical device (e.g. the surgical device 102 and/or the imaging device 120) at an input 184, process the data by the combinational logic 182, and provide an output 186 to a control circuit (e.g., the control circuit 132).

Figure 7:
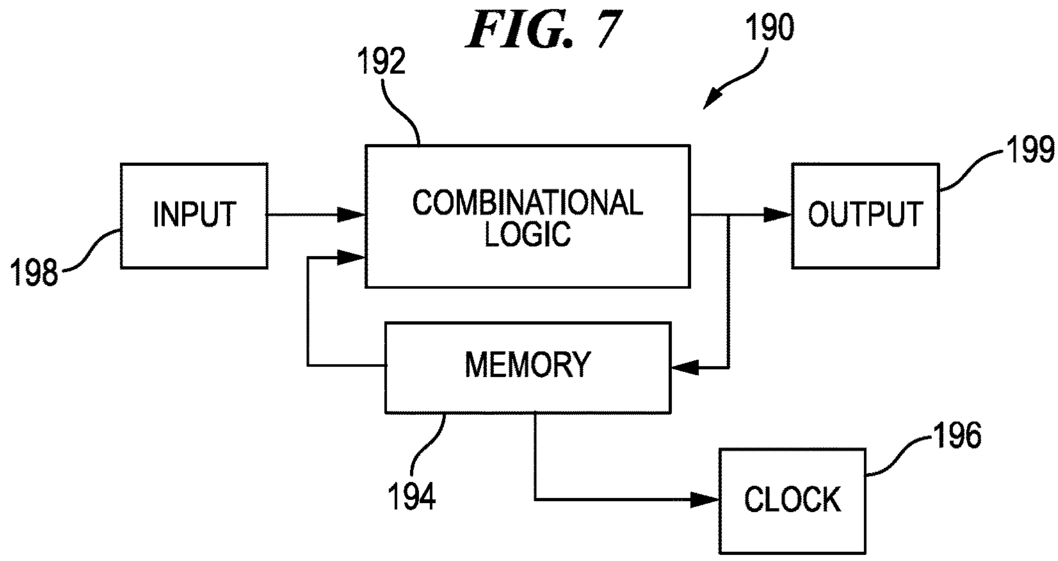
FIG. 7 is a schematic view of one embodiment of a sequential logic circuit of a surgical visualization system.

FIG. 7 illustrates one embodiment of a sequential logic circuit 190 configured to control aspects of the surgical visualization system 100 using logic such as one or more of the surface mapping logic 136, the imaging logic 138, the tissue identification logic 140, and the distance determining logic 141. The sequential logic circuit 190 includes a finite state machine that includes a combinational logic 192, a memory 194, and a clock 196. The memory 194 is configured to store a current state of the finite state machine. The sequential logic circuit 190 can be synchronous or asynchronous. The combinational logic 192 is configured to receive data associated with a surgical device (e.g. the surgical device 102 and/or the imaging device 120) at an input 198, process the data by the combinational logic 192, and provide an output 199 to a control circuit (e.g., the control circuit 132). In some embodiments, the sequential logic circuit 190 can include a combination of a processor (e.g., processor 172 of FIG. 5) and a finite state machine to implement various processes herein. In some embodiments, the finite state machine can include a combination of a combinational logic circuit (e.g., the combinational logic circuit 192 of FIG. 7) and the sequential logic circuit 190.

Figure 8:
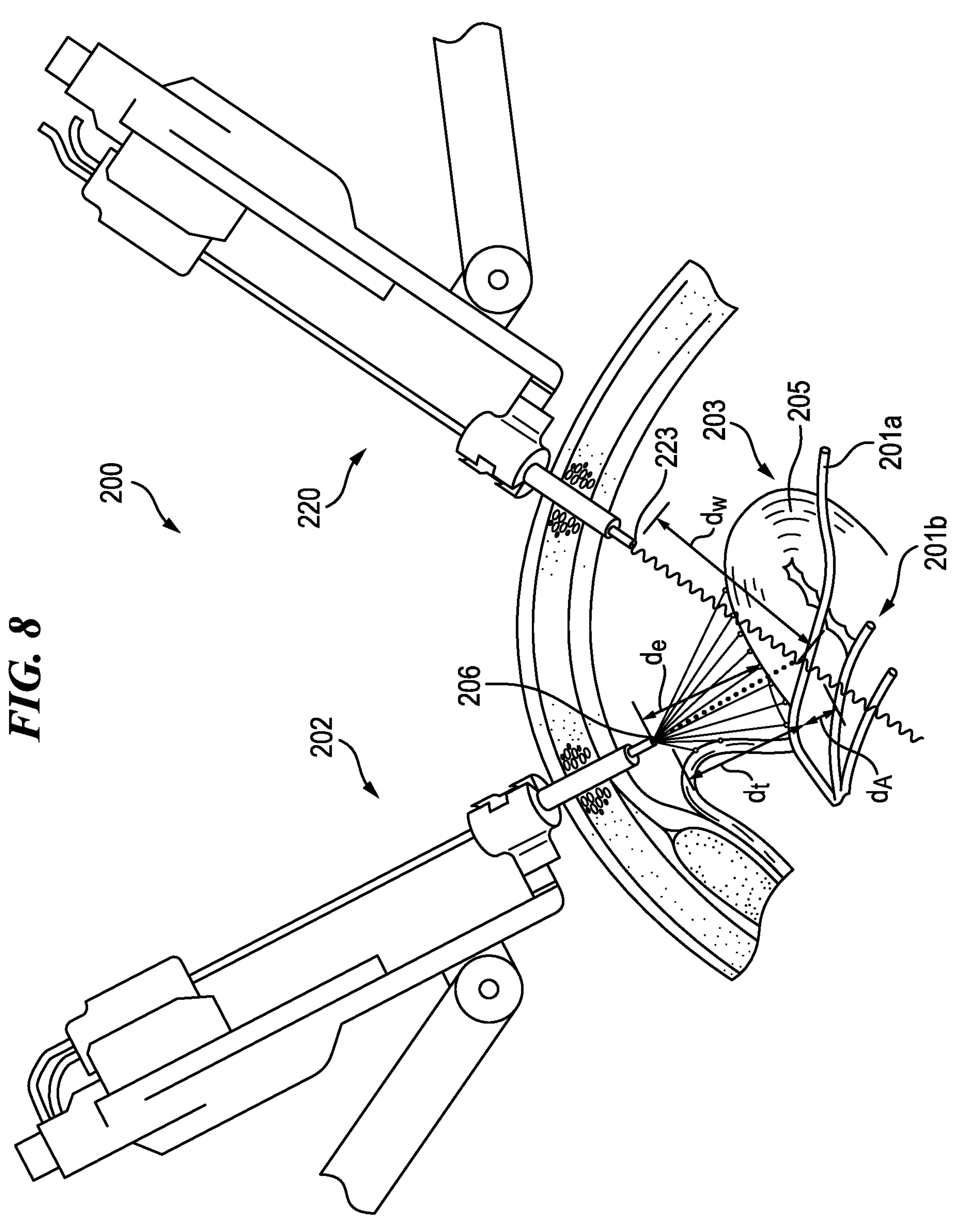
FIG. 8 is a schematic view of yet another embodiment of a surgical visualization system.

FIG. 8 illustrates another embodiment of a surgical visualization system 200. The surgical visualization system 200 is generally configured and used similar to the surgical visualization system 100 of FIG. 1, e.g., includes a surgical device 202 and an imaging device 220. The imaging device 220 includes a spectral light emitter 223 configured to emit spectral light in a plurality of wavelengths to obtain a spectral image of hidden structures, for example. The imaging device 220 can also include a three-dimensional camera and associated electronic processing circuits. The surgical visualization system 200 is shown being utilized intraoperatively to identify and facilitate avoidance of certain critical structures, such as a ureter 201*a* and vessels 201*b*, in an organ 203 (a uterus in this embodiment) that are not visible on a surface 205 of the organ 203.

The surgical visualization system 200 is configured to determine an emitter-to-tissue distance $d_e$ from an emitter 206 on the surgical device 202 to the surface 205 of the uterus 203 via structured light. The surgical visualization system 200 is configured to extrapolate a device-to-tissue distance $d_t$ from the surgical device 202 to the surface 205 of the uterus 203 based on the emitter-to-tissue distance $d_e$. The surgical visualization system 200 is also configured to determine a tissue-to-ureter distance $d_A$ from the ureter 201*a* to the surface 205 and a camera-to ureter distance $d_w$ from the imaging device 220 to the ureter 201*a*. As described herein, e.g., with respect to the surgical visualization system 100 of FIG. 1, the surgical visualization system 200 is configured to determine the distance $d_w$ with spectral imaging and time-of-flight sensors, for example. In various embodiments, the surgical visualization system 200 can determine (e.g., triangulate) the tissue-to-ureter distance $d_A$ (or depth) based on other distances and/or the surface mapping logic described herein.

As mentioned above, a surgical visualization system includes a control system configured to control various aspects of the surgical visualization system. The control system can have a variety of configurations. FIG. 9 illustrates one embodiment of a control system 600 for a surgical visualization system, such as the surgical visualization system 100 of FIG. 1, the surgical visualization system 200 of FIG. 8, or other surgical visualization system described herein. The control system 600 is a conversion system that integrates spectral signature tissue identification and structured light tissue positioning to identify a critical structure, especially when those structure(s) are obscured by tissue, e.g., by fat, connective tissue, blood tissue, and/or organ(s), and/or by blood, and/or to detect tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 configured to convert tissue data to usable information for surgeons and/or other medical practitioners. For example, variable reflectance based on wavelengths with respect to obscuring material can be utilized to identify the critical structure in the anatomy. Moreover, the control system 600 is configured to combine the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various embodiments, the control system 600 is configured to provide warnings to a medical practitioner when in the proximity of one or more critical structures. Various algorithms can be employed to guide robotic automation and semiautomated approaches based on the surgical procedure and proximity to the critical structure(s).

A projected array of lights is employed by the control system 600 to determine tissue shape and motion intraoperatively. Alternatively, flash Lidar may be utilized for surface mapping of the tissue.

The control system 600 is configured to detect the critical structure, which as mentioned above can include one or more critical structures, and provide an image overlay of the critical structure and measure the distance to the surface of the visible tissue and the distance to the embedded/buried critical structure(s). The control system 600 can measure the distance to the surface of the visible tissue or detect the critical structure and provide an image overlay of the critical structure.

The control system 600 includes a spectral control circuit 602. The spectral control circuit 602 can be a field programmable gate array (FPGA) or another suitable circuit configuration, such as the configurations described with respect to FIG. 6, FIG. 7, and FIG. 8. The spectral control circuit 602 includes a processor 604 configured to receive video input signals from a video input processor 606. The processor 604 can be configured for hyperspectral processing and can utilize C/C++ code, for example. The video input processor 606 is configured to receive video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 is configured to provides the video output signal to an image overlay controller 610.

The video input processor 606 is operatively coupled to a camera 612 at the patient side via a patient isolation circuit 614. The camera 612 includes a solid state image sensor 634. The patient isolation circuit 614 can include a plurality of transformers so that the patient is isolated from other circuits in the system. The camera 612 is configured to receive intraoperative images through optics 632 and the image sensor 634. The image sensor 634 can include a CMOS image sensor, for example, or can include another image sensor technology, such as those discussed herein in connection with FIG. 4. The camera 612 is configured to output 613 images in 14 bit/pixel signals. A person skilled in the art will appreciate that higher or lower pixel resolutions can be employed. The isolated camera output signal 613 is provided to a color RGB fusion circuit 616, which in this illustrated embodiment employs a hardware register 618 and a Nios2 co-processor 620 configured to process the camera output signal 613. A color RGB fusion output signal is provided to the video input processor 606 and a laser pulsing control circuit 622.

The laser pulsing control circuit 622 is configured to control a laser light engine 624. The laser light engine 624 is configured to output light in a plurality of wavelengths (λ1, λ2, λ3, . . . λn) including near infrared (NIR). The laser light engine 624 can operate in a plurality of modes. For example, the laser light engine 624 can operate in two modes. In a first mode, e.g., a normal operating mode, the laser light engine 624 is configured to output an illuminating signal. In a second mode, e.g., an identification mode, the laser light engine 624 is configured to output RGBG and NIR light. In various embodiments, the laser light engine 624 can operate in a polarizing mode.

Light output 626 from the laser light engine 624 is configured to illuminate targeted anatomy in an intraoperative surgical site 627. The laser pulsing control circuit 622 is also configured to control a laser pulse controller 628 for a laser pattern projector 630 configured to project a laser light pattern 631, such as a grid or pattern of lines and/or dots, at a predetermined wavelength (λ2) on an operative tissue or organ at the surgical site 627. The camera 612 is configured to receive the patterned light as well as the reflected light output through the camera optics 632. The image sensor 634 is configured to convert the received light into a digital signal.

The color RGB fusion circuit 616 is also configured to output signals to the image overlay controller 610 and a video input module 636 for reading the laser light pattern 631 projected onto the targeted anatomy at the surgical site 627 by the laser pattern projector 630. A processing module 638 is configured to process the laser light pattern 631 and output a first video output signal 640 representative of the distance to the visible tissue at the surgical site 627. The data is provided to the image overlay controller 610. The processing module 638 is also configured to output a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 is configured to determine the distance (e.g., distance $d_A$ of FIG. 1) to a buried critical structure (e.g., via triangularization algorithms 644), and the distance to the buried critical structure can be provided to the image overlay controller 610 via a video out processor 646. The foregoing conversion logic can encompass the conversion logic circuit 648 intermediate video monitors 652 and the camera 612/laser pattern projector 630 positioned at the surgical site 627.

Preoperative data 650, such as from a CT or MRI scan, can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Embodiments of registration of preoperative data are further described in U.S. Pat. Pub. No. 2020/0015907 entitled "Integration Of Imaging Data" filed Sep. 11, 2018, which is hereby incorporated by reference herein in its entirety.

The video monitors 652 are configured to output the integrated/augmented views from the image overlay controller 610. A medical practitioner can select and/or toggle between different views on one or more displays. On a first display 652*a*, which is a monitor in this illustrated embodiment, the medical practitioner can toggle between (A) a view in which a three-dimensional rendering of the visible tissue is depicted and (B) an augmented view in which one or more hidden critical structures are depicted over the three-dimensional rendering of the visible tissue. On a second display 652*b*, which is a monitor in this illustrated embodiment, the medical practitioner can toggle on distance measurements to one or more hidden critical structures and/or the surface of visible tissue, for example.

The various surgical visualization systems described herein can be utilized to visualize various different types of tissues and/or anatomical structures, including tissues and/or anatomical structures that may be obscured from being visualized by EMR in the visible portion of the spectrum.

The surgical visualization system can utilize a spectral imaging system, as mentioned above, which can be configured to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be configured to characterize the tissue type of the tissue being visualized based upon the particular combination of constituent materials.

Figure 10:
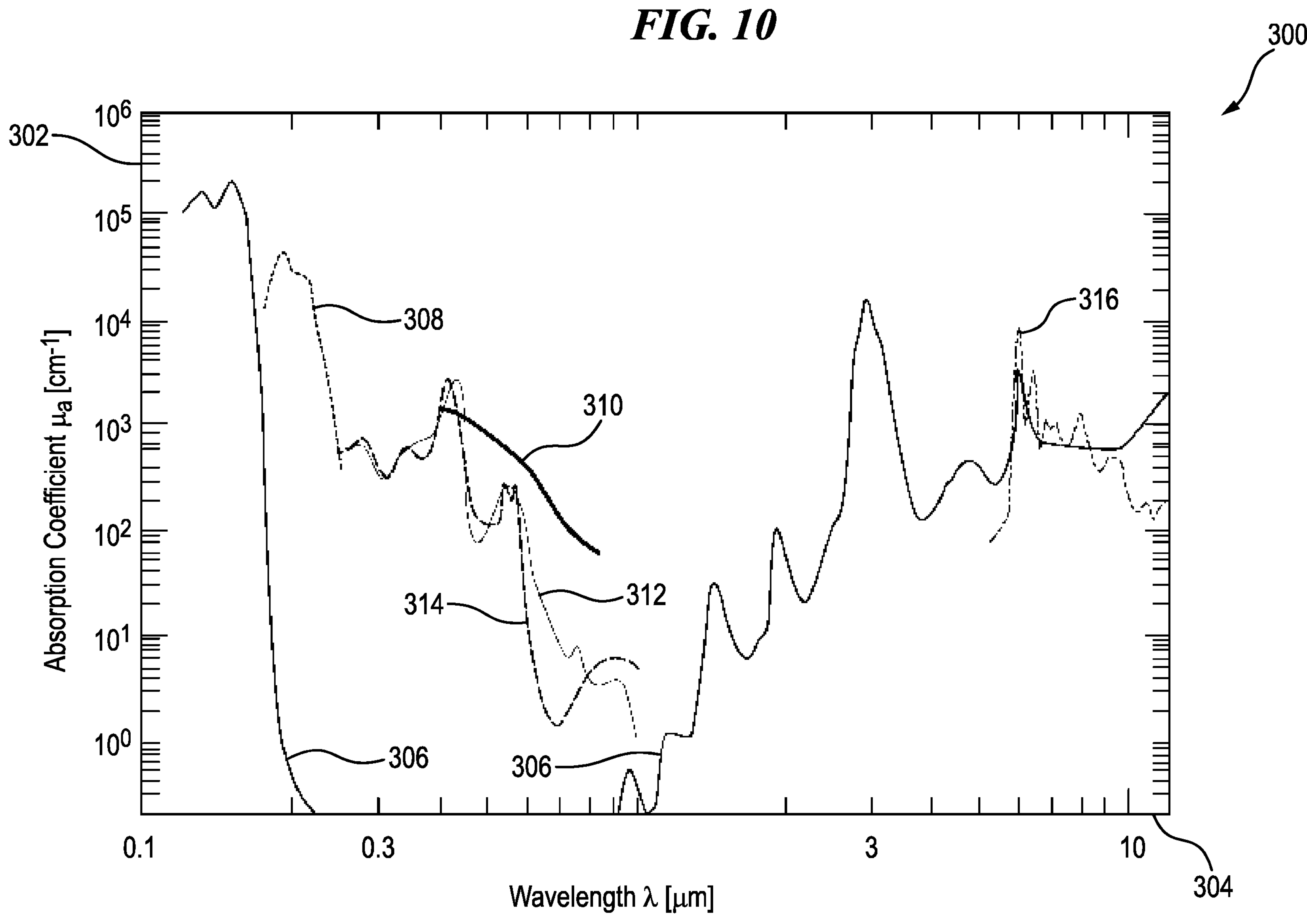
FIG. 10 is a graph showing wavelength versus absorption coefficient for various biological materials.

FIG. 10 shows a graph 300 depicting how the absorption coefficient of various biological materials varies across the EMR wavelength spectrum. In the graph 300, the vertical axis 302 represents absorption coefficient of the biological material in $cm^{-1}$, and the horizontal axis 304 represents EMR wavelength in μm. A first line 306 in the graph 300 represents the absorption coefficient of water at various EMR wavelengths, a second line 308 represents the absorption coefficient of protein at various EMR wavelengths, a third line 310 represents the absorption coefficient of melanin at various EMR wavelengths, a fourth line 312 represents the absorption coefficient of deoxygenated hemoglobin at various EMR wavelengths, a fifth line 314 represents the absorption coefficient of oxygenated hemoglobin at various EMR wavelengths, and a sixth line 316 represents the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system of a surgical visualization system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 11:
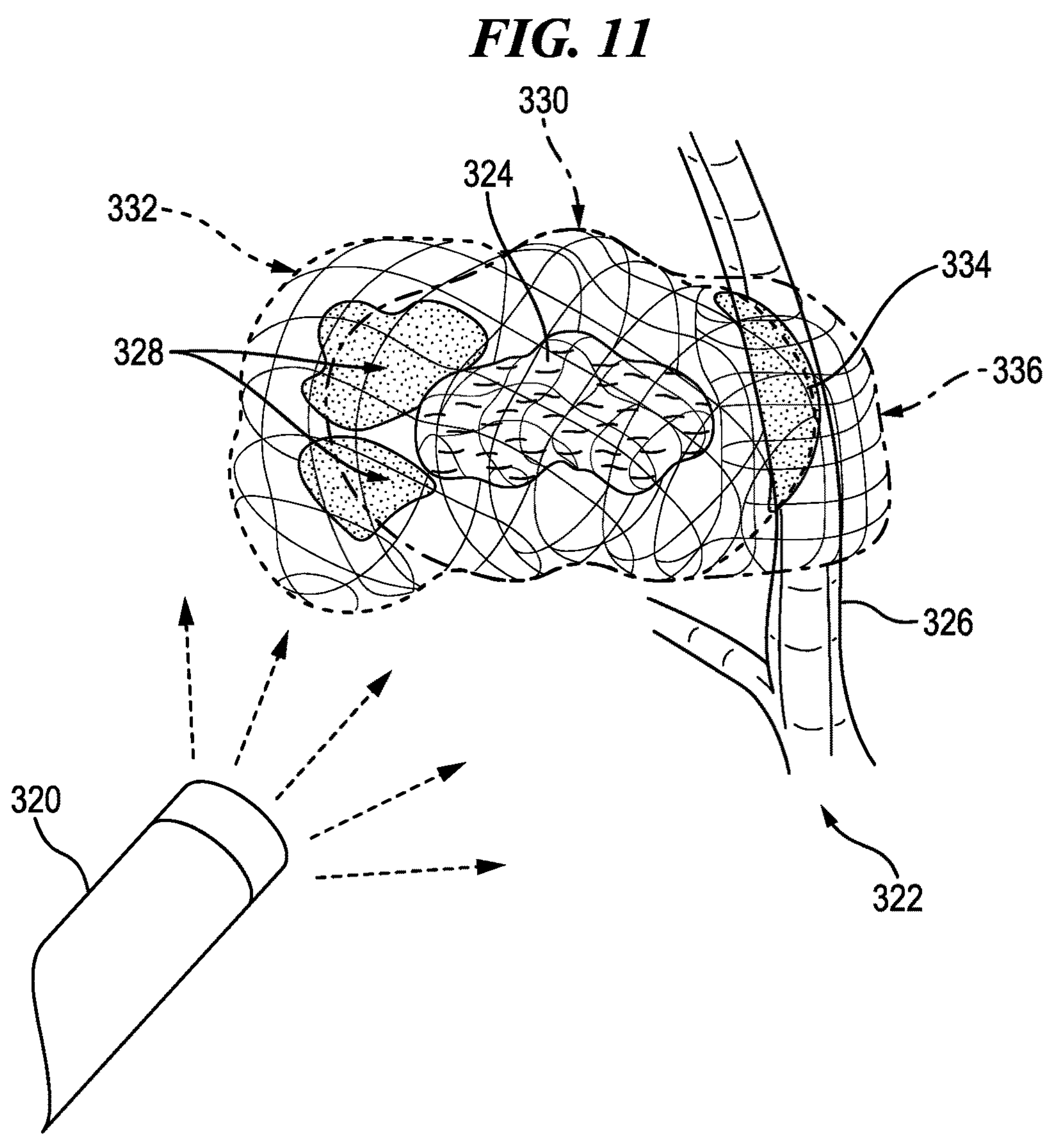
FIG. 11 is a schematic view of one embodiment of a spectral emitter visualizing a surgical site.

FIG. 11 shows an embodiment of the utilization of spectral imaging techniques to visualize different tissue types and/or anatomical structures. In FIG. 11, a spectral emitter 320 (e.g., the spectral light source 150 of FIG. 4) is being utilized by an imaging system to visualize a surgical site 322. The EMR emitted by the spectral emitter 320 and reflected from the tissues and/or structures at the surgical site 322 is received by an image sensor (e.g., the image sensor 135 of FIG. 4) to visualize the tissues and/or structures, which can be either visible (e.g., be located at a surface of the surgical site 322) or obscured (e.g., underlay other tissue and/or structures at the surgical site 322). In this embodiment, an imaging system (e.g., the imaging system 142 of FIG. 4) visualizes a tumor 324, an artery 326, and various abnormalities 328 (e.g., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system (e.g., the display 146 of the imaging system 142 of FIG. 4), on a primary display (e.g., the primary display 819 of FIG. 19), on a non-sterile display (e.g., the non-sterile displays 807, 809 of FIG. 19), on a display of a surgical hub (e.g., the display of the surgical hub 806 of FIG. 19), on a device/instrument display, and/or on another display.

The imaging system can be configured to tailor or update the displayed surgical site visualization according to the identified tissue and/or structure types. For example, as shown in FIG. 11, the imaging system can display a margin 330 associated with the tumor 324 being visualized on a display screen associated with or coupled to the imaging system, on a primary display, on a non-sterile display, on a display of a surgical hub, on a device/instrument display, and/or on another display. The margin 330 can indicate the area or amount of tissue that should be excised to ensure complete removal of the tumor 324. A size of the margin 330 can be, for example, in a range of about 5 mm to about 10 mm. The surgical visualization system's control system (e.g., the control system 133 of FIG. 4) can be configured to control or update the dimensions of the margin 330 based on the tissues and/or structures identified by the imaging system. In this illustrated embodiment, the imaging system has identified multiple abnormalities 328 within the field of view (FOV). Accordingly, the control system can adjust the displayed margin 330 to a first updated margin 332 having sufficient dimensions to encompass the abnormalities 328. Further, the imaging system has also identified the artery 326 partially overlapping with the initially displayed margin 330 (as indicated by a highlighted region 334 of the artery 326). Accordingly, the control system can adjust the displayed margin to a second updated margin 336 having sufficient dimensions to encompass the relevant portion of the artery 326.

Figure 12:
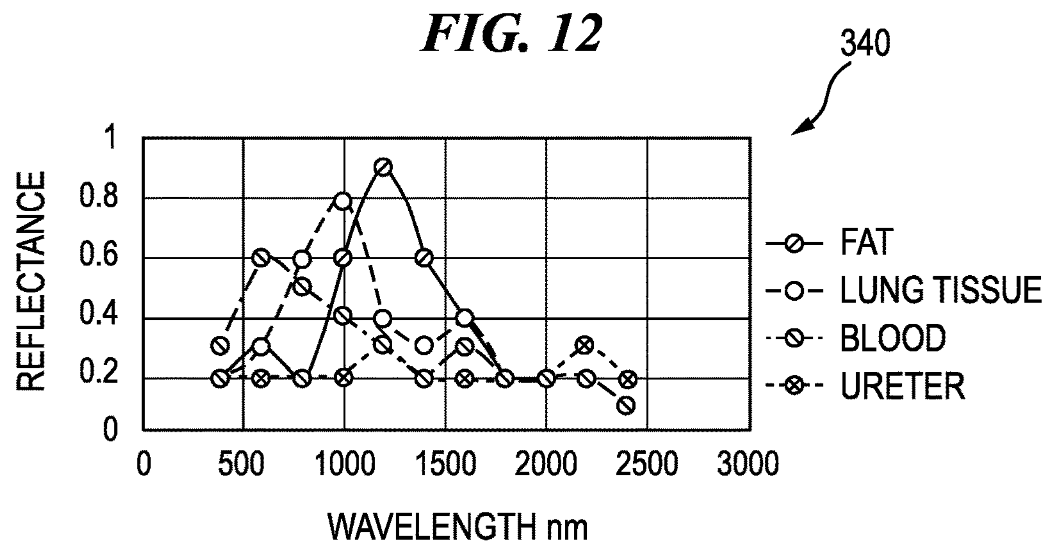
FIG. 12 is a graph depicting illustrative hyperspectral identifying signatures to differentiate a ureter from obscurants.
Figure 13:
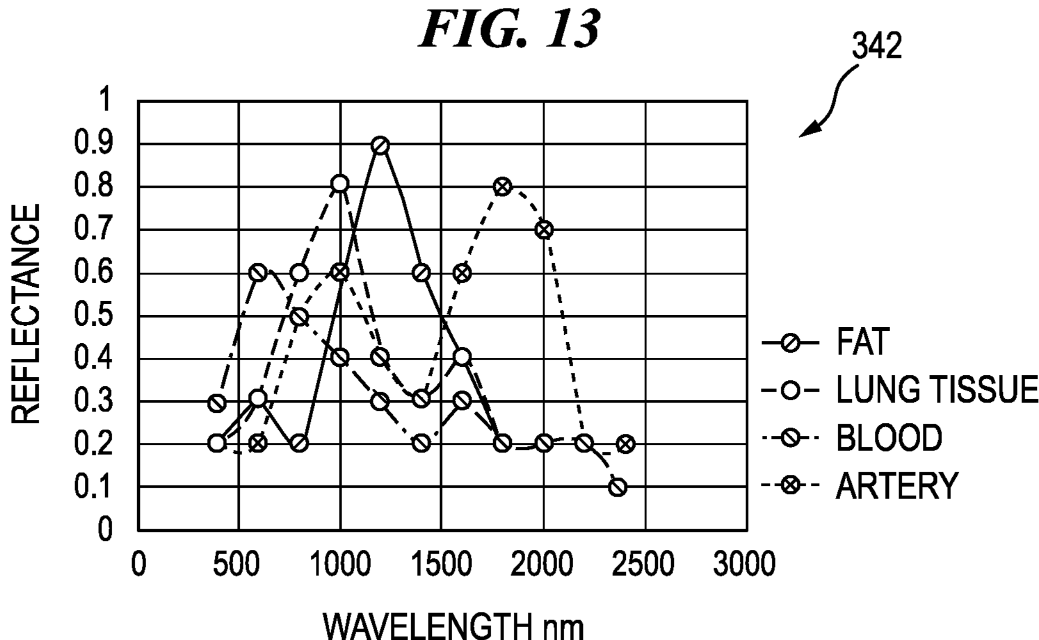
FIG. 13 is a graph depicting illustrative hyperspectral identifying signatures to differentiate an artery from obscurants.
Figure 14:
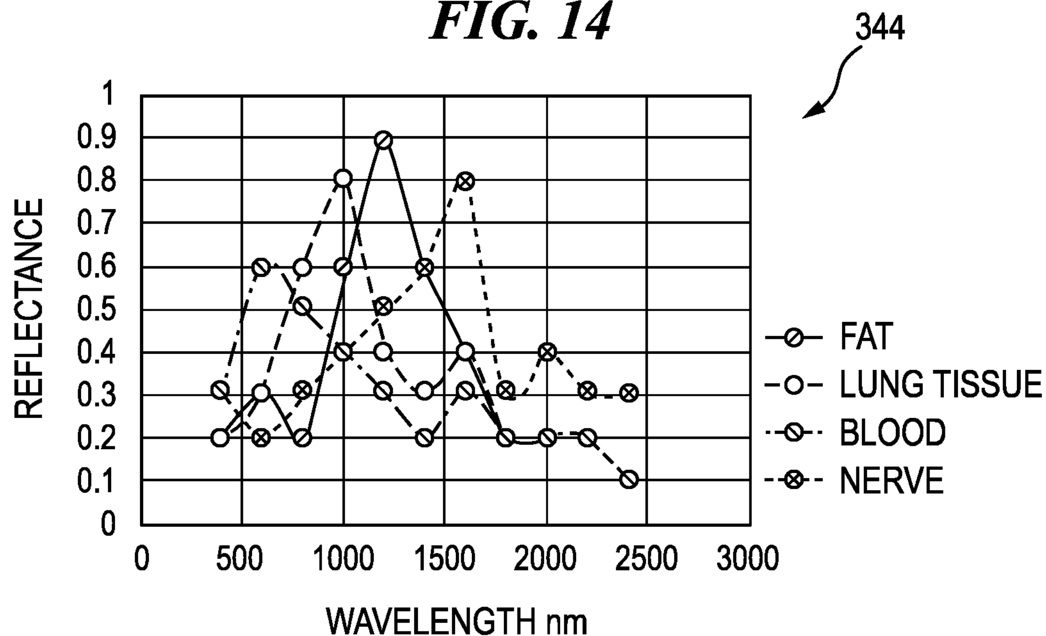
FIG. 14 is a graph depicting illustrative hyperspectral identifying signatures to differentiate a nerve from obscurants.

Tissues and/or structures can also be imaged or characterized according to their reflective characteristics, in addition to or in lieu of their absorptive characteristics described above with respect to FIG. 10 and FIG. 11, across the EMR wavelength spectrum. For example, FIG. 12, FIG. 13, and FIG. 14 illustrate various graphs of reflectance of different types of tissues or structures across different EMR wavelengths. FIG. 12 is a graphical representation 340 of an illustrative ureter signature versus obscurants. FIG. 13 is a graphical representation 342 of an illustrative artery signature versus obscurants. FIG. 14 is a graphical representation 344 of an illustrative nerve signature versus obscurants. The plots in FIG. 12, FIG. 13, and FIG. 14 represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

Select wavelengths for spectral imaging can be identified and utilized based on the anticipated critical structures and/or obscurants at a surgical site (e.g., "selective spectral" imaging). By utilizing selective spectral imaging, the amount of time required to obtain the spectral image can be minimized such that the information can be obtained in real-time and utilized intraoperatively. The wavelengths can be selected by a medical practitioner or by a control circuit based on input by a user, e.g., a medical practitioner. In certain instances, the wavelengths can be selected based on machine learning and/or big data accessible to the control circuit via, e.g., a cloud or surgical hub.

Figures 15, 16:
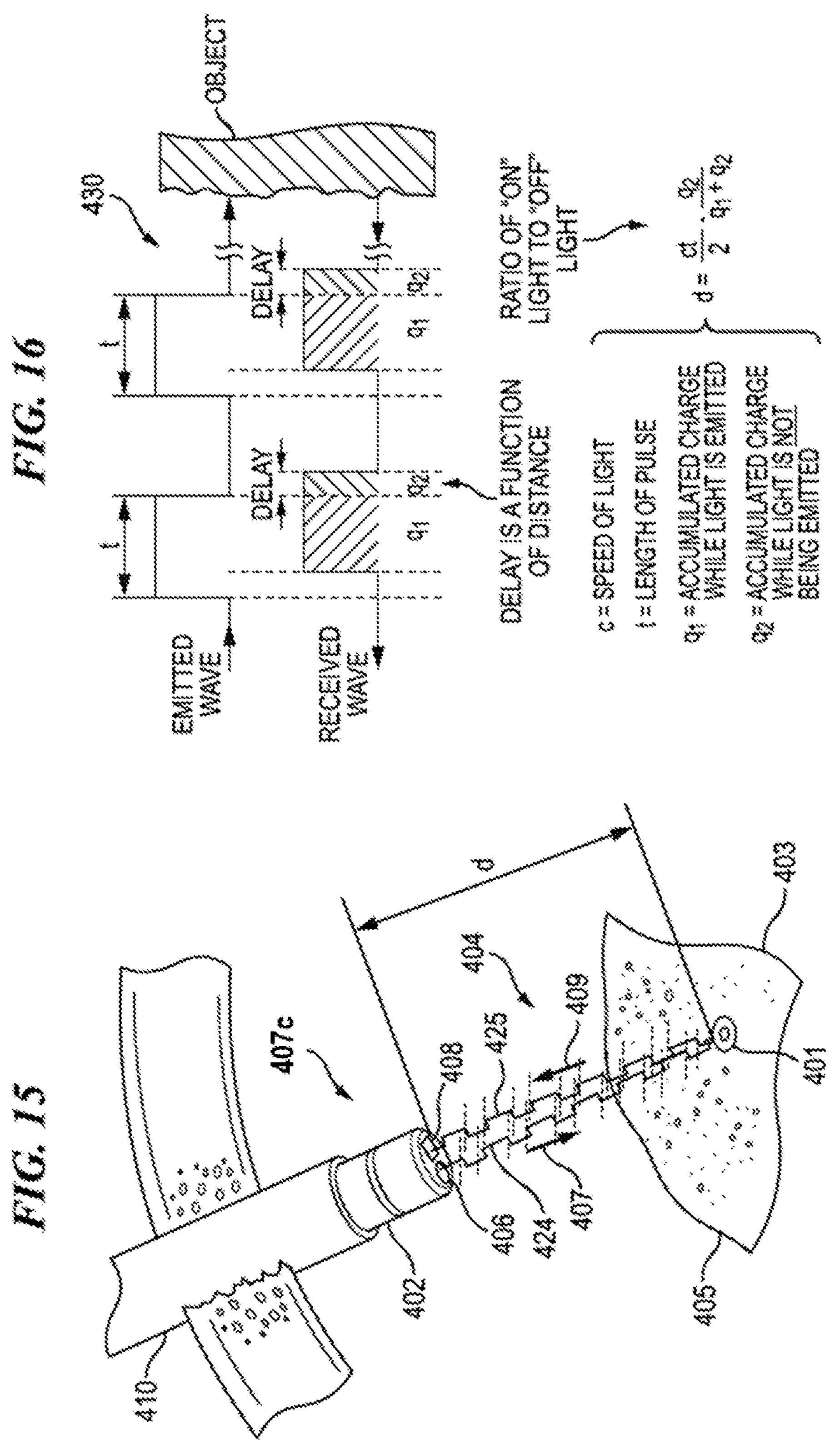
FIG. 15 is a schematic view of one embodiment of a near infrared (NIR) time-of-flight measurement system being utilized intraoperatively.
FIG. 16 shows a time-of-flight timing diagram for the system of FIG. 15.

FIG. 15 illustrates one embodiment of spectral imaging to tissue being utilized intraoperatively to measure a distance between a waveform emitter and a critical structure that is obscured by tissue. FIG. 15 shows an embodiment of a time-of-flight sensor system 404 utilizing waveforms 424, 425. The time-of-flight sensor system 404 can be incorporated into a surgical visualization system. e.g., as the sensor system 104 of the surgical visualization system 100 of FIG. 1. The time-of-flight sensor system 404 includes a waveform emitter 406 and a waveform receiver 408 on the same surgical device 402 (e.g., the emitter 106 and the receiver 108 on the same surgical device 102 of FIG. 1). The emitted wave 400 extends to a critical structure 401 (e.g., the critical structure 101 of FIG. 1) from the emitter 406, and the received wave 425 is reflected back to by the receiver 408 from the critical structure 401. The surgical device 402 in this illustrated embodiment is positioned through a trocar 410 that extends into a cavity 407*c* in a patient. Although the trocar 410 is used in this in this illustrated embodiment, other trocars or other access devices can be used, or no access device may be used.

The waveforms 424, 425 are configured to penetrate obscuring tissue 403, such as by having wavelengths in the NIR or SWIR spectrum of wavelengths. A spectral signal (e.g., hyperspectral, multispectral, or selective spectral) or a photoacoustic signal is emitted from the emitter 406, as shown by a first arrow 407 pointing distally, and can penetrate the tissue 403 in which the critical structure 401 is concealed. The emitted waveform 424 is reflected by the critical structure 401, as shown by a second arrow 409 pointing proximally. The received waveform 425 can be delayed due to a distance d between a distal end of the surgical device 402 and the critical structure 401. The waveforms 424, 425 can be selected to target the critical structure 401 within the tissue 403 based on the spectral signature of the critical structure 401, as described herein. The emitter 406 is configured to provide a binary signal on and off, as shown in FIG. 16, for example, which can be measured by the receiver 408.

Based on the delay between the emitted wave 424 and the received wave 425, the time-of-flight sensor system 404 is configured to determine the distance d. A time-of-flight timing diagram 430 for the emitter 406 and the receiver 408 of FIG. 15 is shown in FIG. 16. The delay is a function of the distance d and the distance d is given by:

$$d = \frac{ct}{2} \cdot \frac{q_2}{q_1 + q_2}$$

where c=the speed of light; t=length of pulse; $q_1$=accumulated charge while light is emitted; and $q_2$=accumulated charge while light is not being emitted.

The time-of-flight of the waveforms 424, 425 corresponds to the distance d in FIG. 15. In various instances, additional emitters/receivers and/or pulsing signals from the emitter 406 can be configured to emit a non-penetrating signal. The non-penetrating signal can be configured to determine the distance from the emitter 406 to the surface 405 of the obscuring tissue 403. In various instances, a depth of the critical structure 401 can be determined by:

$$d_A = d_w - d_t$$

where $d_A$=the depth of the critical structure 401; $d_w$=the distance from the emitter 406 to the critical structure 401 (d in FIG. 15); and $d_t$=the distance from the emitter 406 (on the distal end of the surgical device 402) to the surface 405 of the obscuring tissue 403.

Figure 17:
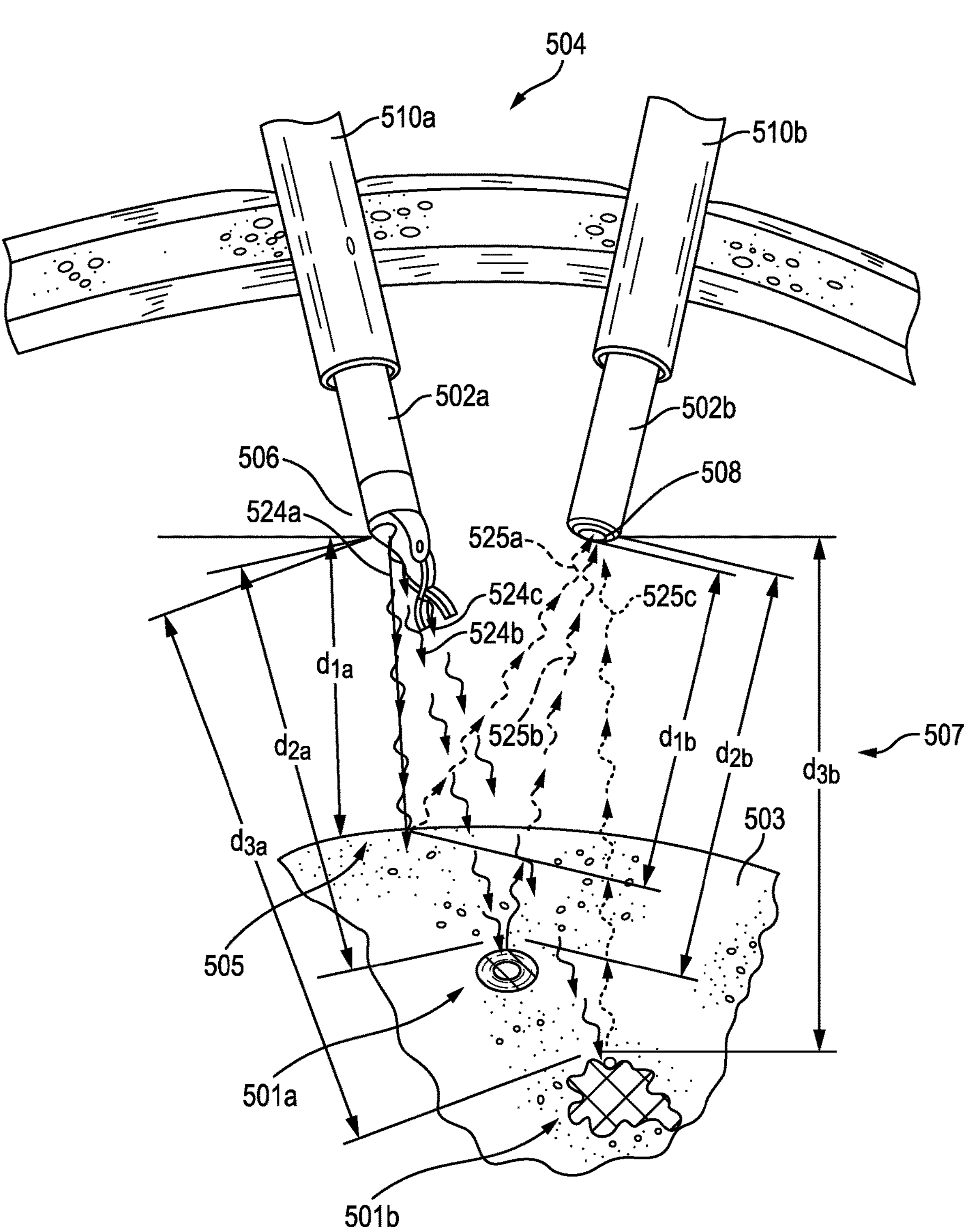
FIG. 17 is a schematic view of another embodiment of a near infrared (NIR) time-of-flight measurement system being utilized intraoperatively.

FIG. 17 illustrates another embodiment of a time-of-flight sensor system 504 utilizing waves 524*a*, 524*b*, 524*c*, 525*a*, 525*b*, 525*c* is shown. The time-of-flight sensor system 504 can be incorporated into a surgical visualization system. e.g., as the sensor system 104 of the surgical visualization system 100 of FIG. 1. The time-of-flight sensor system 504 includes a waveform emitter 506 and a waveform receiver 508 (e.g., the emitter 106 and the receiver 108 of FIG. 1). The waveform emitter 506 is positioned on a first surgical device 502*a* (e.g., the surgical device 102 of FIG. 1), and the waveform receiver 508 is positioned on a second surgical device 502*b*. The surgical devices 502*a*, 502*b* are positioned through first and second trocars 510*a*, 510*b*, respectively, which extend into a cavity 507 in a patient. Although the trocars 510*a*, 510*b* are used in this in this illustrated embodiment, other trocars or other access devices can be used, or no access device may be used. The emitted waves 524*a*, 524*b*, 524*c* extend toward a surgical site from the emitter 506, and the received waves 525*a*, 525*b*, 525*c* are reflected back to the receiver 508 from various structures and/or surfaces at the surgical site.

The different emitted waves 524*a*, 524*b*, 524*c* are configured to target different types of material at the surgical site. For example, the wave 524*a* targets obscuring tissue 503, the wave 524*b* targets a first critical structure 501*a* (e.g., the critical structure 101 of FIG. 1), which is a vessel in this illustrated embodiment, and the wave 524*c* targets a second critical structure 501*b* (e.g., the critical structure 101 of FIG. 1), which is a cancerous tumor in this illustrated embodiment. The wavelengths of the waves 524*a*, 524*b*, 524*c* can be in the visible light, NIR, or SWIR spectrum of wavelengths. For example, visible light can be reflected off a surface 505 of the tissue 503, and NIR and/or SWIR waveforms can penetrate the surface 505 of the tissue 503. In various aspects, as described herein, a spectral signal (e.g., hyperspectral, multispectral, or selective spectral) or a photoacoustic signal can be emitted from the emitter 506. The waves 524*b*, 524*c* can be selected to target the critical structures 501*a*, 501*b* within the tissue 503 based on the spectral signature of the critical structures 501*a*, 501*b*, as described herein. Photoacoustic imaging is further described in various U.S. patent applications, which are incorporated by reference herein in the present disclosure.

The emitted waves 524*a*, 524*b*, 524*c* are reflected off the targeted material, namely the surface 505, the first critical structure 501*a*, and the second structure 501*b*, respectively. The received waveforms 525*a*, 525*b*, 525*c* can be delayed due to distances $d_{1a}$, $d_{2a}$, $d_{3a}$, $d_{1b}$, $d_{2b}$, $d_{2e}$.

In the time-of-flight sensor system 504, in which the emitter 506 and the receiver 508 are independently positionable (e.g., on separate surgical devices 502*a*, 502*b* and/or controlled by separate robotic arms), the various distances $d_{1a}$, $d_{2a}$, $d_{3a}$, $d_{1b}$, $d_{2b}$, $d_{2c}$ can be calculated from the known position of the emitter 506 and the receiver 508. For example, the positions can be known when the surgical devices 502*a*, 502*b* are robotically-controlled. Knowledge of the positions of the emitter 506 and the receiver 508, as well as the time of the photon stream to target a certain tissue and the information received by the receiver 508 of that particular response can allow a determination of the distances $d_{1a}$, $d_{2a}$, $d_{3a}$, $d_{1b}$, $d_{2b}$, $d_{2c}$. In one aspect, the distance to the obscured critical structures 501*a*, 501*b* can be triangulated using penetrating wavelengths. Because the speed of light is constant for any wavelength of visible or invisible light, the time-of-flight sensor system 504 can determine the various distances.

In a view provided to the medical practitioner, such as on a display, the receiver 508 can be rotated such that a center of mass of the target structure in the resulting images remains constant, e.g., in a plane perpendicular to an axis of a select target structure 503, 501*a*, or 501*b*. Such an orientation can quickly communicate one or more relevant distances and/or perspectives with respect to the target structure. For example, as shown in FIG. 17, the surgical site is displayed from a viewpoint in which the critical structure 501*a* is perpendicular to the viewing plane (e.g., the vessel is oriented in/out of the page). Such an orientation can be default setting; however, the view can be rotated or otherwise adjusted by a medical practitioner. In certain instances, the medical practitioner can toggle between different surfaces and/or target structures that define the viewpoint of the surgical site provided by the imaging system.

As in this illustrated embodiment, the receiver 508 can be mounted on the trocar 510*b* (or other access device) through which the surgical device 502*b* is positioned. In other embodiments, the receiver 508 can be mounted on a separate robotic arm for which the three-dimensional position is known. In various instances, the receiver 508 can be mounted on a movable arm that is separate from a robotic surgical system that controls the surgical device 502*a* or can be mounted to an operating room (OR) table or fixture that is intraoperatively registerable to the robot coordinate plane. In such instances, the position of the emitter 506 and the receiver 508 can be registerable to the same coordinate plane such that the distances can be triangulated from outputs from the time-of-flight sensor system 504.

Combining time-of-flight sensor systems and near-infrared spectroscopy (NIRS), termed TOF-NIRS, which is capable of measuring the time-resolved profiles of NIR light with nanosecond resolution can be found in "Time-Of-Flight Near-Infrared Spectroscopy For Nondestructive Measurement Of Internal Quality In Grapefruit," Journal of the American Society for Horticultural Science, May 2013 vol. 138 no. 3 225-228, which is hereby incorporated by reference in its entirety.

Embodiments of visualization systems and aspects and uses thereof are described further in U.S. Pat. Pub. No. 2020/0015923 entitled "Surgical Visualization Platform" filed Sep. 11, 2018, U.S. Pat. Pub. No. 2020/0015900 entitled "Controlling An Emitter Assembly Pulse Sequence" filed Sep. 11, 2018, U.S. Pat. Pub. No. 2020/0015668 entitled "Singular EMR Source Emitter Assembly" filed Sep. 11, 2018, U.S. Pat. Pub. No. 2020/0015925 entitled "Combination Emitter And Camera Assembly" filed Sep. 11, 2018, U.S. Pat. Pub. No. 2020/00015899 entitled "Surgical Visualization With Proximity Tracking Features" filed Sep. 11, 2018, U.S. Pat. Pub. No. 2020/00015903 entitled "Surgical Visualization Of Multiple Targets" filed Sep. 11, 2018, U.S. Pat. No. 10,792,034 entitled "Visualization Of Surgical Devices" filed Sep. 11, 2018, U.S. Pat. Pub. No. 2020/0015897 entitled "Operative Communication Of Light" filed Sep. 11, 2018, U.S. Pat. Pub. No. 2020/0015924 entitled "Robotic Light Projection Tools" filed Sep. 11, 2018, U.S. Pat. Pub. No. 2020/0015898 entitled "Surgical Visualization Feedback System" filed Sep. 11, 2018, U.S. Pat. Pub. No. 2020/0015906 entitled "Surgical Visualization And Monitoring" filed Sep. 11, 2018, U.S. Pat. Pub. No. 2020/0015907 entitled "Integration Of Imaging Data" filed Sep. 11, 2018, U.S. Pat. No. 10,925,598 entitled "Robotically-Assisted Surgical Suturing Systems" filed Sep. 11, 2018, U.S. Pat. Pub. No. 2020/0015901 entitled "Safety Logic For Surgical Suturing Systems" filed Sep. 11, 2018, U.S. Pat. Pub. No. 2020/0015914 entitled "Robotic Systems With Separate Photoacoustic Receivers" filed Sep. 11, 2018, U.S. Pat. Pub. No. 2020/0015902 entitled "Force Sensor Through Structured Light Deflection" filed Sep. 11, 2018, U.S. Pat. Pub. No. 2019/0201136 entitled "Method Of Hub Communication" filed Dec. 4, 2018, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, U.S. patent application Ser. No. 16/729,807 entitled "Method Of Using Imaging Devices In Surgery" filed Dec. 30, 2019, U.S. patent application Ser. No. 17/493,913 entitled "Surgical Methods Using Fiducial Identification And Tracking" filed on Oct. 5, 2021, U.S. patent application Ser. No. 17/493,904 entitled "Surgical Methods Using Multi-Source Imaging" filed on Oct. 5, 2021, U.S. patent application Ser. No. 17/450,020 entitled "Methods And Systems For Controlling Cooperative Surgical Instruments" filed on Oct. 5, 2021, U.S. patent application Ser. No. 17/450,025 entitled "Methods And Systems For Controlling Cooperative Surgical Instruments With Variable Surgical Site Access Trajectories" filed on Oct. 5, 2021, U.S. patent application Ser. No. 17/450,027 entitled "Methods And Systems For Controlling Cooperative Surgical Instruments" filed on Oct. 5, 2021, and U.S. patent application Ser. No. 17/449,765 entitled "Cooperative Access" filed on Oct. 1, 2021, which are hereby incorporated by reference in their entireties.

Surgical Hubs

The various visualization or imaging systems described herein can be incorporated into a system that includes a surgical hub. In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more visualization systems that are used during performance of medical procedures. The surgical hubs provide a wide array of functionality to improve the outcomes of medical procedures. The data generated by the various surgical devices, visualization systems, and surgical hubs about the patient and the medical procedure may be transmitted to the cloud-based medical analytics system. This data may then be aggregated with similar data gathered from many other surgical hubs, visualization systems, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, visualization systems, and surgical instruments. Due to the interconnectedness of all of the aforementioned components, improvements in medical procedures and practices may be found that otherwise may not be found if the many components were not so interconnected.

Examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0201046 entitled "Method For Controlling Smart Energy Devices" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0201140 entitled "Surgical Hub Situational Awareness" filed Mar. 29, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0206555 entitled "Cloud-based Medical Analytics For Customization And Recommendations To A User" filed Mar. 29, 2018, and U.S. Pat. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

Figure 18:
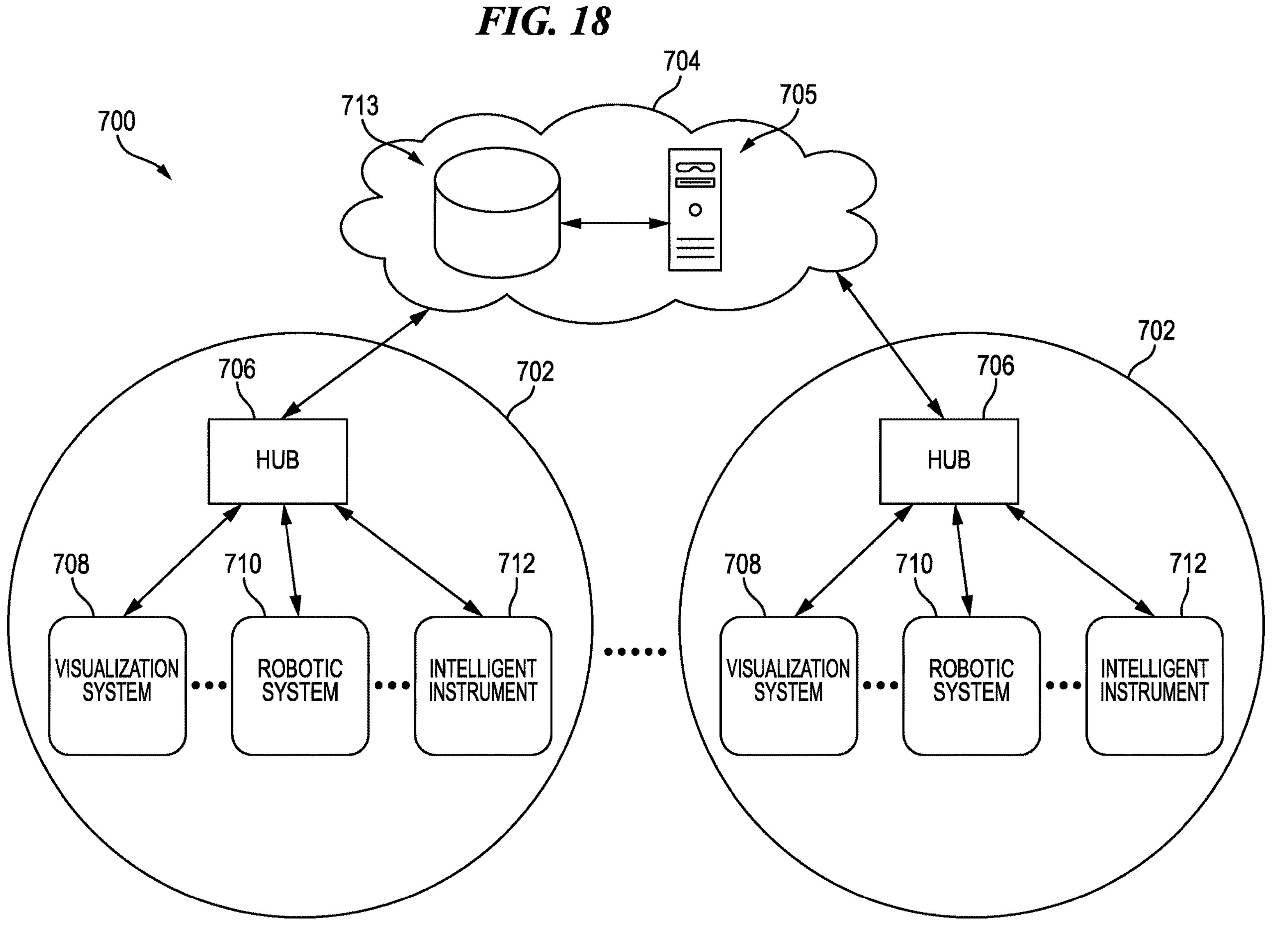
FIG. 18 is a schematic view of one embodiment of a computer-implemented interactive surgical system.

FIG. 18 illustrates one embodiment of a computer-implemented interactive surgical system 700 that includes one or more surgical systems 702 and a cloud-based system (e.g., a cloud 704 that can include a remote server 713 coupled to a storage device 705). Each surgical system 702 includes at least one surgical hub 706 in communication with the cloud 704. In one example, as illustrated in FIG. 18, the surgical system 702 includes a visualization system 708, a robotic system 710, and an intelligent (or "smart") surgical instrument 712, which are configured to communicate with one another and/or the hub 706. The intelligent surgical instrument 712 can include imaging device(s). The surgical system 702 can include an M number of hubs 706, an N number of visualization systems 708, an O number of robotic systems 710, and a P number of intelligent surgical instruments 712, where M, N, O, and P are integers greater than or equal to one that may or may not be equal to any one or more of each other. Various exemplary intelligent surgical instruments and robotic systems are described herein.

Data received by a surgical hub from a surgical visualization system can be used in any of a variety of ways. In an exemplary embodiment, the surgical hub can receive data from a surgical visualization system in use with a patient in a surgical setting, e.g., in use in an operating room during performance of a surgical procedure. The surgical hub can use the received data in any of one or more ways, as discussed herein.

The surgical hub can be configured to analyze received data in real time with use of the surgical visualization system and adjust control one or more of the surgical visualization system and/or one or more intelligent surgical instruments in use with the patient based on the analysis of the received data. Such adjustment can include, for example, adjusting one or operational control parameters of intelligent surgical instrument(s), causing one or more sensors of one or more intelligent surgical instruments to take a measurement to help gain an understanding of the patient's current physiological condition, and/or current operational status of an intelligent surgical instrument, and other adjustments. Controlling and adjusting operation of intelligent surgical instruments is discussed further below. Examples of operational control parameters of an intelligent surgical instrument include motor speed, cutting element speed, time, duration, level of energy application, and light emission. Examples of surgical hubs and of controlling and adjusting intelligent surgical instrument operation are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, and in U.S. patent application Ser. No. 17/068,857 entitled "Adaptive Responses From Smart Packaging Of Drug Delivery Absorbable Adjuncts" filed Oct. 13, 2020, U.S. patent application Ser. No. 17/068,858 entitled "Drug Administration Devices That Communicate With Surgical Hubs" filed Oct. 13, 2020, U.S. patent application Ser. No. 17/068,859 entitled "Controlling Operation Of Drug Administration Devices Using Surgical Hubs" filed Oct. 13, 2020, U.S. patent application Ser. No. 17/068,863 entitled "Patient Monitoring Using Drug Administration Devices" filed Oct. 13, 2020, U.S. patent application Ser. No. 17/068,865 entitled "Monitoring And Communicating Information Using Drug Administration Devices" filed Oct. 13, 2020, and U.S. patent application Ser. No. 17/068,867 entitled "Aggregating And Analyzing Drug Administration Data" filed Oct. 13, 2020, which are hereby incorporated by reference in their entireties.

The surgical hub can be configured to cause visualization of the received data to be provided in the surgical setting on a display so that a medical practitioner in the surgical setting can view the data and thereby receive an understanding of the operation of the imaging device(s) in use in the surgical setting. Such information provided via visualization can include text and/or images.

Figure 19:
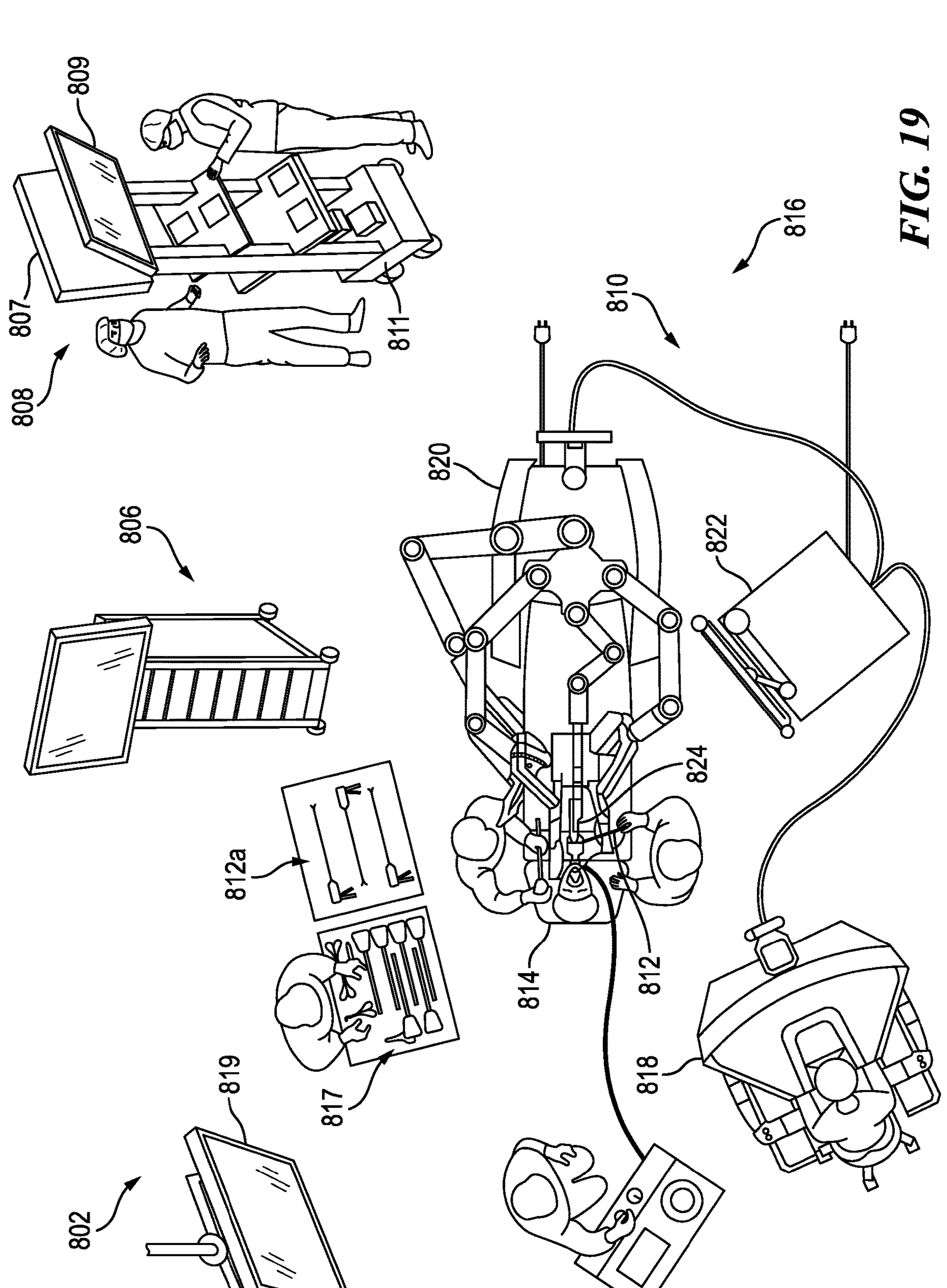
FIG. 19 is a schematic view of one embodiment a surgical system being used to perform a surgical procedure in an operating room.

FIG. 19 illustrates one embodiment of a surgical system 802 including a surgical hub 806 (e.g., the surgical hub 706 of FIG. 18 or other surgical hub described herein), a robotic surgical system 810 (e.g., the robotic surgical system 110 of FIG. 1 or other robotic surgical system herein), and a visualization system 808 (e.g., the visualization system 100 of FIG. 1 or other visualization system described herein). The surgical hub 806 can be in communication with a cloud, as discussed herein. FIG. 19 shows the surgical system 802 being used to perform a surgical procedure on a patient who is lying down on an operating table 814 in a surgical operating room 816. The robotic system 810 includes a surgeon's console 818, a patient side cart 820 (surgical robot), and a robotic system surgical hub 822. The robotic system surgical hub 822 is generally configured similar to the surgical hub 822 and can be in communication with a cloud. In some embodiments, the robotic system surgical hub 822 and the surgical hub 806 can be combined. The patient side cart 820 can manipulate an intelligent surgical tool 812 through a minimally invasive incision in the body of the patient while a medical practitioner, e.g., a surgeon, nurse, and/or other medical practitioner, views the surgical site through the surgeon's console 818. An image of the surgical site can be obtained by an imaging device 824 (e.g., the imaging device 120 of FIG. 1 or other imaging device described herein), which can be manipulated by the patient side cart 820 to orient the imaging device 824. The robotic system surgical hub 822 can be used to process the images of the surgical site for subsequent display to the surgeon through the surgeon's console 818.

A primary display 819 is positioned in the sterile field of the operating room 816 and is configured to be visible to an operator at the operating table 814. In addition, as in this illustrated embodiment, a visualization tower 811 can positioned outside the sterile field. The visualization tower 811 includes a first non-sterile display 807 and a second non-sterile display 809, which face away from each other. The visualization system 808, guided by the surgical hub 806, is configured to utilize the displays 807, 809, 819 to coordinate information flow to medical practitioners inside and outside the sterile field. For example, the surgical hub 806 can cause the visualization system 808 to display a snapshot and/or a video of a surgical site, as obtained by the imaging device 824, on one or both of the non-sterile displays 807, 809, while maintaining a live feed of the surgical site on the primary display 819. The snapshot and/or video on the non-sterile display 807 and/or 809 can permit a non-sterile medical practitioner to perform a diagnostic step relevant to the surgical procedure, for example.

The surgical hub 806 is configured to route a diagnostic input or feedback entered by a non-sterile medical practitioner at the visualization tower 811 to the primary display 819 within the sterile field, where it can be viewed by a sterile medical practitioner at the operating table 814. For example, the input can be in the form of a modification to the snapshot and/or video displayed on the non-sterile display 807 and/or 809, which can be routed to the primary display 819 by the surgical hub 806.

The surgical hub 806 is configured to coordinate information flow to a display of the intelligent surgical instrument 812, as is described in various U.S. Patent Applications that are incorporated by reference herein in the present disclosure. A diagnostic input or feedback entered by a non-sterile operator at the visualization tower 818 can be routed by the surgical hub 806 to the display 819 within the sterile field, where it can be viewed by the operator of the surgical instrument 812 and/or by other medical practitioner(s) in the sterile field.

The intelligent surgical instrument 812 and the imaging device 824, which is also an intelligent surgical tool, is being used with the patient in the surgical procedure as part of the surgical system 802. Other intelligent surgical instruments 812*a* that can be used in the surgical procedure, e.g., that can be removably coupled to the patient side cart 820 and be in communication with the robotic surgical system 810 and the surgical hub 806, are also shown in FIG. 19 as being available. Non-intelligent (or "dumb") surgical instruments 817, e.g., scissors, trocars, cannulas, scalpels, etc., that cannot be in communication with the robotic surgical system 810 and the surgical hub 806 are also shown in FIG. 19 as being available for use.

Operating Intelligent Surgical Instruments

An intelligent surgical device can have an algorithm stored thereon, e.g., in a memory thereof, configured to be executable on board the intelligent surgical device, e.g., by a processor thereof, to control operation of the intelligent surgical device. In some embodiments, instead of or in addition to being stored on the intelligent surgical device, the algorithm can be stored on a surgical hub, e.g., in a memory thereof, that is configured to communicate with the intelligent surgical device.

The algorithm is stored in the form of one or more sets of pluralities of data points defining and/or representing instructions, notifications, signals, etc. to control functions of the intelligent surgical device. In some embodiments, data gathered by the intelligent surgical device can be used by the intelligent surgical device, e.g., by a processor of the intelligent surgical device, to change at least one variable parameter of the algorithm. As discussed above, a surgical hub can be in communication with an intelligent surgical device, so data gathered by the intelligent surgical device can be communicated to the surgical hub and/or data gathered by another device in communication with the surgical hub can be communicated to the surgical hub, and data can be communicated from the surgical hub to the intelligent surgical device. Thus, instead of or in addition to the intelligent surgical device being configured to change a stored variable parameter, the surgical hub can be configured to communicate the changed at least one variable, alone or as part of the algorithm, to the intelligent surgical device and/or the surgical hub can communicate an instruction to the intelligent surgical device to change the at least one variable as determined by the surgical hub.

The at least one variable parameter is among the algorithm's data points, e.g., are included in instructions for operating the intelligent surgical device, and are thus each able to be changed by changing one or more of the stored pluralities of data points of the algorithm. After the at least one variable parameter has been changed, subsequent execution of the algorithm is according to the changed algorithm. As such, operation of the intelligent surgical device over time can be managed for a patient to increase the beneficial results use of the intelligent surgical device by taking into consideration actual situations of the patient and actual conditions and/or results of the surgical procedure in which the intelligent surgical device is being used. Changing the at least one variable parameter is automated to improve patient outcomes. Thus, the intelligent surgical device can be configured to provide personalized medicine based on the patient and the patient's surrounding conditions to provide a smart system. In a surgical setting in which the intelligent surgical device is being used during performance of a surgical procedure, automated changing of the at least one variable parameter may allow for the intelligent surgical device to be controlled based on data gathered during the performance of the surgical procedure, which may help ensure that the intelligent surgical device is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Figure 20:
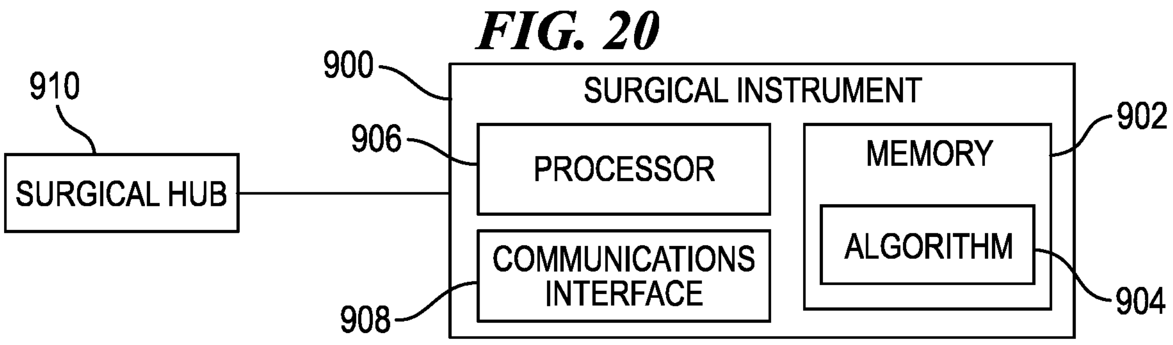
FIG. 20 is a schematic view of one embodiment of a surgical system including a smart surgical instrument and a surgical hub.

FIG. 20 illustrates one embodiment of an intelligent surgical instrument 900 including a memory 902 having an algorithm 904 stored therein that includes at least one variable parameter. The algorithm 904 can be a single algorithm or can include a plurality of algorithms, e.g., separate algorithms for different aspects of the surgical instrument's operation, where each algorithm includes at least one variable parameter. The intelligent surgical instrument 900 can be the surgical device 102 of FIG. 1, the imaging device 120 of FIG. 1, the surgical device 202 of FIG. 8, the imaging device 220 of FIG. 8, the surgical device 402 of FIG. 15, the surgical device 502*a* of FIG. 17, the surgical device 502*b* of FIG. 17, the surgical device 712 of FIG. 18, the surgical device 812 of FIG. 19, the imaging device 824 of FIG. 19, or other intelligent surgical instrument. The surgical instrument 900 also includes a processor 906 configured to execute the algorithm 904 to control operation of at least one aspect of the surgical instrument 900. To execute the algorithm 904, the processor 906 is configured to run a program stored in the memory 902 to access a plurality of data points of the algorithm 904 in the memory 902.

The surgical instrument 900 also includes a communications interface 908, e.g., a wireless transceiver or other wired or wireless communications interface, configured to communicate with another device, such as a surgical hub 910. The communications interface 908 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the surgical instrument 900 and/or data stored thereon and receiving instructions, such as from a doctor; a remote server regarding updates to software; a local, surgical hub server regarding updates to software; etc.

The surgical instrument 900 is simplified in FIG. 20 and can include additional components, e.g., a bus system, a handle, a elongate shaft having an end effector at a distal end thereof, a power source, etc. The processor 906 can also be configured to execute instructions stored in the memory 902 to control the device 900 generally, including other electrical components thereof such as the communications interface 908, an audio speaker, a user interface, etc.

The processor 906 is configured to change at least one variable parameter of the algorithm 904 such that a subsequent execution of the algorithm 904 will be in accordance with the changed at least one variable parameter. To change the at least one variable parameter of the algorithm 904, the processor 906 is configured to modify or update the data point(s) of the at least one variable parameter in the memory 902. The processor 906 can be configured to change the at least one variable parameter of the algorithm 904 in real time with use of the surgical device 900 during performance of a surgical procedure, which may accommodate real time conditions.

Additionally or alternatively to the processor 906 changing the at least one variable parameter, the processor 906 can be configured to change the algorithm 904 and/or at least one variable parameter of the algorithm 904 in response to an instruction received from the surgical hub 910. In some embodiments, the processor 906 is configured to change the at least one variable parameter only after communicating with the surgical hub 910 and receiving an instruction therefrom, which may help ensure coordinated action of the surgical instrument 900 with other aspects of the surgical procedure in which the surgical instrument 900 is being used.

In an exemplary embodiment, the processor 906 executes the algorithm 904 to control operation of the surgical instrument 900, changes the at least one variable parameter of the algorithm 904 based on real time data, and executes the algorithm 904 after changing the at least one variable parameter to control operation of the surgical instrument 900.

Figure 21:
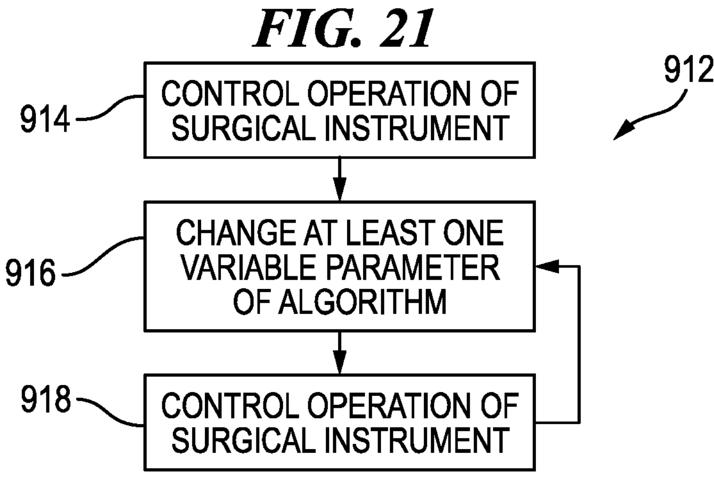
FIG. 21 is a flowchart showing a method of controlling the smart surgical instrument of FIG. 20.

FIG. 21 illustrates one embodiment of a method 912 of using of the surgical instrument 900 including a change of at least one variable parameter of the algorithm 904. The processor 906 controls 914 operation of the surgical instrument 900 by executing the algorithm 904 stored in the memory 902. Based on any of this subsequently known data and/or subsequently gathered data, the processor 906 changes 916 the at least one variable parameter of the algorithm 904 as discussed above. After changing the at least one variable parameter, the processor 906 controls 918 operation of the surgical instrument 900 by executing the algorithm 904, now with the changed at least one variable parameter. The processor 906 can change 916 the at least one variable parameter any number of times during performance of a surgical procedure, e.g., zero, one, two, three, etc. During any part of the method 912, the surgical instrument 900 can communicate with one or more computer systems, e.g., the surgical hub 910, a remote server such as a cloud server, etc., using the communications interface 908 to provide data thereto and/or receive instructions therefrom.

Situational Awareness

Operation of an intelligent surgical instrument can be altered based on situational awareness of the patient. The operation of the intelligent surgical instrument can be altered manually, such as by a user of the intelligent surgical instrument handling the instrument differently, providing a different input to the instrument, ceasing use of the instrument, etc. Additionally or alternatively, the operation of an intelligent surgical instrument can be changed automatically by an algorithm of the instrument being changed, e.g., by changing at least one variable parameter of the algorithm. As mentioned above, the algorithm can be adjusted automatically without user input requesting the change. Automating the adjustment during performance of a surgical procedure may help save time, may allow medical practitioners to focus on other aspects of the surgical procedure, and/or may ease the process of using the surgical instrument for a medical practitioner, which each may improve patient outcomes, such as by avoiding a critical structure, controlling the surgical instrument with consideration of a tissue type the instrument is being used on and/or near, etc.

The visualization systems described herein can be utilized as part of a situational awareness system that can be embodied or executed by a surgical hub, e.g., the surgical hub 706, the surgical hub 806, or other surgical hub described herein. In particular, characterizing, identifying, and/or visualizing surgical instruments (including their positions, orientations, and actions), tissues, structures, users, and/or other things located within the surgical field or the operating theater can provide contextual data that can be utilized by a situational awareness system to infer various information, such as a type of surgical procedure or a step thereof being performed, a type of tissue(s) and/or structure(s) being manipulated by a surgeon or other medical practitioner, and other information. The contextual data can then be utilized by the situational awareness system to provide alerts to a user, suggest subsequent steps or actions for the user to undertake, prepare surgical devices in anticipation for their use (e.g., activate an electrosurgical generator in anticipation of an electrosurgical instrument being utilized in a subsequent step of the surgical procedure, etc.), control operation of intelligent surgical instruments (e.g., customize surgical instrument operational parameters of an algorithm as discussed further below), and so on.

Although an intelligent surgical device including an algorithm that responds to sensed data, e.g., by having at least one variable parameter of the algorithm changed, can be an improvement over a "dumb" device that operates without accounting for sensed data, some sensed data can be incomplete or inconclusive when considered in isolation, e.g., without the context of the type of surgical procedure being performed or the type of tissue that is being operated on. Without knowing the procedural context (e.g., knowing the type of tissue being operated on or the type of procedure being performed), the algorithm may control the surgical device incorrectly or sub-optimally given the particular context-free sensed data. For example, the optimal manner for an algorithm to control a surgical instrument in response to a particular sensed parameter can vary according to the particular tissue type being operated on. This is due to the fact that different tissue types have different properties (e.g., resistance to tearing, ease of being cut, etc.) and thus respond differently to actions taken by surgical instruments. Therefore, it may be desirable for a surgical instrument to take different actions even when the same measurement for a particular parameter is sensed. As one example, the optimal manner in which to control a surgical stapler in response to the surgical stapler sensing an unexpectedly high force to close its end effector will vary depending upon whether the tissue type is susceptible or resistant to tearing. For tissues that are susceptible to tearing, such as lung tissue, the surgical instrument's control algorithm would optimally ramp down the motor in response to an unexpectedly high force to close to avoid tearing the tissue, e.g., change a variable parameter controlling motor speed or torque so the motor is slower. For tissues that are resistant to tearing, such as stomach tissue, the instrument's algorithm would optimally ramp up the motor in response to an unexpectedly high force to close to ensure that the end effector is clamped properly on the tissue, e.g., change a variable parameter controlling motor speed or torque so the motor is faster. Without knowing whether lung or stomach tissue has been clamped, the algorithm may be sub-optimally changed or not changed at all.

A surgical hub can be configured to derive information about a surgical procedure being performed based on data received from various data sources and then control modular devices accordingly. In other words, the surgical hub can be configured to infer information about the surgical procedure from received data and then control the modular devices operably coupled to the surgical hub based upon the inferred context of the surgical procedure. Modular devices can include any surgical device that is controllable by a situational awareness system, such as visualization system devices (e.g., a camera, a display screen, etc.), smart surgical instruments (e.g., an ultrasonic surgical instrument, an electrosurgical instrument, a surgical stapler, smoke evacuators, scopes, etc.). A modular device can include sensor(s) configured to detect parameters associated with a patient with which the device is being used and/or associated with the modular device itself.

The contextual information derived or inferred from the received data can include, for example, a type of surgical procedure being performed, a particular step of the surgical procedure that the surgeon (or other medical practitioner) is performing, a type of tissue being operated on, or a body cavity that is the subject of the surgical procedure. The situational awareness system of the surgical hub can be configured to derive the contextual information from the data received from the data sources in a variety of different ways. In an exemplary embodiment, the contextual information received by the situational awareness system of the surgical hub is associated with a particular control adjustment or set of control adjustments for one or more modular devices. The control adjustments each correspond to a variable parameter. In one example, the situational awareness system includes a pattern recognition system, or machine learning system (e.g., an artificial neural network), that has been trained on training data to correlate various inputs (e.g., data from databases, patient monitoring devices, and/or modular devices) to corresponding contextual information regarding a surgical procedure. In other words, a machine learning system can be trained to accurately derive contextual information regarding a surgical procedure from the provided inputs. In another example, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling at least one modular device. In another example, the situational awareness system includes a further machine learning system, lookup table, or other such system, which generates or retrieves one or more control adjustments for one or more modular devices when provided the contextual information as input.

A surgical hub including a situational awareness system may provide any number of benefits for a surgical system. One benefit includes improving the interpretation of sensed and collected data, which would in turn improve the processing accuracy and/or the usage of the data during the course of a surgical procedure. Another benefit is that the situational awareness system for the surgical hub may improve surgical procedure outcomes by allowing for adjustment of surgical instruments (and other modular devices) for the particular context of each surgical procedure (such as adjusting to different tissue types) and validating actions during a surgical procedure. Yet another benefit is that the situational awareness system may improve surgeon's and/or other medical practitioners' efficiency in performing surgical procedures by automatically suggesting next steps, providing data, and adjusting displays and other modular devices in the surgical theater according to the specific context of the procedure. Another benefit includes proactively and automatically controlling modular devices according to the particular step of the surgical procedure that is being performed to reduce the number of times that medical practitioners are required to interact with or control the surgical system during the course of a surgical procedure, such as by a situationally aware surgical hub proactively activating a generator to which an RF electrosurgical instrument is connected if it determines that a subsequent step of the procedure requires the use of the instrument. Proactively activating the energy source allows the instrument to be ready for use a soon as the preceding step of the procedure is completed.

For example, a situationally aware surgical hub can be configured to determine what type of tissue is being operated on. Therefore, when an unexpectedly high force to close a surgical instrument's end effector is detected, the situationally aware surgical hub can be configured to correctly ramp up or ramp down a motor of the surgical instrument for the type of tissue, e.g., by changing or causing change of at least one variable parameter of an algorithm for the surgical instrument regarding motor speed or torque.

For another example, a type of tissue being operated can affect adjustments that are made to compression rate and load thresholds of a surgical stapler for a particular tissue gap measurement. A situationally aware surgical hub can be configured to infer whether a surgical procedure being performed is a thoracic or an abdominal procedure, allowing the surgical hub to determine whether the tissue clamped by an end effector of the surgical stapler is lung tissue (for a thoracic procedure) or stomach tissue (for an abdominal procedure). The surgical hub can then be configured to cause adjustment of the compression rate and load thresholds of the surgical stapler appropriately for the type of tissue, e.g., by changing or causing change of at least one variable parameter of an algorithm for the surgical stapler regarding compression rate and load threshold.

As yet another example, a type of body cavity being operated in during an insufflation procedure can affect the function of a smoke evacuator. A situationally aware surgical hub can be configured to determine whether the surgical site is under pressure (by determining that the surgical procedure is utilizing insufflation) and determine the procedure type. As a procedure type is generally performed in a specific body cavity, the surgical hub can be configured to control a motor rate of the smoke evacuator appropriately for the body cavity being operated in, e.g., by changing or causing change of at least one variable parameter of an algorithm for the smoke evacuator regarding motor rate. Thus, a situationally aware surgical hub may provide a consistent amount of smoke evacuation for both thoracic and abdominal procedures.

As yet another example, a type of procedure being performed can affect the optimal energy level for an ultrasonic surgical instrument or radio frequency (RF) electrosurgical instrument to operate at. Arthroscopic procedures, for example, require higher energy levels because an end effector of the ultrasonic surgical instrument or RF electrosurgical instrument is immersed in fluid. A situationally aware surgical hub can be configured to determine whether the surgical procedure is an arthroscopic procedure. The surgical hub can be configured to adjust an RF power level or an ultrasonic amplitude of the generator (e.g., adjust energy level) to compensate for the fluid filled environment, e.g., by changing or causing change of at least one variable parameter of an algorithm for the instrument and/or a generator regarding energy level. Relatedly, a type of tissue being operated on can affect the optimal energy level for an ultrasonic surgical instrument or RF electrosurgical instrument to operate at. A situationally aware surgical hub can be configured to determine what type of surgical procedure is being performed and then customize the energy level for the ultrasonic surgical instrument or RF electrosurgical instrument, respectively, according to the expected tissue profile for the surgical procedure, e.g., by changing or causing change of at least one variable parameter of an algorithm for the instrument and/or a generator regarding energy level. Furthermore, a situationally aware surgical hub can be configured to adjust the energy level for the ultrasonic surgical instrument or RF electrosurgical instrument throughout the course of a surgical procedure, rather than just on a procedure-by-procedure basis. A situationally aware surgical hub can be configured to determine what step of the surgical procedure is being performed or will subsequently be performed and then update the control algorithm (s) for the generator and/or ultrasonic surgical instrument or RF electrosurgical instrument to set the energy level at a value appropriate for the expected tissue type according to the surgical procedure step.

As another example, a situationally aware surgical hub can be configured to determine whether the current or subsequent step of a surgical procedure requires a different view or degree of magnification on a display according to feature(s) at the surgical site that the surgeon and/or other medical practitioner is expected to need to view. The surgical hub can be configured to proactively change the displayed view (supplied by, e.g., an imaging device for a visualization system) accordingly so that the display automatically adjusts throughout the surgical procedure.

As yet another example, a situationally aware surgical hub can be configured to determine which step of a surgical procedure is being performed or will subsequently be performed and whether particular data or comparisons between data will be required for that step of the surgical procedure. The surgical hub can be configured to automatically call up data screens based upon the step of the surgical procedure being performed, without waiting for the surgeon or other medical practitioner to ask for the particular information.

As another example, a situationally aware surgical hub can be configured to determine whether a surgeon and/or other medical practitioner is making an error or otherwise deviating from an expected course of action during the course of a surgical procedure, e.g., as provided in a pre-operative surgical plan. For example, the surgical hub can be configured to determine a type of surgical procedure being performed, retrieve a corresponding list of steps or order of equipment usage (e.g., from a memory), and then compare the steps being performed or the equipment being used during the course of the surgical procedure to the expected steps or equipment for the type of surgical procedure that the surgical hub determined is being performed. The surgical hub can be configured to provide an alert (visual, audible, and/or tactile) indicating that an unexpected action is being performed or an unexpected device is being utilized at the particular step in the surgical procedure.

In certain instances, operation of a robotic surgical system, such as any of the various robotic surgical systems described herein, can be controlled by the surgical hub based on its situational awareness and/or feedback from the components thereof and/or based on information from a cloud (e.g., the cloud 713 of FIG. 18).

Embodiments of situational awareness systems and using situational awareness systems during performance of a surgical procedure are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019.

Surgical Procedures of the Lung

Various aspects of the devices, systems, and methods described herein may relate to a surgical procedure performed on a lung. For example, a lung resection, e.g., a lobectomy, is a surgical procedure in which all or part, e.g., one or more lobes, of a lung is removed. The purpose of performing a lung resection is to treat a damaged or diseased lung as a result of, for example, lung cancer, emphysema, or bronchiectasis.

During a lung resection, the lung or lungs are first deflated, and thereafter one or more incisions are made on the patient's side between the patient's ribs to reach the lungs laparoscopically. Surgical instruments, such as graspers and a laparoscope, are inserted through the incision. Once the infected or damaged area of the lung is identified, the area is dissected from the lung and removed from the one or more incisions. The dissected area and the one or more incisions can be closed, for example, with a surgical stapler or stitches.

Since the lung is deflated during surgery, the lung, or certain portions thereof, may need to be mobilized to allow the surgical instruments to reach the surgical site. This mobilization can be carried out by grasping the outer tissue layer of the lung with graspers and applying a force to the lung through the graspers. However, the pleura and parenchyma of the lung are very fragile and therefore can be easily ripped or torn under the applied force. Additionally, during mobilization, the graspers can cut off blood supply to one or more areas of the lung.

Further, a breathing tube is placed into the patient's airway to allow each lung to be separately inflated during surgery. Inflation of the lung can cause the lung to move and match pre-operative imaging and/or allow the surgeon to check for leaks at the dissected area(s). However, by inflating the whole lung, working space is lost around the lung due to the filling of the thoracic cavity. Additionally, inflating a whole lung can take time and does not guarantee easy leak detection if multiple portions of the lung are operated on during the surgical procedure.

Surgical Procedures of the Colon

Figure 22:
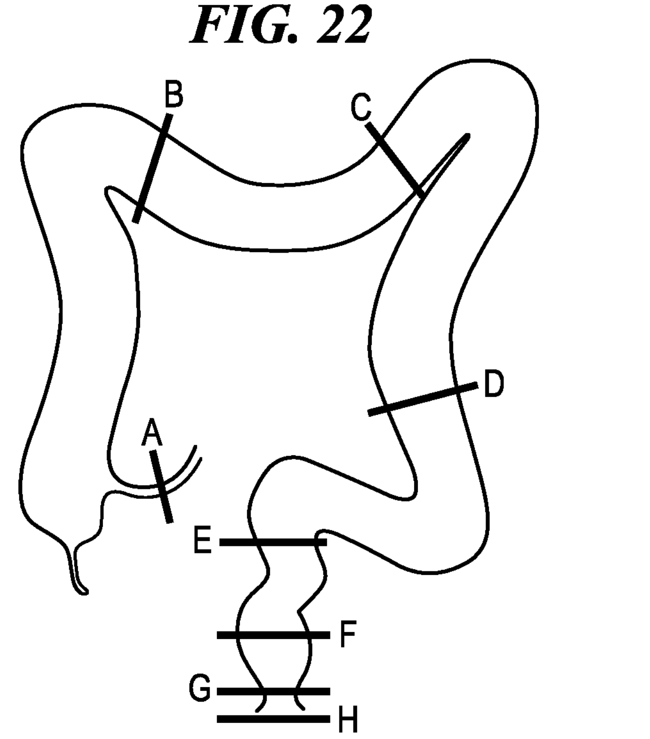
FIG. 22 is a schematic view of a colon illustrating major resections of the colon.

Various aspects of the devices, systems, and methods described herein may relate to a surgical procedure performed on a colon. For example, surgery is often the main treatment for early-stage colon cancers. The type of surgery used depends on the stage (extent) of the cancer, where it is in the colon, and the goal of the surgery. Some early colon cancers (stage 0 and some early stage I tumors) and most polyps can be removed during a colonoscopy. However, if the cancer has progressed, a local excision or colectomy may be required. A colectomy is surgery to remove all or part of the colon. In certain instances, nearby lymph nodes are also removed. If only part of the colon is removed, it's called a hemicolectomy, partial colectomy, or segmental resection in which the surgeon takes out the diseased part of the colon with a small segment of non-diseased colon on either side. Usually, about one-fourth to one-third of the colon is removed, depending on the size and location of the cancer. Major resections of the colon are illustrated in FIG. 22, in which A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total procto-colectomy. Once the resection is complete, the remaining intact sections of colon are then reattached.

A colectomy can be performed through an open colectomy, where a single incision through the abdominal wall is used to access the colon for separation and removal of the affected colon tissue, and through a laparoscopic-assisted colectomy. With a laparoscopic-assisted colectomy, the surgery is done through many smaller incisions with surgical instruments and a laparoscope passing through the small incisions to remove the entire colon or a part thereof. At the beginning of the procedure, the abdomen is inflated with gas, e.g., carbon dioxide, to provide a working space for the surgeon. The laparoscope transmits images inside the abdominal cavity, giving the surgeon a magnified view of the patient's internal organs on a monitor or other display. Several other cannulas are inserted to allow the surgeon to work inside and remove part(s) of the colon. Once the diseased parts of the colon are removed, the remaining ends of the colon are attached to each other, e.g., via staplers or stitches. The entire procedure may be completed through the cannulas or by lengthening one of the small cannula incisions.

During a laparoscopic-assisted colectomy procedure, it is often difficult to obtain an adequate operative field. Oftentimes, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

Further, multiple graspers are needed to position the tumor for removal from the colon. During dissection of the colon, the tumor should be placed under tension, which requires grasping and stretching the surrounding healthy tissue of the colon. However, the manipulating of the tissue surrounding the tumor can suffer from reduced blood flow and trauma due to the graspers placing a high grip force on the tissue. Additionally, during a colectomy, the transverse colon and upper descending colon may need to be mobilized to allow the healthy, good remaining colon to be brought down to connect to the rectal stump after the section of the colon containing the tumor is transected and removed.

After a colectomy, the remaining healthy portions of the colon must be reattached to one another to create a path for waste to leave the body. However, when using laparoscopic instruments to perform the colectomy, one single entry port may not have a large enough range of motion to move the one end of the colon to a connecting portion of the colon. As such, a second entry port is therefore needed to laparoscopically insert surgical instruments to help mobilize the colon in order to properly position the colon.

Surgical Procedures of the Stomach

Various aspects of the devices, systems, and methods described herein may relate to a surgical procedure performed on a stomach. For example, surgery is the most common treatment for stomach cancer. When surgery is required for stomach cancer, the goal is to remove the entire tumor as well as a good margin of healthy stomach tissue around the tumor. Different procedures can be used to remove stomach cancer. The type of procedure used depends on what part of the stomach the cancer is located and how far it has grown into nearby areas. For example, endoscopic mucosal resection (EMR) and endoscopic submucosal dissection (ESD) are procedures on the stomach can be used to treat some early-stage cancers. These procedures do not require a cut in the skin, but instead the surgeon passes an endoscope down the throat and into the stomach of the patient. Surgical tools (e.g., MEGADYNE™ Tissue Dissector or Electrosurgical Pencils) are then passed through the working channel of the endoscope to remove the tumor and some layers of the normal stomach wall below and around it.

Other surgical procedures performed on a stomach include a subtotal (partial) or a total gastrectomy that can be performed as an open procedure. e.g., surgical instruments are inserted through a large incision in the skin of the abdomen, or as a laparoscopic procedure, e.g., surgical instruments are inserted into the abdomen through several small cuts. For example, a laparoscopic gastrectomy procedure generally involves insufflation of the abdominal cavity with carbon dioxide gas to a pressure of around 15 millimeters of mercury (mm Hg). The abdominal wall is pierced and a straight tubular cannula or trocar, such as a cannula or trocar having a diameter in a range of about 5 mm to about 10 mm, is then inserted into the abdominal cavity. A laparoscope connected to an operating room monitor is used to visualize the operative field and is placed through one of the trocar(s). Laparoscopic surgical instruments are placed through two or more additional cannulas or trocars for manipulation by medical practitioner(s), e.g., surgeon and surgical assistant(s), to remove the desired portion(s) of the stomach.

In certain instances, laparoscopic and endoscopic cooperative surgery can be used to remove gastric tumors. This cooperative surgery typically involves introduction of an endoscope, e.g., a gastroscope, and laparoscopic trocars. A laparoscope and tissue manipulation and dissection surgical instruments are introduced through the trocar. The tumor location can be identified via the endoscope and a cutting element that is inserted into the working channel of the endoscope is then used for submucosal resection around the tumor. A laparoscopic dissection surgical instrument is then used for seromuscular dissection adjacent the tumor margins to create an incision through the stomach wall. The tumor is then pivoted through this incision from the intraluminal space, e.g., inside the stomach, to the extraluminal space, e.g., outside of the stomach. A laparoscopic surgical instrument, e.g., an endocutter, can be used to then complete the transection of the tumor from the stomach wall and seal the incision.

Surgical Procedures of the Intestine

Various aspects of the devices, systems, and methods described herein may relate to a surgical procedure performed on an intestine. For example, a duodenal mucosal resurfacing (DMR) procedure can be performed endoscopically to treat insulin-resistant metabolic diseases such as type 2 diabetes. The DMR procedure can be an effective treatment because it affects detection of food. The DMR procedure inhibits duodenum function such that food tends to be sensed deeper in the intestine than normal, e.g., sensed after passage through the duodenum (which is the first part of the small intestine). The patient's body thus senses sugar deeper in the intestine than is typical and thus reacts to the sugar later than is typical such that glycemic control can be improved. The irregular function of the duodenum changes the body's typical response to the food and, through nervous system and chemical signals, causes the body to adapt its response to the glucose level to increase insulin levels.

In the DMR procedure, the duodenal mucosa is lifted, such as with saline, and then the mucosa is ablated, e.g., using an ablation device advanced into the duodenum through a working channel of an endoscope. Lifting the mucosa before ablation helps protect the duodenum's outer layers from being damaged by the ablation. After the mucosa is ablated, the mucosa later regenerates. Examples of ablation devices are NeuWave™ ablation probes (available from Ethicon US LLC of Cincinnati, OH). Another example of an ablation device is the Hyblate catheter ablation probe (available from Hyblate Medical of Misgav, Israel). Another example of an ablation device is the Barxx™ HaloFlex (available from Medtronic of Minneapolis, MN).

Figure 23:
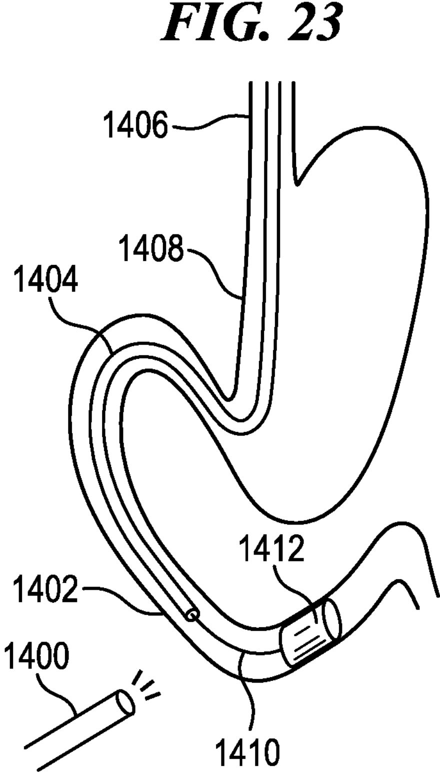
FIG. 23 is a perspective partial cross-sectional view of one embodiment of a duodenal mucosal resurfacing procedure.

FIG. 23 illustrates one embodiment of a DMR procedure. As shown in FIG. 23, a laparoscope 1400 is positioned external to a duodenum 1402 for external visualization of the duodenum 1402. An endoscope 1404 is advanced transorally through an esophagus 1406, through a stomach 1408, and into the duodenum 1402 for internal visualization of the duodenum 1402. An ablation device 1410 is advanced through a working channel of the endoscope 1404 to extend distally from the endoscope 1404 into the duodenum 1402. A balloon 1412 of the ablation device 1410 is shown expanded or inflated in FIG. 23. The expanded or inflated balloon 1412 can help center the ablation device's electrode so even circumferential ablating can occur before the ablation device 1410 is advanced and/or retracted to repeat ablation. Before the mucosa is ablated using the ablation device 1410, the duodenal mucosa is lifted, such as with saline. In some embodiments in addition to or instead of including the balloon 1412, the ablation device 1410 can be expandable/collapsible using an electrode array or basket configured to expand and collapse.

The laparoscope's external visualization of the duodenum 1402 can allow for thermal monitoring of the duodenum 1402, which may help ensure that the outer layers of the duodenum 1402 are not damaged by the ablation of the duodenal mucosa, such as by the duodenum being perforated. Various embodiments of thermal monitoring are discussed further, for example, below and in U.S. patent application Ser. No. 17/493,904 entitled "Surgical Methods Using Multi-Source Imaging" filed on Oct. 5, 2021. The endoscope 1404 and/or the ablation device 1410 can include a fiducial marker thereon that the laparoscope 1400 can be configured to visualize through the duodenum's tissue, e.g., by using invisible light, to help determine where the laparoscope 1400 should externally visualize the duodenum 1402 at a location where ablation occurs. Various embodiments of fiducial markers are discussed further, for example, below and in U.S. patent application Ser. No. 17/493,913 entitled "Surgical Methods Using Fiducial Identification And Tracking" filed on Oct. 5, 2021.

Intraluminal and Extraluminal Cooperation

Devices, systems, and methods for multi-source imaging provided herein may allow for intraluminal and extraluminal cooperation. In general, in intraluminal and extraluminal cooperation, a hollow organ or body lumen is visualized from an internal point of view (intraluminal visualization) and is visualized from an external point of view (extraluminal visualization). The intraluminal and extraluminal visualizations cooperate to provide a medical practitioner a more complete view of the hollow organ or body lumen at least at an area of interest thereof during performance of a surgical procedure than would be possible if only one of intraluminal and extraluminal was available. The medical practitioner may therefore be able to make more informed decisions in performing the surgical procedure and/or a controller (e.g., a controller of a surgical hub, a robotic surgical system, or other computer system) may be able to effect better control of surgical instruments and/or imaging devices.

A DMR procedure is an example of a surgical procedure that can include intraluminal and extraluminal cooperation. In a DMR procedure in which an endoscope and a laparoscope are used to visualize inside and outside a duodenum, respectively, blood flow intervention can be provided from the laparoscopic side of the duodenum, e.g., from outside the duodenum. The blood flow intervention may reinforce the endoluminal treatment to minimize mucosal recovery and prolong durability of the effects of the mucosal ablation. A surgical implant introduced laparoscopically can be configured to provide the blood flow intervention. The surgical implant can be configured to guide effects of the mucosal ablation and/or to marginalize blood supply to the duodenal region being ablated.

Reduced vascular flow can be measured, for example, by an infrared (IR) reading of a contrast agent, such as indocyanine green (ICG) or other contrast agent, introduced into the patient's blood. The laparoscope positioned outside the duodenum can be configured to visualize using IR (and possibly one or more additional visualization modalities, such as visual light, UV, etc.), thereby allowing the laparoscope to provide the IR reading of the contrast agent.

The reinforcement of the endoluminal treatment may be used to adapt the interconnection of the pancreas and the small intestine minorly to change gastrointestinal motility by allowing fatty acids to travel faster through the intestines. This laparoscopic adaption can be guided and collaborated with via small restrictions or increased structure opening or connections by the endoscope.

For another example, in a DMR procedure in which an endoscope and a laparoscope are used to visualize inside and outside a duodenum, an adjunct can be implanted at the duodenum to improve therapeutic effect of the DMR procedure. The adjunct is a medicant-eluting adjunct, which allows the adjunct to provide treatment to the duodenum from outside the duodenum to help the duodenum heal properly after the ablation. The medicant eluted by the adjunct can be configured to limit sensing in the duodenum and thereby prevent signal transmission of the sensing to another part of the patient's body. The mucosal ablation and the adjunct may thus each contribute to the DMR procedure's therapeutic effect.

The adjunct can releasably retain therein at least one medicant that can be selected from a large number of different medicants. Medicants include, but are not limited to, drugs or other agents included within, or associated with, the adjunct that have a desired functionality. Examples of medicants include antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+, Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). Examples of the growth factors further include erythropoietin (e.g., Darbepoetin, Epocept, Dynepo, Epomax, NeoRecormon, Silapo, and Retacrit).

Examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Examples of anesthetics include local anesthetics (e.g., Lidocaine, Benzocaine, and Ropivacaine) and general anesthetic.

Examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), *vinca* alkaloids gents that inhibit mitosis and microtubule formation (e.g., Vinblastine, Vincristine, Vindesine, Vinorelbine), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, examples of which include Hyaluronic acid/Carboxymethyl cellulose (seprafilm), Oxidized Regenerated Cellulose (Interceed), and Icodextrin 4% (Extraneal, Adept).

Figure 24:
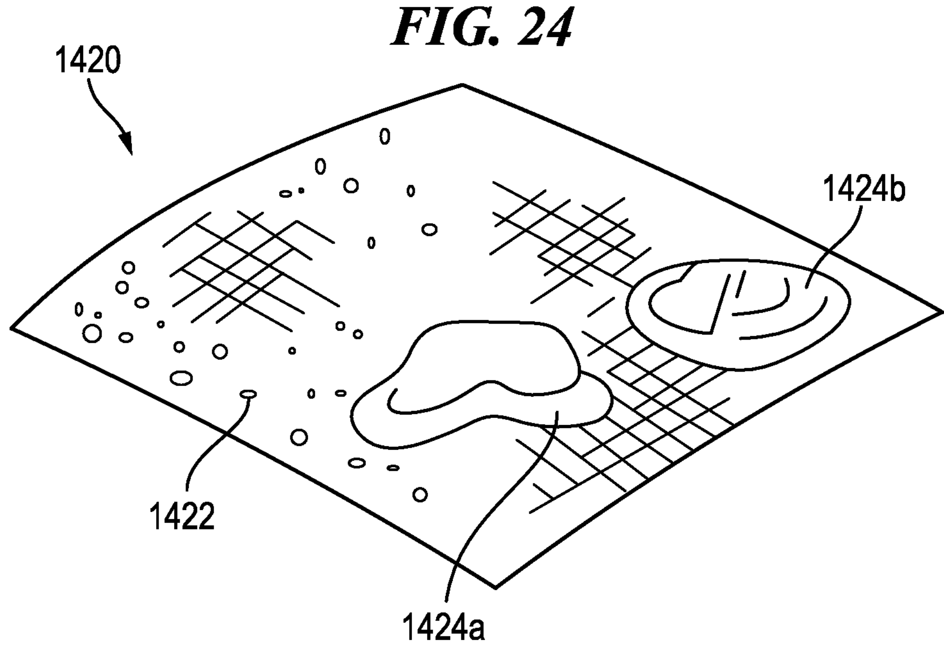
FIG. 24 is a perspective view of one embodiment of an adjunct.
Figures 25, 26:
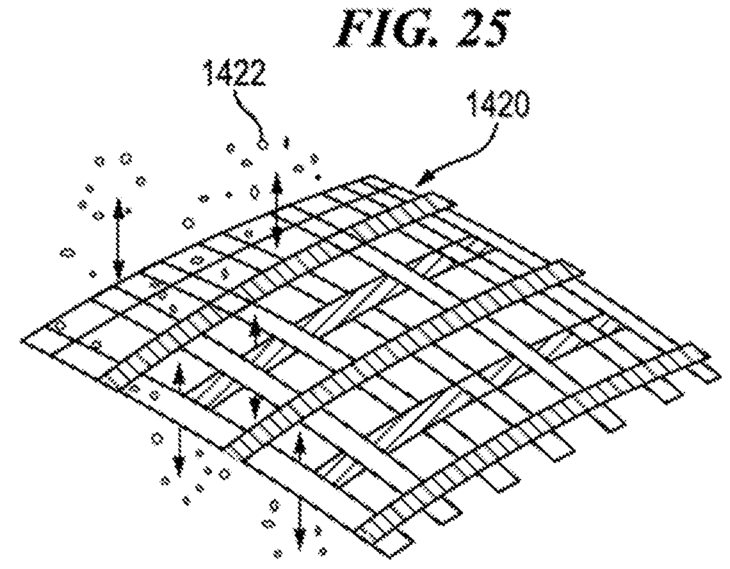
FIG. 25 is a perspective view of a portion of the adjunct of FIG. 24.
FIG. 26 is a perspective view of another embodiment of an adjunct.

FIG. 24 and FIG. 25 illustrate one embodiment of an adjunct 1420 having a medicant 1422 releasably retained therein. In this example, the adjunct 1420 is in the form of a sheet-like fiber woven mesh. As shown in FIG. 24, the tight fibers of the adjunct 1420 in its original configuration allow the medicant 1422 to be retained therein. When the adjunct 1420 is delivered at the treatment site, water and/or other agents, shown schematically as drops 1424*a*, 1424*b* in FIG. 24, are configured to cause the fibers to swell and elongate such that the distances between the fibers increase, as shown in FIG. 25. In this way, the medicant 1422 is released, as also shown in FIG. 25. A person skilled in the art will appreciate that the adjunct 1420 can be formed from different types of fibers. The fibers can have different absorption rates, density, direction, patterns, size, and other properties that are selected so as to provide desired tissue re-growth. While some regions of the adjunct can be configured to release at least one medicant so as to encourage tissue re-growth, one or more regions of the adjunct can be configured to release at least one medicant so as to discourage tissue re-growth.

FIG. 26 illustrates another embodiment of an adjunct 1426 in the form of a laminate including heterogeneous portions or layers having different degradation rates and incorporating different medicants. As shown, the adjunct 1426 includes a top layer or portion 1428 and a bottom layer or portion 1430 that have different degradation rates. Furthermore, each of the top and bottom portions 1428, 1430 can have various portions having degradation rates that vary in a distinct or continuous manner. The degradation rates can vary across the adjunct in a number of suitable ways that depend on a desired treatment effect to be provided by the adjunct. In some embodiments, an adjunct can have a single degradation rate instead of having different degradation rates.

In the embodiment of FIG. 26, the top portion 1428 of the adjunct 1426 includes two portions 1428*a*, 1428*b* having different degradation rates. The bottom portion 1430 includes two portions 1430*a*, 1430*b* having different degradation rates. Each of the portions can include a different medicant such that, as a portion degrades, a respective medicant is eluted or released. The degradation rates and distribution of the medicants within one or more of the portions 1428*a*, 1428*b*, 1430*a*, 1430*b* can further vary in a distinct or continuous manner such that the adjunct 1426 can provide an elution profile shown in a graph 1432 in FIG. 26. As shown, a central area 1434 of the adjunct 1426 centered around a mid-portion 1435 thereof has an increased elution rate of one or more medicants that peaks at the mid-portion 1435, whereas smaller amount of the medicant(s) is eluted from opposite sides of the adjunct 1426 along its length 1426L. The increased elution rate can be due to properties of the adjunct 1426 at the central area 1434 and the concentration of the medicants.

As also shown in FIG. 26, the adjunct 1426 is configured to release medicants in different elution profiles along the length 1426L thereof and along a width 1426W thereof. For example, the medicants can be released along the width 1426W as a bolus dose and along the length as a time-release dose. Release of one or more of the medicants can regulate release of at least one other of the medicants. However, the medicants can be released in any other manner, depending on a desired treatment to be delivered.

Figure 27:
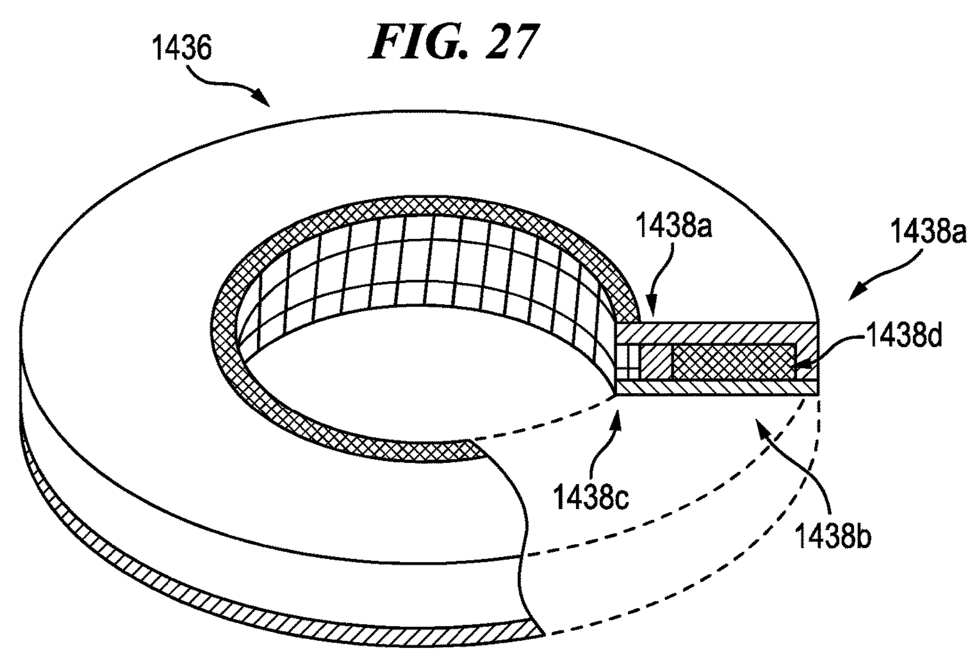
FIG. 27 is a perspective view of yet another embodiment of an adjunct.

The adjunct 1426 has a generally rectangular shape, which may facilitate its use with a linear stapler. Other adjuncts can have a different shape, such as to facilitate use thereof with a circular stapler. FIG. 27 illustrates such an implementation of an adjunct 1436 configured for use with a circular surgical stapler. The adjunct 1436 thus has a generally circular shape.

The adjunct 1436 in the illustrated implementation of FIG. 27 is formed from a plurality of fibers and includes a plurality of heterogeneous fiber lattice sections **1438*a*, 1438*b*, 1438*c*, 1438*d*. The first fiber lattice section 1438*a* is located on a top side and on an exterior side of the adjunct 1436 and is configured to discourage tissue growth by having a first medicant (not shown) releasably retained therein that is configured to discourage tissue growth, such as an anti-adhesion agent. The second fiber lattice section 1438*b* is located on a bottom side of the adjunct 1436 and is configured to encourage tissue growth by having a second medicant (not shown) releasably retained therein that is configured to encourage tissue growth, such as a growth factor. The third fiber lattice section 1438*c* is located on an interior side of the adjunct 1436 and is configured to facilitate hemostasis by having a third medicant (not shown) releasably retained therein that is configured to facilitate hemostasis, such as a hemostatic agent. The fourth fiber lattice section 1438*d* is located in an interior area of the adjunct 1436 and is configured to space apart the top and bottom sides of the adjunct 1436 to thereby space apart the tissue growth-encouraging and tissue growth-discouraging portions of the adjunct 1436. The fourth fiber lattice section 1438*d*** can have a fourth medicant (not shown) releasably retained therein. The fourth medicant can include, for example, an anti-adhesion agent or can include ORC and/or another hemostatic agent.

An adjunct can be implanted in a variety of ways. For example, the adjunct can be delivered using a surgical stapler introduced laparoscopically.

Various embodiments of adjuncts, implanting adjuncts, and/or surgical staplers are discussed further in U.S. Pat. Pub. No. 2018/0353174 filed Jun. 13, 2017 and entitled "Surgical Stapler with Controlled Healing," U.S. Pat. No. 10,569,071 entitled "Medicant Eluting Adjuncts And Methods Of Using Medicant Eluting Adjuncts" issued Feb. 25, 2020, U.S. Pat. No. 10,716,564 entitled "Stapling Adjunct Attachment" issued Jul. 21, 2020, U.S. Pat. Pub. No. 2013/0256377 entitled "Layer Comprising Deployable Attachment Members" filed Feb. 8, 2013, U.S. Pat. No. 8,393,514 entitled "Selectively Orientable Implantable Fastener Cartridge" filed Sep. 30, 2010, U.S. Pat. No. 8,317,070 entitled "Surgical Stapling Devices That Produce Formed Staples Having Different Lengths" filed Feb. 28, 2007, U.S. Pat. No. 7,143,925 entitled "Surgical Instrument Incorporating EAP Blocking Lockout Mechanism" filed Jun. 21, 2005, U.S. Pat. Pub. No. 2015/0134077 entitled "Sealing Materials For Use In Surgical Stapling" filed Nov. 8, 2013, U.S. Pat. Pub. No. 2015/0134076, entitled "Hybrid Adjunct Materials for Use in Surgical Stapling" filed on Nov. 8, 2013, U.S. Pat. Pub. No. 2015/0133996 entitled "Positively Charged Implantable Materials and Method of Forming the Same" filed on Nov. 8, 2013, U.S. Pat. Pub. No. 2015/0129634 entitled "Tissue Ingrowth Materials and Method of Using the Same" filed on Nov. 8, 2013, U.S. Pat. Pub. No. 2015/0133995 entitled "Hybrid Adjunct Materials for Use in Surgical Stapling" filed on Nov. 8, 2013, U.S. Pat. Pub. No. 2015/0272575 entitled "Surgical Instrument Comprising a Sensor System" and filed on Mar. 26, 2014, U.S. Pat. Pub. No. 2015/0351758 entitled "Adjunct Materials and Methods of Using Same in Surgical Methods for Tissue Sealing" filed on Jun. 10, 2014, U.S. Pat. Pub. No. 2013/0146643 entitled "Adhesive Film Laminate" filed Feb. 8, 2013, U.S. Pat. No. 7,601,118 entitled "Minimally Invasive Medical Implant And Insertion Device And Method For Using The Same" filed Sep. 12, 2007, and U.S. Pat. Pub. No. 2013/0221065 entitled "Fastener Cartridge Comprising A Releasably Attached Tissue Thickness Compensator" filed Feb. 8, 2013, which are each hereby incorporated by reference herein in their entireties.

In an exemplary embodiment, the adjunct is bioabsorbable and biocompatible. In such embodiments, the material (s) forming the adjunct can include bioabsorbable and biocompatible polymers, including homopolymers and copolymers. Examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl®, Vicryl Rapide™, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include poly (lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly (glycolic acid-co-caprolactone) (PCIJPGA) (e.g., Monocryl and Capgly), PDS/PGA/TMC (e.g., Biosyn), PDS/PLA, PGA/PCI/TMC/PLA (e.g., Caprosyn), and LPLA/DLPLA (e.g., Optima).

A location of where to implant the adjunct at the duodenum at a location that corresponds to where a mucosal ablation location inside the duodenum can be determined, for example, using a fiducial marker that is positioned inside the duodenum. The fiducial marker can be magnetic, thereby allowing the fiducial marker inside the duodenum to be located magnetically from outside the duodenum without naked eye or visible light visualization of the fiducial marker or the balloon to which the fiducial marker is attached. Various embodiments of using a fiducial marker to determine a location of an ablation device and/or a scope through which an ablation device has been advanced are discussed further below.

For example, in a DMR procedure in which an endoscope and a laparoscope are used to visualize inside and outside a duodenum, an implantable, nerve-stimulating sleeve or stent can be implanted at the duodenum around an outer diameter of the duodenum. The implanted sleeve or stent is configured to supply an electrical current to the duodenum to constrict blood supply and length effect of the ablation. The electrical current is configured to stimulate a nerve, such as a vague nerve, and thereby limit the sensing in the patient's gastrointestinal tract at the duodenum and thereby further prevent signal transmission of the sensing to another part of the patient's body to improve therapeutic effect of the DMR procedure. The nerve stimulation can be configured to limit the sensing in the patient's gastrointestinal tract and enhance the effect of mucosal ablation by overwhelming nerve signals or stimulating them out of sequence from eating. The mucosal ablation and the nerve stimulation may thus each contribute to the procedure's therapeutic effect.

The electrical current applied to an exterior of the duodenum may allow for a lower current to be used for ablation and/or for the ablation device to be more precisely positioned to ablate specific areas of the mucosa that are not subject to the stimulation. The electrical current can be delivered using an electrode attached to the sleeve or stent, for example.

The implanted sleeve or stent can be configured to deliver the electrical stimulation in response to a trigger event, such as detection of the patient eating.

The sleeve or stent can be configured to constrict around the entire circumference of the duodenum or only at specific areas around the circumference of the duodenum. The sleeve or stent constricting only at specific areas around the circumference of duodenum may minimize any constriction effect of the sleeve or stent around the duodenum, as the duodenum should not be squeezed shut or otherwise overly reduced in diameter to hinder normal intestinal function.

A location of where to implant the sleeve or stent outside the duodenum at a location that corresponds to a mucosal ablation location inside the duodenum can be determined, for example, using a fiducial marker that is positioned inside the duodenum. The fiducial marker can be magnetic, thereby allowing the fiducial marker inside the duodenum to be located magnetically from outside the duodenum without naked eye or visible light visualization of the fiducial marker or the element to which the fiducial marker is attached. Various embodiments of using a fiducial marker to determine a location of an ablation device and/or a scope through which an ablation device has been advanced are discussed further below.

The sleeve or stent can be bioabsorbable and biocompatible. In such embodiments, the material(s) forming the sleeve or stent can include bioabsorbable and biocompatible polymers, including homopolymers and copolymers.

Various embodiments of nerve stimulation, sensing and reacting to food ingestion, and implants configured to provide electrical stimulation of nerves are further described in U.S. Pat. No. 5,188,104 issued Feb. 23, 1993 and entitled "Treatment Of Eating Disorders By Nerve Stimulation," U.S. Pat. No. 5,231,988 issued Aug. 3, 1993 and entitled "Treatment Of Endocrine Disorders By Nerve Stimulation," U.S. Pat. No. 5,263,480 issued Nov. 23, 1993 and entitled "Treatment Of Eating Disorders By Nerve Stimulation," U.S. Pat. No. 5,540,730 issued Jul. 30, 1996 and entitled "Treatment Of Motility Disorders By Nerve Stimulation," U.S. Pat. No. 8,352,026 issued Jan. 8, 2013 and entitled "Implantable Pulse Generators And Methods For Selective Nerve Stimulation," U.S. Pat. No. 9,044,606 issued Jun. 2, 2015 and entitled "Methods And Devices For Activating Brown Adipose Tissue Using Electrical Energy," U.S. Pat. No. 10,092,738 issued Oct. 9, 2018 and entitled "Methods And Devices For Inhibiting Nerves When Activating Brown Adipose Tissue," U.S. Pat. Pub. No. 2009/0132018 filed Nov. 16, 2007 and entitled "Nerve Stimulation Patches And Methods For Stimulating Selected Nerves," U.S. Pat. Pub. No. 2008/0147146 filed Dec. 19, 2006 and entitled "Electrode Patch And Method For Neurostimulation," U.S. Pat. Pub. No. 2005/0277998 filed Jun. 7, 2005 and entitled "System And Method For Nerve Stimulation," U.S. Pat. Pub. No. 2006/0195153 filed Jan. 31, 2006 and entitled "System And Method For Selectively Stimulating Different Body Parts," U.S. Pat. Pub. No. 2007/0185541 filed Aug. 2, 2006 and entitled "Conductive Mesh For Neurostimulation," U.S. Pat. Pub. No. 2006/0195146 filed Jan. 31, 2006 and entitled "System And Method For Selectively Stimulating Different Body Parts," U.S. Pat. Pub. No. 2008/0132962 filed Dec. 1, 2006 and entitled "System And Method For Affecting Gastric Functions," U.S. Pat. Pub. No. 2008/0147146 filed Dec. 19, 2006 and entitled "Electrode Patch And Method For Neurostimulation," U.S. Pat. Pub. No. 2009/0157149 filed Dec. 14, 2007 and entitled "Dermatome Stimulation Devices And Methods," U.S. Pat. Pub. No. 2009/0149918 filed Dec. 6, 2007 and entitled "Implantable Antenna," U.S. Pat. Pub. No. 2009/0132018 filed Nov. 16, 2007 and entitled "Nerve Stimulation Patches And Methods For Stimulating Selected Nerves," U.S. Pat. Pub. No. 2010/0161001 filed Dec. 19, 2008 and entitled "Optimizing The Stimulus Current In A Surface Based Stimulation Device," U.S. Pat. Pub. No. 2010/0161005 filed Dec. 19, 2008 and entitled "Optimizing Stimulation Therapy Of An External Stimulating Device Based On Firing Of Action Potential In Target Nerve," U.S. Pat. Pub. No. 2010/0239648 filed Mar. 20, 2009 and entitled "Self-Locating, Multiple Application, And Multiple Location Medical Patch Systems And Methods Therefor," U.S. Pat. Pub. No. 2011/0094773 filed Oct. 26, 2009 and entitled "Offset Electrode," and U.S. Pat. No. 8,812,100 filed May 10, 2012 and entitled "A Device And Method For Self-Positioning Of A Stimulation Device To Activate Brown Adipose Tissue Depot In Supraclavicular Fossa Region," which are hereby each incorporated by reference in their entireties.

For yet another example, in a DMR procedure in which an endoscope and a laparoscope are used to visualize inside and outside a duodenum, an implantable suture can be implanted at the duodenum by being wrapped around an outer diameter of the duodenum. A location of where to wrap the suture outside the duodenum at a location that corresponds to a mucosal ablation location inside the duodenum can be determined, for example, using a fiducial marker on the ablation device, such as on a balloon of the ablation device or on another element thereof, that is positioned inside the duodenum. Various embodiments of using a fiducial marker to determine a location of an ablation device and/or a scope through which an ablation device has been advanced are discussed further below.

The suture is a medicant-eluting suture and/or an antimicrobial suture, which allows the suture to provide treatment to the duodenum from outside the duodenum to help the duodenum heal properly after the ablation. The medicant eluted by the medicant-eluting suture can be configured to limit sensing in the gastrointestinal tract at the duodenum and thereby prevent signal transmission of the sensing to another part of the patient's body. The mucosal ablation and the suture may thus each contribute to the DMR procedure's therapeutic effect.

The suture can be spiral-shaped so as to wrap helically around the duodenum. The spiral shape may minimize any constriction effect of the suture around the duodenum, as the duodenum should not be tied shut or otherwise overly reduced in diameter to hinder normal intestinal function.

In an exemplary embodiment, the suture is bioabsorbable and biocompatible. In such embodiments, the material(s) forming the suture can include bioabsorbable and biocompatible polymers, including homopolymers and copolymers.

Controlling Intelligent Surgical Instruments

Devices, systems, and methods for multi-source imaging provided herein may allow for controlling intelligent surgical instruments. An imaging system can be configured to visualize a surgical site during performance of a surgical procedure, as discussed herein. As also discussed herein, a surgical device such as an intelligent surgical instrument can be used in performing the surgical procedure. The surgical device can be in use at the surgical site while the imaging system is providing visualization, but the imaging system's view of the surgical device may be obstructed such that images gathered by the imaging system do not show the surgical device fully or at all.

The obstructed view can be caused, for example, by a tissue blocking the imaging system's view of the surgical device, such as if the imaging system is positioned on a first side of a tissue wall and the surgical device is positioned on a second, opposite side of the tissue wall. A DMR procedure is one example of a surgical procedure in which a surgical device can be positioned in a duodenum so as to be positioned on a first side of a tissue wall defined by the duodenum and an imaging device can be positioned outside the duodenum so as to be positioned on a second, opposite side of the tissue wall defined by the duodenum. A lung resection is another example of a surgical procedure in which a surgical device can be positioned in a lung so as to be positioned on a first side of a tissue wall defined by the lung and an imaging device can be positioned outside the lung so as to be positioned on a second, opposite side of the tissue wall defined by the lung. A colectomy is another example of a surgical procedure in which a surgical device can be positioned in a colon so as to be positioned on a first side of a tissue wall defined by the colon and an imaging device can be positioned outside the colon so as to be positioned on a second, opposite side of the tissue wall defined by the colon. EMR and ESD are other examples of a surgical procedure in which a surgical device can be positioned in a stomach so as to be positioned on a first side of a tissue wall defined by the stomach and an imaging device can be positioned outside the stomach so as to be positioned on a second, opposite side of the tissue wall defined by the stomach. Other surgical procedures can be performed in which a surgical device is positioned on a first side of a tissue wall and an imaging device can be positioned on a second, opposite side of the tissue wall.

A tissue can block the imaging system's view of the surgical device without the imaging system and the surgical device being on opposed sides of a tissue wall, such as if a tissue shifts position during performance of the surgical procedure and thus obstructs a view of the surgical device that the imaging system had before the tissue shift.

Regardless of the cause of the imaging system's obstructed view of the surgical device, the imaging system having an obstructed view of the surgical device may make control of the surgical device more difficult. A medical practitioner viewing images gathered by the imaging device and controlling the surgical device may not be able to make fully informed decisions about controlling the surgical device since the view of the surgical device is obstructed and may prevent the medical practitioner from seeing information that would otherwise factor into control of the surgical device. A controller at a surgical hub, a robotic surgical system, or other computer system controlling the surgical device may not be able to make fully informed decisions about controlling the surgical device since the view of the surgical device is obstructed and may prevent the controller from detecting information in the images that would otherwise factor into the controller's control of the surgical device.

An imaging device that has an obstructed view of an intelligent surgical device at a surgical site can be configured to visualize the surgical site and thereby monitor a parameter of a tissue engaged by the surgical device, such as by the surgical device ablating the tissue, grasping the tissue, stapling the tissue, or otherwise engaging the tissue. A controller, such as a controller at a surgical hub, a robotic surgical system, or other computer system, in communication with the imaging device and the surgical device can receive a signal from the imaging device regarding the monitored parameter. The controller can receive the signal directly from the imaging device or through one or more intermediary devices. As discussed above, an algorithm stored on board the intelligent surgical device or stored elsewhere can include one or more variable parameters. The controller can be configured to adjust at least one variable parameter of the algorithm based on the monitored parameter, as indicated by the received signal. The surgical device can thus be controlled based on information gathered by the imaging device despite the imaging device having an obstructed view of the surgical device.

The imaging device is configured to gather images, as discussed herein. The gathering of the images can be how the imaging device monitors the parameter such that the imaging device's normal operation can allow the parameter to be monitored. For example, as discussed above, an imaging device can be configured to gather images using invisible light. The invisible light can allow the imaging device to gather images on an opposite side of a tissue wall from where the imaging device is positioned because invisible light can "see" through the tissue wall. Thus, the imaging device being configured to gather images using invisible light can allow the imaging device to monitor the parameter.

As mentioned above, examples of variable parameters of a surgical device's algorithm include motor speed, motor torque, energy level, energy application duration, tissue compression rate, jaw closure rate, cutting element speed, load threshold, and other parameters. In an exemplary embodiment, the variable parameter(s) changed based on the monitored parameter can affect a movement of the surgical device, an electrode of the surgical device that is configured to deliver energy to the tissue (in embodiments in which the surgical device including an electrode, such as with an ablation device), a power level of the surgical device, or voltage control of the surgical device.

Figure 28:
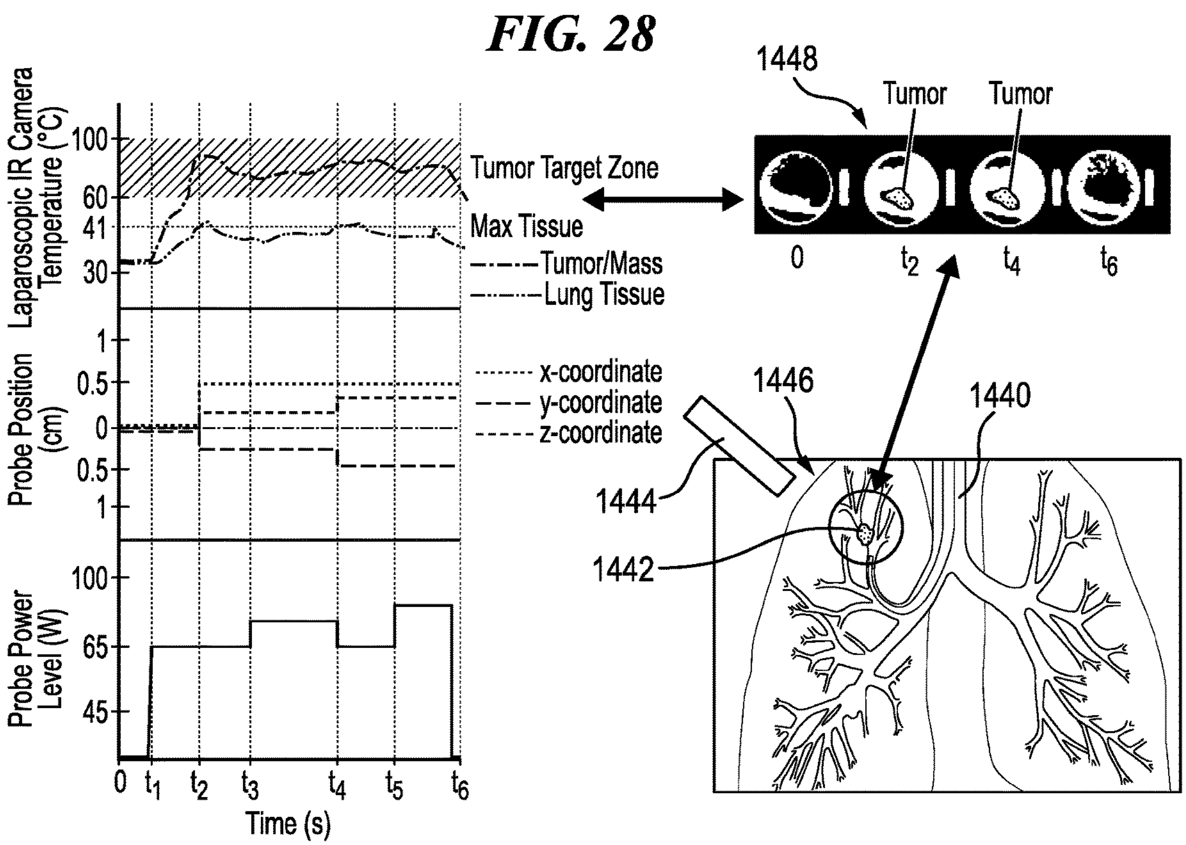
FIG. 28 illustrates one embodiment of controlling energy of an ablation device.

FIG. 28 illustrates one embodiment of an intelligent ablation device (ablation probe) 1440 positioned in a lung to apply energy to a tumor 1442 in the lung. An imaging device 1444 is positioned outside the lung and is configured to gather images using at least infrared light, e.g., by using an infrared (IR) camera. The ablation device 1440 is thus positioned on a first side of a tissue wall 1446 defined by the lung, and the imaging device 1444 is positioned on a second, opposite side of the tissue wall 1446 so as to have an obstructed view of the ablation device 1440. The imaging device's IR capability, however, lets the imaging device 1444 "see" inside the lung and gather internal lung temperature information. Infrared images 1448 gathered by the IR thermal camera at four times $t_0$, $t_2$, $t_4$, $t_6$ are shown in FIG. 28.

FIG. 28 also shows a graph indicating each of IR camera temperature (° C.), ablation probe 1440 position (cm), and ablation probe 1440 power level (W) versus time. As indicated in the graph, the IR thermal camera monitors the temperature of an area including the ablation device's ablation zone (e.g., an area of ablation that an ablation device 1440 can create), which includes the tumor 1442 and a margin area around the tumor 1442 within the ablation zone. The times in the graph include the four times $t_0$, $t_2$, $t_4$, $t_6$ for which IR images are shown.

The therapeutic temperature range for tissue ablation is in a range from about 60° C. to about 100° C. As shown in the graph, the power level is controlled based on the monitored temperature, as indicated in the gathered IR images, so the tumor 1442 is being ablated within the therapeutic temperature range from a time between times $t_1$ and $t_2$ to when energy application stops shortly before time $t_6$ between times $t_5$ and $t_6$. The temperature decreases from time $t_2$ and $t_3$, so at least one variable parameter of the ablation device's algorithm, such as the ablation device's power level and/or other variable parameter that affects energy delivered by an electrode of the ablation device 1440, is changed at time $t_3$ to increase power level and thus prevent the temperature from falling below about 60° C. The temperature increases from time $t_3$ and $t_4$, so the variable parameter(s) are changed again at time $t_4$ to reduce power level and thus prevent the temperature from rising above about 100° C. The temperature decreases again shortly before time $t_5$, so the variable parameter(s) are changed again at time $t_5$ to increase power level and thus prevent the temperature from falling below about 60° C. As discussed above, a controller at a surgical hub, a robotic surgical system, or other computer system can change the variable parameter(s) and can control execution of the algorithm.

Tissue being at a temperature up to about 41° C. can cause blood vessel dilation and increased blood perfusion and trigger a heat-shock response but have little long term effect. Tissue being at a temperature above about 41° C. makes the tissue susceptible to or causes the tissue to incur irreversible cell damage, where the higher the temperature, the greater the damage. As shown in the graph and as discussed further below, variable parameter(s) are also adjusted in this illustrated embodiment to keep the temperature of healthy, non-targeted lung tissue below about 41° C. while maintaining effective ablation of the tumor 1442.

FIG. 28 is described with respect to a lung, but similar control can be performed with respect to a surgical procedure performed at another hollow organ or body lumen. For example, in a DMR procedure, an intelligent surgical device, such as an intelligent ablation device, can be positioned inside a duodenum and an imaging device, such as a laparoscope, can be positioned outside the duodenum. The imaging device will thus have an obstructed view of the ablation device because of the duodenum's intervening tissue wall. The imaging device can be configured to gather images indicating temperature information, such as by imaging using at least infrared light, e.g., by using an IR camera, similar to that discussed above regarding the imaging device 1444 of FIG. 28. The intelligent ablation device can thus be controlled similar to that discussed above regarding the ablation device 1440 of FIG. 28 (and as discussed further below).

In some embodiments, an intelligent surgical device (e.g., an intelligent ablation device or other device) can include an electrode configured to apply energy to tissue, and tissue contact integrity can be sensed to control the surgical device's power level (e.g., by changing at least one variable parameter) in addition to another aspect of the surgical device such as power change tissue impedance threshold or other parameter controllable via one or more variable parameters. Such sensing may prevent electrode-tissue contact to less than an anticipated amount of contact given the electrode's known size and shape, may prevent a cross-sectional area of the electrode resulting in an inadvertent level of power density overly concentrating a cautery level being provided by the electrode, may prevent RF output voltages higher than necessary based on a tissue parameter such an impedance, and/or may reduce arcing potential.

An ablation device, for example the ablation device 1410 of FIG. 23 and other embodiments of ablation devices described herein, can be a bi-polar device that includes an inflatable or expandable member such as a balloon or basket and a plurality of electrodes (an electrode array) attached to the inflatable or expandable member that are configured to contact tissue at least when the inflatable or expandable member is inflated or expanded in a hollow organ or body lumen. A return can be provided with segmented electrodes contacting and applying pressure to an outer diameter of the hollow organ or body lumen. Various embodiments of return electrodes are discussed further below. Applying pressure to the outer diameter may help control a gap between the tissue intended to be ablated and adjacent tissue not intended to be ablated. Impedance measurements can be sampled until the return pressure/electrode contact area creates a desired impedance band. For example, in a DMR procedure, duodenal mucosa tissue to be ablated is lifted, such as with saline, to help protect the duodenum's outer layers, as discussed herein. Applying pressure to the duodenum's outer diameter may thus help control the gap between the target duodenal mucosa tissue intended to be ablated and the non-targeted duodenum outer layers not intended to be ablated. Additional saline can be added to adjust the gap as necessary. Additional saline also adjusts the tissue impedance. A pressure of the tissue can be sensed, for example, using a strain gauge, which may help adjustment of the applied outer pressure and/or of an amount and/or delivery rate of the saline.

The segmented electrodes can be a single return or an arc of returns, such as a 90° arc of returns. Various embodiments of return electrodes are discussed further below. A sizing tool can be used around a circumference of the hollow organ or body lumen to determine proper sizing and/or spacing for the return, which may allow for a full 360° ablation with a single ablation cycle.

Figures 29, 30, 31:
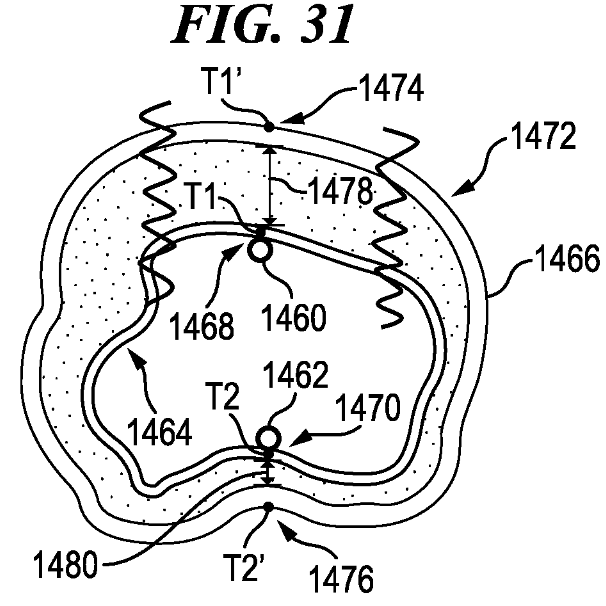
FIG. 29 is a schematic cross-sectional view of one embodiment of a flexible force probe pressing on a tissue wall in which a scope is positioned.
FIG. 30 is a perspective view of the probe and the scope of FIG. 29.
FIG. 31 is a schematic cross-sectional view of a body lumen having first and second electrodes positioned therein.

FIG. 29 and FIG. 30 illustrate one embodiment of a flexible force probe 1450 configured to apply force to a tissue wall 1452 from one side of the tissue wall 1452, which in this illustrated embodiment is outside of a body lumen 1454 in which a scope 1456 is positioned. The tissue lumen 1454 is not shown in FIG. 30. The flexible force probe 1450 includes an arm **1450*a* configured to serve as a return and to abut and press against the tissue wall 1452. The arm 1450*a* being flexible may allow the arm 1450*a* to conform to the shape of the tissue wall 1452. The internal path of the scope 1456 can be known within the lumen 1454, so the probe 1450 external to the lumen 1454 can follow the same spline path with the arm 1450*a* pressing on the tissue wall 1452. The arms 1450*a* can thus be in position to press against the exterior surface of the lumen 1454 where an ablation device introduced into the lumen 1454 ablates the lumen 1454 from inside the lumen 1454**.

In some embodiments, a ground pad can be applied to an exterior of tissue being ablated, e.g., an exterior surface of a duodenum or other tissue. The ground pad is configured to provide a current path to help contain ablation to the ablation zone. Ablation zone size is known for a particular ablation device. For example, NeuWave™ ablation probes (available from Ethicon US LLC of Cincinnati, OH) have an ablation zone of 2 cm. The ground pad can extend a length broader than an ablation device's ablation zone to help ensure that the entire ablation zone receives the benefit of the ground pad. A location of the ablation zone (e.g., location of the electrode providing the ablation zone) can be determined from outside the tissue being ablated from within by, for example, using multi-spectral imaging or using electromagnetic or RF monitoring, such as by using a laparoscope positioned outside a duodenum that is being ablated with an ablation device inside the duodenum. Various embodiments of determining a location of an ablation device and/or a scope in a hollow organ or body lumen are discussed further below.

In some embodiments, an intelligent surgical device (e.g., an intelligent ablation device or other device) can include an electrode configured to apply energy to tissue, and the surgical device's control algorithm can be adjusted (e.g., at least one variable parameter of the algorithm changed) to calibrate control of the electrode based on at least one measured tissue parameter before energy application begins. Energy may thus be more efficiently applied from a start of the ablation and/or the ablation may be completed more quickly and thus reduce chance of damaging any nearby tissue not intended to be ablated (non-targeted tissue).

In an exemplary embodiment, the tissue parameter used in calibrating control of the electrode includes at least one of tissue temperature, tissue impedance, and tissue thickness. As discussed herein, various surgical procedures can involve an imaging device being positioned outside a hollow organ or body lumen and a surgical device being positioned inside the hollow organ or body lumen such that the imaging device has an obstructed view of the surgical device. The imaging device can be configured to measure an exterior temperature of the hollow organ or body lumen, such as an external surface temperature being measured via one or more imaging modalities, and the surgical device can be configured to measure an interior temperature of the hollow organ or body lumen, such as an internal surface temperature being measured using a temperature sensor measuring. In many instances, the exterior and interior temperatures will not match due to, e.g., the tissue's thickness. In general, locations with a greater wall thickness will be cooler at the external surface than locations of the same tissue with less thickness. Additionally, thickness of a same tissue wall will usually vary between patients and can also vary for a tissue wall in a particular patient depending on where axially along the tissue and where circumferentially around the tissue that the thickness is measured.

Figure 32:
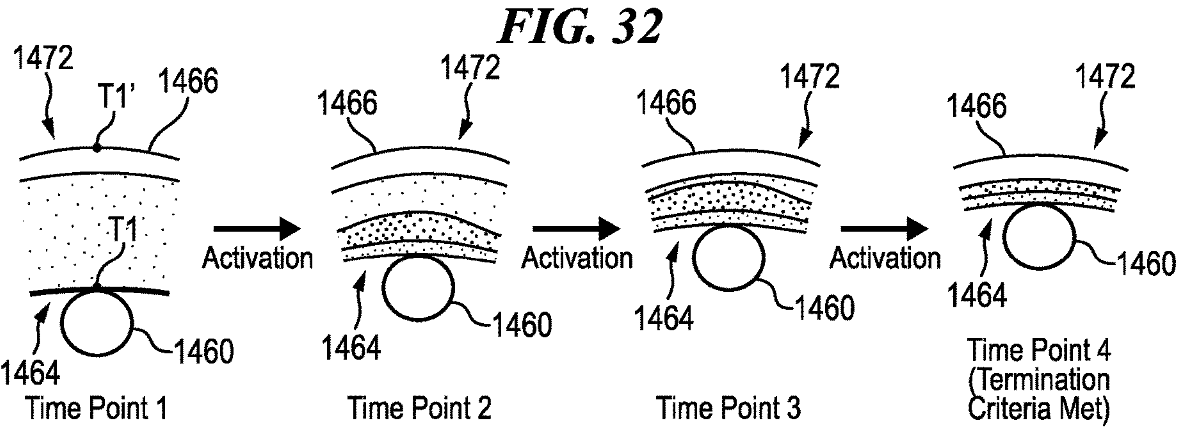
FIG. 32 is a view of the first electrode and a portion of the body lumen of FIG. 31 over four time points.
Figure 33:
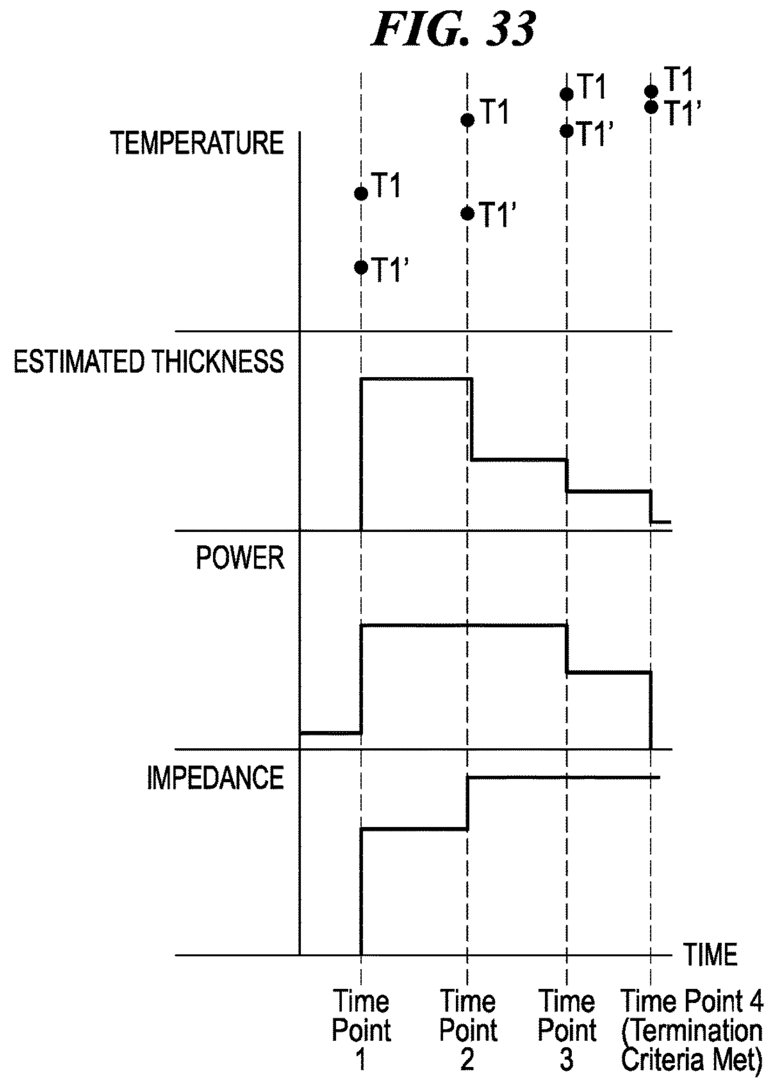
FIG. 33 is a graph showing temperature, estimated thickness, power, and impedance versus time including the four time points of FIG. 32.

FIG. 31, FIG. 32, and FIG. 33 illustrate one embodiment of using at least one measured tissue parameter in calibrating control of an electrode. In this illustrated embodiment, first and second electrodes 1460, 1462 are each positioned to contact an interior surface 1464 of a body lumen 1466. The body lumen 1466 can be, for example, a duodenum being ablated in a DMR procedure using an ablation device that includes the first and second electrodes 1460, 1462 attached to an inflatable or expandable member such as a balloon or a basket (see for example FIG. 23 and other embodiments of ablation devices described herein).

Each of the first and second electrodes 1460, 1462 is configured to monitor a temperature T1, T2 of the body's lumen's interior surface (also referred to herein as "internal surface") 1464, such as by each of the first and second electrodes 1460, 1462 including an integrated temperature sensor configured to monitor temperature or by each of the first and second electrodes 1460, 1462 including an integrated IR sensor configured to measure IR and emit an IR frequency signal that corresponds to a specific temperature. The temperature of the body's lumen's interior surface 1464 can thus be monitored at first and second locations 1468, 1470 around an interior circumference of the body lumen 1466 that correspond to the locations of the first and second electrodes 1460, 1462. A different number of electrodes can be used in other embodiments, with a corresponding different number of internal surface temperature measurements being gathered.

A temperature of an exterior surface (also referred to herein as "external surface") 1472 of the body lumen 1466 is also measured in this illustrated embodiment. The exterior surface 1472 temperature T1', T2' is monitored at first and second locations 1474, 1476 around an exterior circumference of the body lumen 1466 that correspond to the first and second locations 1468, 1470 around the interior circumference of the body lumen 1466 and thus to the locations of the first and second electrodes 1460, 1462. The external surface 1472 temperatures T1', T2' can be measured, for example, by using thermal imaging provided by an imaging device (not shown), such as a laparoscope, that is positioned outside of the body lumen 1466, by using a temperature sensor (e.g., a temperature sensor on a flexible force probe or other surgical device advanced through a working channel of the imaging device), or by using an IR sensor (e.g., an IR sensor on a flexible force probe or other surgical device advanced through a working channel of the imaging device). A different number of electrodes can be used in other embodiments, with a corresponding different number of external surface temperature measurements being gathered.

An increase in temperature at an exterior of a hollow organ or body lumen will be proportional to progress of denaturation in the underlying tissue wall. Measuring exterior tissue temperature may thus be tied to the ablation occurring underneath the location where exterior tissue temperature was measured. Accordingly, measuring internal and external temperatures T1, T2, T1', T2' of the body lumen 1466 allows a temperature gradient to be established from outside the serosal layer to the mucosal layer inside the lumen 1466 such that a temperature of each tissue layer can be established. The internal and external temperatures T1, T2, T1', T2' will typically not be the same before ablation begins because the mucosal layer acts as an insulator. The internal and external temperatures T1, T2, T1', T2' will typically not be the same during ablation since the internal surface 1464 of the body lumen 1466 is being heated. However, the exponential or polynomial relationship between internal and external temperature is consistent for a same tissue wall thickness and tissue type. Calibration of the internal and external temperatures T1, T2, T1', T2' before ablation begins can define a relationship between the first internal and external temperatures T1, T1' and the second internal and external temperatures T2, T2'. Measuring internal and external temperatures at more than one location around a hollow organ or body lumen's circumference, as in this illustrated embodiment, may help account for different in tissue wall thickness around the circumference.

Measuring the external temperature T1', T2' can help ensure that the heating of the internal surface 1464 of the body lumen 1466 does not overheat the tissue's outer layers that are unintended targets of the ablation. As discussed above, tissue being at a temperature above about 41° C. begins to make the tissue susceptible to or causes the tissue to incur irreversible cell damage. When the external temperature T1', T2' is determined to be above a predetermined maximum external temperature threshold, such as 41° C., 50° C., 60° C., 70° C., or other temperature, at least one variable parameter of the ablation control algorithm can be changed (e.g., by a controller of a surgical hub, a robotic surgical system, or other computer system), such as reducing a power level of the ablation device, to reduce heating of the tissue beyond the intended internal tissue. The predetermined maximum external temperature threshold being 60° C. or less may help prevent heating non-targeted tissue above 60° C., which as mentioned above is about the temperature that begins the therapeutic temperature range for tissue ablation. The predetermined maximum external temperature threshold being 50° C. or less can help prevent heating non-targeted tissue above 50° C., as about 50° C. is when irreversible tissue damage begins to occur. Changing the at least one variable parameter can be such that the electrode(s) associated with the at least one variable parameter continue delivering power but at a different level, e.g., in an effort to reduce temperature, increase temperature, or maintain temperature as desired, or can be such that power is turned off such that the electrode(s) associated with the at least one variable parameter stop delivering power, e.g., because the target tissue being treated has been heated to a predetermined goal temperature.

Measuring the internal temperature T1, T2 can help ensure that the heating of the internal surface 1464 of the body lumen 1466 is within the therapeutic temperature range for tissue ablation. As discussed above, the therapeutic temperature range for tissue ablation is in a range from about 60° C. to about 100° C. When the internal temperature T1, T2 is determined to be above a predetermined maximum internal temperature threshold, such as 100° C. or other temperature, or below a predetermined minimum internal temperature threshold, such as 60° C. or other temperature, at least one variable parameter of the ablation control algorithm can be changed (e.g., by a controller of a surgical hub, a robotic surgical system, or other computer system), such as changing a power level of the ablation device, to stop heating or to maintain effective heating of the tissue at the intended internal tissue.

The ablation device that includes the first and second electrodes 1460, 1462 can include a fiducial marker, such as a magnetic fiducial marker, thereon, such as on a balloon of the ablation device or on another element thereof. Various embodiments of fiducial markers are discussed further below. The external imaging device located outside the body lumen 1466 can be configured to detect the fiducial marker to help estimate tissue thickness 1478, 1480 at the first and second locations. The first thickness 1478 is greater than the second thickness 1480 in this illustrated embodiment. The imaging device has a known location, so the detected fiducial marker can allow a distance to be calculated therebetween that corresponds to the tissue thickness 1478, 1480. Tissue thickness is a variable that can be used to determine temperature. Tissue thickness is also a variable that can affect ablation device power output.

In embodiments in which infrared is used to measure internal and external temperatures T1, T2, T1', T2', each of the internal device (e.g., ablation device) and the external device (e.g., laparoscope) can include an IR emitter and receiver so that calibration can be achieved in both directions.

FIG. 31 and FIG. 32 illustrate a first tissue thickness 1478 between the first internal and external locations 1468, 1476 and a second tissue thickness 1480 between the second internal and external locations 1470, 1478 at time point 1. FIG. 32 shows a portion of FIG. 31, delineated by hash lines in FIG. 31, that includes the first electrode 1460, the first internal location 1468, and the first external location 1474 at each of four time points (time point 1, time point 2, time point 3, and time point 4) during performance of a surgical procedure.

FIG. 33 shows a graph where the first internal and external temperatures T1, T1', estimated tissue thickness based on the first and second estimated tissue thicknesses 1478, 1480, power level of the ablation device that includes the electrodes 1460, 1462, and tissue impedance are each plotted versus time, including each of the four times points of FIG. 32. As shown in the graph, power begins being supplied to the electrodes 1460, 1462 at time point 1 such that the electrodes 1460, 1462 begin delivering energy to the tissue at time point 1. Energy delivery continues through time points 2 and 3 and ends at time point 4. As shown in FIG. 32, the first tissue thickness 1478 decreases over time during ablation. The second tissue thickness 1480 also decreases during ablation. FIG. 32 also shows that the first internal and external temperatures T1, T1' increase over time during ablation even though power level of the ablation device is decreasing over time during ablation, as heating can provide a cumulative effect. The second internal and external temperatures T2, T2' also increase over time during ablation. FIG. 32 also shows that tissue impedance increases over time during ablation, as the tissue becomes hotter and the tissue's thickness decreases. At time point 4, ablation stops, e.g., power level goes to zero, in response to the first external temperature T1' being determined to be above the predetermined maximum external temperature threshold.

Controlling Pressure or Fluid Flow

Devices, systems, and methods for multi-source imaging provided herein may allow for controlling pressure or fluid flow. As discussed herein, a surgical procedure can include ablating tissue using an electrode. As also discussed herein, such a surgical procedure can include lifting tissue, such as by introduction of a fluid, before ablation to help protect non-targeted tissue from being overly heated. In an exemplary embodiment, electrode pressure on tissue and/or fluid expulsion can be controlled based on one of at least one monitored parameter of the tissue, a contact of the electrode with the tissue, and an aspect of energy transfer from the electrode to the tissue. Controlling a contact pressure of the electrode on tissue to which the electrode is delivering energy may help improve conductivity and/or may help direct energy of the electrode evenly and predictably. Controlling fluid expulsion, such as expulsion of saline or other fluid used to lift tissue before ablation, may help improve electrical coupling of the electrode with the tissue.

As discussed herein, an ablation device can be introduced into a duodenum or other anatomic structure through a working channel of a scope, e.g., an endoscope, and can expand radially outward once advanced distally beyond the scope. FIG. 23 illustrates one embodiment of such an ablation device 1410 that includes an electrode and an expandable or inflatable balloon 1412.

FIG. 34, FIG. 35, and FIG. 36 illustrate another embodiment of an ablation device 1490 configured to expand radially outward and compress radially inward. The ablation device 1490 includes a plurality of electrodes that are configured to move between a compressed configuration, which facilitates movement of the ablation device 1490 into and out of a patient, and an expanded configuration, which facilitates energy application to tissue by the electrodes that each contacts the tissue. The electrodes are spaced equally about a center of the device 1490 in this illustrated embodiment. FIG. 34 shows the ablation device 1490 in a compressed configuration in which the ablation device's electrodes extend linearly. FIG. 35 and FIG. 36 show the ablation device 1490 in an expanded configuration in which the electrodes are radially expanded. FIG. 36 also shows the ablation device 1490 advanced into position relative to a tumor 1492 through an endoscope 1494, with the electrodes expanded and advanced distally out of the ablation device's sheath 1496. The distal advancement of the electrodes out of the sheath 1496 (or proximal movement of the sheath 1496 relative to the electrodes) causes the electrodes to automatically radially expand. Correspondingly, proximal movement of the electrodes into the sheath 1496 (or distal movement of the sheath 1496 relative to the electrodes) causes the electrodes to automatically radially contract. In some embodiments, the sheath 1496 may be omitted such that movement of the electrodes into and out of the endoscope 1494 causes expansion and compression of the electrodes.

FIG. 37 illustrates another embodiment of an ablation device 1500 configured to expand radially outward. The ablation device 1500 includes a basket 1502 defined by a plurality of compressible strands or wires 1504 that each have an electrode 1506 attached thereto. The basket 1502, and thus the electrodes 1506 attached thereto, is configured to move between a compressed configuration, which facilitates movement of the ablation device 1500 into and out of a patient, and an expanded configuration, which facilitates energy application to tissue by the electrodes 1506 that each contacts tissue. The ablation device 1500 also includes a sheath 1508. Distal advancement of the basket 1502 out of the sheath 1508 (or proximal movement of the sheath 1508 relative to the basket 1502) causes the basket 1502 to automatically radially expand. Correspondingly, proximal movement of the basket 1502 into the sheath 1508 (or distal movement of the sheath 1508 relative to the basket 1502) causes the basket 1502 to automatically radially contract.

The ablation device 1500 includes an expandable or inflatable toroid balloon 1510. The balloon 1510 is configured to be pressurized with a fluid such as saline, which expands or inflates the balloon 1510. The balloon 1510 includes a plurality of sets of holes 1512, with each of the sets of holes 1512 being positioned adjacent to one of the electrodes 1506. Each of the sets includes four holes 1512 in this illustrated embodiment, but another number of holes is possible. The fluid pressurizing the balloon 1510 is configured to leak out of the holes 1512. The holes 1512 are small, e.g., smaller than the electrodes 1506, such that the fluid is configured to leak slowly out of the holes 1512. The holes 1512 face radially outward similar to the electrodes 1506 that are configured to contact and press against tissue such that the holes 1512 are similarly configured to abut the tissue. The fluid leaked out of the holes 1512 can thus be directed toward the tissue. The fluid that pressurizes the balloon 1510 can be introduced into the balloon 1510 by, for example, being passed into one or more of the strands or wires 1504 and then into the balloon 1510. In embodiments in which the fluid is a liquid, the balloon 1510 can include an insulator between the electrodes 1506 and a fluid chamber of the balloon 1510 that contains the fluid therein. The insulator may help minimize an amount of the balloon 1510 that becomes a heat sink.

The ablation device 1500 includes first and second flexible suction tubes 1514, 1516. The first suction tube 1514 is positioned distal to the second suction tube 1516. Each of the suction tubes 1514, 1516 includes a distal head **1514*h*, 1516*h* having a plurality of openings formed therein through which suction can be provided in a proximal direction into their respective tubes 1514, 1516. The first head 1514*h* and the second head 1516*h* act as weights of the first and second tubes 1514, 1516, respectively, such that gravity pulls the heads 1514*h*, 1516*h* in a same direction, which is a downward direction in the view of FIG. 37. Gravity will also pull fluid within a hollow organ or body lumen in which the ablation device 1500 is located such that the heads 1514*h*, 1516*h* will be pulled in a direction in which the fluid will tend to collect, thereby maximizing suctioning away of the fluid through the suction tubes 1514, 1516**.

As discussed herein, power provided to an ablation device's electrode configured to contact and delver energy tissue can be adjustable. In embodiments in which the ablation device is expandable/compressible, such as the ablation device 1410 of FIG. 23, the ablation device 1490 of FIG. 34 to FIG. 36, the ablation device 1500 of FIG. 37, and other ablation devices, the expansion/compression of the ablation device can be correlated to the power. In this way, the expansion/compression of the ablation device can be controlled based on the amount of power being provided to the ablation device's electrode (which may include a single electrode or a plurality of electrodes), e.g., by adjusting a variable parameter of the algorithm for expansion/compression of the ablation device based on a variable parameter of the control algorithm for the power. Correlating the expansion/compression of the ablation device to the power may help improve control of the cautery and a depth of the cautery in tissue even in locations on the tissue where electrical conductivity is variable.

As discussed herein, the ablation device can be configured to expand automatically when advanced distally out of a containment mechanism, such as a sheath or scope, and can be configured to compress when retracted proximally into the containment mechanism. An amount that the ablation device is advanced distally out of the containment mechanism can thus affect an amount of the ablation device's expansion, as the containment mechanism will constrain the expandable portion of the ablation device that is contained within the containment mechanism. An amount of pressure an electrode on the expandable portion of the ablation device applies to tissue can thus also be affected by an amount that the ablation device is advanced distally out of the containment mechanism since less than full expansion corresponds to less electrode pressure. Similarly, an amount that the ablation device is retracted proximally into of the containment mechanism can thus affect an amount of the ablation device's compression, as the containment mechanism will constrain the compressible portion of the ablation device that is contained within the containment mechanism. An amount of pressure an electrode on the expandable portion of the ablation device applies to tissue can thus also be affected by an amount that the ablation device is retracted proximally into the containment mechanism since less retraction corresponds to more electrode pressure.

As discussed herein, a surgical device such as an ablation device can be controlled by a controller of a surgical hub, a robotic surgical system, or other computer system, such as by retracting/advancing the ablation device according to at least one variable parameter of the ablation device's algorithm, such as a variable parameter corresponding to an amount of retraction/advancement (e.g., 0% advancement, 10% advancement, 25% advancement, 50% advancement, 74% advancement, 100% advancement, etc.), a variable parameter corresponding to a rate of advancement, and/or a variable parameter corresponding to a rate of retraction. The ablation device's position relative to the containment mechanism can be controlled by the controller controlling an amount that the ablation device is advanced distally out of the containment mechanism or retracted proximally into the containment mechanism, thereby also controlling an amount of the ablation device's electrode pressure on tissue. The expansion/compression of the ablation device can be correlated to the power provided to an ablation device's electrode by the variable parameter for amount of advancement/retraction being adjusted based on the current value of the variable parameter for power. For example, a fixed relationship can be preset between the variable parameter for the amount of retraction/advancement and the variable parameter for power such that in response to the variable parameter for power increasing or decreasing, the variable parameter for the amount of retraction/advancement correspondingly increases or decreases.

In some embodiments in which an ablation device is used in a surgical procedure, fluid expulsion can be controlled. In an exemplary embodiment, the fluid is saline. Controlling fluid expulsion may help improve electrical coupling of tissue and the ablation device's electrode (which can be a single electrode or a plurality of electrodes). Controlling fluid expulsion can include controlling a flow rate of the fluid and/or a salinity (hypotonic or hypertonic) of the fluid, e.g., by adjusting at least one variable parameter. Delivery of the fluid can be accomplished using two separate fluid feeds each for a different fluid. The two feeds can be combined in any manner desired depending on a desired salt content to improve conductivity or salt content. For example, a first fluid feed can be for a high salinity saline, and a second, separate fluid feed can be for distilled water.

Various embodiments of accomplishing fluid delivery are discussed further in U.S. Pat. No. 10,751,117 entitled "Electrosurgical Instrument With Fluid Diverter," issued Aug. 25, 2020 and U.S. Pat. Pub. No. 2019/0099209 entitled "Bipolar Electrode Saline Linked Closed Loop Modulated Vacuum System" published Apr. 4, 2019, which are each hereby incorporated by reference in their entireties.

An ablation device, such as the ablation device 1410 of FIG. 23, the ablation device 1490 of FIG. 34 to FIG. 36, the ablation device 1500 of FIG. 37, and other ablation devices, can include an electrode configuration that is configured to improve electrode contact with tissue. The electrode can include an electrode array so as to include a plurality of electrodes, such as with the ablation device 1490 of FIG. 34 to FIG. 36, the ablation device 1500 of FIG. 37, and other ablation devices. Controlling electrode contact for an electrode array may help improve overall contact of each of the electrodes to the tissue being ablated.

For example, electrode contact control for an electrode array can be achieved using conformal changes in each electrode.

For another example, electrode contact control for an electrode array can be achieved by adjusting a rate of fluid (e.g., saline) flow and/or adjusting a salinity of fluid (e.g., saline) being delivered to a site of the electrode contact, as discussed above.

For yet another example, electrode contact control for an electrode array can be achieved by changing a pressure of an ablation device's balloon to improve tissue contact of the ablation device's electrodes. As one example, changing the pressure of a balloon can be achieved using holes in the balloon, such as the holes 1512 of the balloon 1510 of the ablation device 1500 of FIG. 37. The holes 1512 allow fluid in the balloon 1510 to leak out of the balloon 1510 such that the balloon's pressure will decrease over time (if no additional fluid is introduced into the balloon 1510). The contact the electrodes 1506 have with tissue will thus decrease over time as the balloon 1510 deflates/compresses since the electrodes 1506 are attached to the balloon 1510. This decreased electrode contact may help prevent the tissue from overheating and/or from nearby tissue not intended for ablation from becoming overheated. As another example, changing the pressure of the balloon can be achieved by using a segmented balloon in which the balloon includes a plurality of segments each configured to be independently inflated/expanded and independently deflated/compressed. Each of the balloon segments can have at least one electrode attached thereto such that the s balloon segment's associated electrode(s) can have their contact controlled by the balloon segment's inflation/expansion and deflation/compression. The independently controllable balloon segments can allow off-center pressures to be provided, which may accommodate an irregular interior circular shape of a hollow organ or body lumen. The balloon segments can be arranged to form a toroid, such as by being arranged in a flower petal radial pattern, so as to extend 360° for complete perimeter control.

For still another example, electrode contact control for an electrode array can be achieved by using a vacuum to pull tissue into contact with the ablation device's electrodes. A vacuum can be achieved, for example, using suction through at least one suction tubes, such as by using the suction tubes 1514, 1516 of the ablation device 1500 of FIG. 37. The vacuum can originate from a single source, but in such instances the vacuum can be segmented such that individual vacuum channels can follow individual electrodes. Such segmentation may minimize blockages and/or may allow suction to continue for one or more vacuum channels and their associated electrodes to improve electrode contact when one or more other vacuum channels associated with other electrodes are not applying suction since electrode contact is already sufficient. Various embodiments of using a vacuum are discussed further in previously mentioned U.S. Pat. No. 10,751,117 entitled "Electrosurgical Instrument With Fluid Diverter," issued Aug. 25, 2020 and U.S. Pat. Pub. No. 2019/0099209 entitled "Bipolar Electrode Saline Linked Closed Loop Modulated Vacuum System" published Apr. 4, 2019.

For another example, electrode contact control for an electrode array can be achieved using forward and distal balloon occlusion of a lumen to provide for location suction at each electrode's ablation zone. Positioning the occlusion in a range of about 1 cm to about 3 cm beyond the electrode's ablation zone can allow for intraluminal conformance to the electrode array.

For still another example, electrode contact control for an electrode array can be achieved by measuring electrode contact quality and, based on the measurement, taking an action to improve electrode contact quality. Electrode contact quality can be measured, for example, using a return electrode monitoring (REM) system in a return pad circuit. A contact quality problem can be identified based on contact resistance between any two sets of the electrodes being determined to be significantly different than other sets of the electrodes. In response to identifying a contact quality problem, a responsive action can be automatically taken, e.g., by a controller of a surgical hub, a robotic surgical system, or other computer system controlling the ablation device and/or other relevant device. Examples of responsive actions include changing a pressure of the ablation device's balloon, moving the ablation device rotationally and/or translationally to readjust electrode position and thereby readjust electrode contact, and introducing saline to the problematic electrode contact area. Various embodiments of return electrodes are discussed further below.

For yet another example, electrode contact control for an electrode array can be achieved using an adaptive force application structure operatively coupled to the electrode array and configured to apply an outwardly directed force proportionate to a temperature measured locally to the adaptive force application structure, such as tissue temperature. Tissue temperature can be measured in a variety of ways, as discussed herein.

The adaptive force application structure can be printed using four-dimensional (4D) printing. A 4D printed object is a 3D printed object that can change structure over time. The material(s) with which the 4D printed structure is printed are configured to change when exposed to a particular condition such as heat, magnetic energy, water, light, or other condition. For example, an ablation device's basket, such as the basket 1502 of the ablation device 1500 of FIG. 37, can be 4D printed using a material configured to change in response to temperature. The basket can thus be configured to compress or expand in response to particular temperatures, thereby allowing the electrode(s) attached to the basket to have their tissue contact adjusted based on whether the basket expands to increase electrode tissue contact or compresses to decrease electrode tissue contact. For another example, an ablation device's basket, such as the basket 1502 of the ablation device 1500 of FIG. 37, can be made from a shape memory material configured to change shape in response to temperature changes. As ablation occurs, the heat being applied can cause the shape memory material to change shape, thereby changing the contact of the ablation device's electrode(s) with tissue, such as by causing the electrode(s) to be pushed radially outwardly to urge the electrode(s) into contact with the tissue.

Instead of being 4D printed with material(s) configured to respond to temperature change, the 4D printed structure can be printed with material(s) configured to respond to magnetism to control electrode contact. As discussed herein, a surgical procedure in which an ablation device is used in a duodenum or other anatomic structure can also include a laparoscope or other imaging device positioned outside the duodenum or other anatomic structure in which the ablation device is located. A magnet can be introduced through a working channel of the laparoscope or other imaging device outside the duodenum or other anatomic structure in which the ablation device is positioned. The magnet can then be used to move the 4D printed structure within the duodenum or other anatomic structure in which the ablation device is positioned by repelling the magnetic structure.

Instead of being 4D printed with magnetic material(s), one or more magnets can be attached to an ablation device, such as on each arm or wire of an electrode array. A magnet can be introduced through a working channel of the laparoscope or other imaging device outside the duodenum or other anatomic structure in which the ablation device is positioned. The magnet can then be used to move the structure to which the one or more magnets within the duodenum or other anatomic structure in which the ablation device is positioned by repelling the one or more magnets.

Various embodiments of using a magnetic element located outside a hollow organ or body lumen and a magnetic element located into the hollow organ or body lumen are discussed further below.

For yet another example, electrode contact control for an electrode array can be achieved by each electrode of the electrode array being operatively coupled to an independent spring wire, with the spring wires being connected together by a collar. The collar is configured to selectively advance distally and retract proximally so as to selectively cause the electrode array to retract (collar advanced distally) or expand (collar retracted proximally). The collar can thus simulate the electrode array being advanced distally out of a sheath or scope or retracting proximally into a sheath or scope.

For yet another example, electrode contact control for an electrode array can be achieved using a sleeve or stent positioned around an outer diameter of a duodenum or other anatomic structure in which an ablation device is located to ablate tissue. The sleeve or stent so positioned is configured to provide a more uniform surface against which the electrodes can press from inside the duodenum or other anatomic structure than the tissue alone can provide, which may allow for more precise and consistent energy delivery by allowing for more uniform tissue contact.

The sleeve or stent can be positioned around the outer diameter in a variety of ways. For example, the sleeve or stent can be an elongate member that a surgical device advances around the outer diameter with a free distal end of the elongate member leading the advancement. The free distal end wraps around the outer diameter to return to and releasably attach to the device, such as with a magnet. The free distal end can thereafter be released from the device to unwrap the elongate member from around the outer diameter so the elongate member can be removed from the patient's body. The sleeve or stent can thus be similar to a sizer that a laparoscopic sizing tool, such as the LINX® Laparoscopic Sizing Tool (available from Ethicon US LLC of Cincinnati, OH), positions around an outer diameter of a tissue.

A location of where to position the sleeve or stent outside the duodenum or other anatomic structure at a location that corresponds to an internal ablation location can be determined using a fiducial marker on a balloon or other element of the ablation device that is positioned inside the duodenum or other anatomic structure, for example on the balloon 1412 of the ablation device 1410 of FIG. 23. The fiducial marker can be magnetic, thereby allowing the fiducial marker inside the duodenum or other anatomic structure to be located magnetically from outside the duodenum or other anatomic structure without naked eye or visible light visualization of the fiducial marker or the balloon to which the fiducial marker is attached. The sleeve can be configured to communicate its location to a controller of a surgical hub, a robotic surgical system, or other computer system, which the controller can use to verify the sleeve being properly positioned at a site of ablation since the ablation device's position will be known.

After the ablation has been performed, the sleeve or stent can be removed from the duodenum or other anatomic structure and from the patient's body.

Regardless of how electrode contact is controlled, the energizing and turning off of the electrodes can be correlated with outward radial pressures being applied by the electrodes to tissue such that pressure and power can be controlled simultaneously. For example, each of the electrodes can be configured to be energized only if a pressure threshold for that electrode is met, e.g., if the electrode is measured to be exerting a pressure on the tissue above a predetermined minimum pressure threshold, such that pressure and power can be controlled simultaneously. An electrode may thus not needlessly attempt to be delivering energy to tissue when the electrode's contact with the tissue is insufficient for effective ablation. The pressure can be measured, for example, using a pressure sensor.

Controlling Electrode Power

Devices, systems, and methods for multi-source imaging provided herein may allow for controlling electrode power. As discussed herein, a surgical procedure can include ablating tissue using a plurality of electrodes. For example, FIG. 23 illustrates an ablation device 1410 including an electrode that can include a plurality of electrodes. For another example, FIG. 28 illustrates an ablation device 1440 including an electrode that can include a plurality of electrodes. For yet another example, FIG. 31 illustrates an ablation device including a plurality of electrodes 1460, 1462. For still another example, FIG. 34 to FIG. 36 illustrate an ablation device 1490 including a plurality of electrodes. For another example, FIG. 37 illustrates an ablation device 1500 including a plurality of electrodes 1506.

In some embodiments, the plurality of electrodes can be collectively controlled such that each of the electrodes is at a same power level and is turned on/off at the same time. Such power control may simplify energy control, but it does not take into account that different ones of the electrodes may be delivering energy to tissue having different characteristics, such as different temperature, different thickness, and/or different impedance, such that one or more of the electrodes is not efficiently delivering energy to tissue and/or adjacent tissue not intended for ablation is being overly heated by the electrode's energy delivery. In some situations, one or more of the ablation device's electrodes may not be in contact with tissue at all or may not be fully in contact with tissue. For example, the ablation device can be expanded within a duodenum or other body lumen having an irregularly shaped inner circumference and/or an irregular inner surface such that one or more of the ablation device's electrodes is not contacting tissue at all within the duodenum or other body lumen or is only partially in contact with the tissue's inner surface. Electrodes in no or only partial contact with tissue may thus be powered improperly or unnecessarily for that electrode's tissue contact condition.

Controlling electrode power can include controlling each of a plurality of electrodes individually. The electrodes may therefore each deliver energy appropriate for the tissue with which the electrode is in contact and/or may have its power controlled to account for the electrode's tissue contact condition.

As discussed above, an algorithm stored on board an intelligent surgical device, such as an intelligent ablation device, or stored elsewhere can include one or more variable parameters that affect control of the surgical device. A controller of a surgical hub, a robotic surgical system, or other computer system can be configured to adjust at least one variable parameter of the algorithm to control electrode power. Each of the intelligent ablation device's plurality of electrodes can be affected by different variable parameters such that each of the electrodes can be individually controlled. Examples of variable parameters related to controlling electrode power include electrode power status (e.g., electrode on and delivering energy or electrode off and not delivering energy), rate of energy delivery, and power level (e.g., amount of power being delivered by the electrode).

The controller can be configured to receive a signal indicative of a measured parameter and, based on the signal, determine whether or not to adjust at least one variable parameter of the algorithm to control electrode power and, if so determined, adjust the at least one variable parameter accordingly. Electrode power may thus be controlled based on the measured parameter. The measured parameter can be associated with a particular electrode, or a particular subset of the electrodes, thereby allowing the controller to adjust the at least one variable parameter for the associated one(s) of the electrodes. Individual electrodes may thus be controlled based on the measured parameter. Examples of the measured parameter include tissue characteristics such as temperature, thickness, and impedance.

As discussed herein, various surgical procedures can include use of an intelligent ablation device and an imaging device. For example, in a procedure on a lung, an intelligent ablation device can be positioned inside a lung and an imaging device, such as a laparoscope, can be positioned outside the lung. FIG. 28 illustrates one embodiment of a such a lung procedure. For another example, in a procedure on an intestine, an intelligent ablation device can be positioned inside a duodenum and an imaging device, such as a laparoscope, can be positioned outside the duodenum. FIG. 23 illustrates one embodiment of a such an intestinal procedure.

Images gathered by the imaging device can be used, e.g., by a controller of a surgical hub, a robotic surgical system, or other computer system, to control power of electrodes of the ablation device. In an exemplary embodiment, the images can indicate a depth of tissue ablation and thus indicate whether unintended layer(s) of tissue are, e.g., in danger of being damaged by overheating. For example, as discussed herein, in a DMR procedure, the mucosal layer of the duodenum is the intended ablation target of the duodenum while outer layers of the duodenum are not intended for ablation.

The imaging device can gather images indicative of a temperature of tissue being ablated with the images indicating ablation depth by varying temperature levels in the imaged tissue, as discussed herein, for example with respect to FIG. 28. For another example, intraoperative CT imaging can provide images indicative of a temperature of tissue being ablated.

The controller can know a location and orientation of each of the electrodes and thus be able to associate the gathered temperature data with individual electrodes. For example, an imaging device can be configured to gather images from which location and orientation can be determined, as discussed herein. For another example, a Hall effect sensor or other sensor can be configured to sense from outside the tissue a clocking of the electrodes. The clocking can be used to related each individual electrode to a position of the measured temperature to relate electrode location to measured temperature.

As discussed herein, the imaging device can be used to determine a distance to a "hidden" object, which in this instance could be the tissue and/or each of the ablation device's electrodes. The distance can be used for any correction factor in reflectivity or temperature radiation impacts.

The depth of tissue ablation can be used by the controller to determine whether certain ones of the ablation device's electrodes should have their power adjusted. Thus, similar to that discussed herein with respect to FIG. 28, the controller can be configured to adjust at least one variable parameter associated with a particular electrode to control that electrode's power. As discussed herein, a tissue can have varying thickness and/or composition, so considering depth of ablation in controlling individual electrodes may help account for different thickness and/or composition around the tissue's circumference by allowing some electrodes to deliver more or less energy than other electrodes. For example, the controller can adjust at least one variable parameter to decrease or turn off power in response to the measured temperature for an outer, non-targeted tissue layer being above a first predetermined maximum threshold so as to indicate that the ablation is overly heating or is in danger of starting to overly heat unintended layer(s) of tissue. For another example, the controller can adjust at least one variable parameter to decrease or turn off power in response to the measured temperature for an inner, targeted tissue layer intended for ablation being above a second predetermined maximum threshold so as to indicate that the ablation has heated the target tissue being treated to a predetermined goal temperature or that the ablation is overly heating or is in danger of starting to overly heat intended layer(s) of tissue. For yet another example, the controller can adjust at least one variable parameter to increase or turn on power in response to the measured temperature for an inner, targeted tissue layer intended for ablation being less than a first predetermined minimum threshold so as to indicate that the ablation is not effectively heating for ablation the targeted layer(s) of tissue.

As discussed herein, a sleeve or stent can be positioned around an outer diameter of a duodenum or other anatomic structure in which an ablation device is located to ablate tissue. The sleeve or stent so positioned may help mitigate any variations in the outer diameter.

As discussed herein, return electrode(s) can be positioned outside tissue being ablated on another side of the tissue with other electrode(s). The return electrode(s) can be controlled similarly to that discussed herein with respect to internally applied electrodes. Controlling energizing of the return electrode(s) may help achieve a desired sealing effect and/or may allow the return electrode(s) to be directionally moved to a particular tissue location to provide more concentrated energy at that location. Various embodiments of return electrodes are discussed further below.

In some embodiments, instead of or in addition to tissue temperature being measured in some other way, each electrode of an ablation device's plurality of electrodes can be configured to measure tissue temperature. For example, each of the electrodes can include an integrated positive temperature coefficient (FTC) sensor or other temperature sensor. The controller may therefore be able to use the temperature measured by the electrode in controlling the electrode, similar to that discussed above for controlling the electrode using temperature measured in another way. For example, the controller can adjust at least one variable parameter to decrease or turn off power for an electrode in response to the temperature measured by that electrode being greater than a predetermined maximum threshold so as to indicate that the ablation has heated the target tissue being treated to a predetermined goal temperature or that the ablation is overly heating or is in danger of starting to overly heat the target tissue. For yet another example, the controller can adjust at least one variable parameter to increase or turn on power for an electrode in response to the temperature measured by that electrode being less than a predetermined minimum threshold so as to indicate that the ablation is not effectively heating the target tissue.

The electrode including a PTC sensor may allow the electrode to self-control its energy delivery. The PTC sensor can be positioned in the electrode's energy delivery path. The electrode self-controlling power can be used instead of or in addition to a controller controlling electrode power. In response to the measured temperature being greater than a predetermined maximum threshold, so as to indicate that the ablation is overly heating or is in danger of starting to overly heat the tissue being ablated, the resistance of the PTC will limit the power to the electrode until (and if) the measured temperature falls below the predetermined maximum threshold.

In some embodiments, movement of a scope through which an ablation device is introduced into a patient's body can be a function of power level of the ablation device's electrodes, of measured temperature, of tissue impedance, of pressure of the electrodes on the tissue, and of tissue conductivity. In this way, the tissue can be ablated at different locations along the scope's path of travel with the scope moving between the locations so as to effectively ablate the tissue at each of the locations before moving to the next location.

Figure 38:
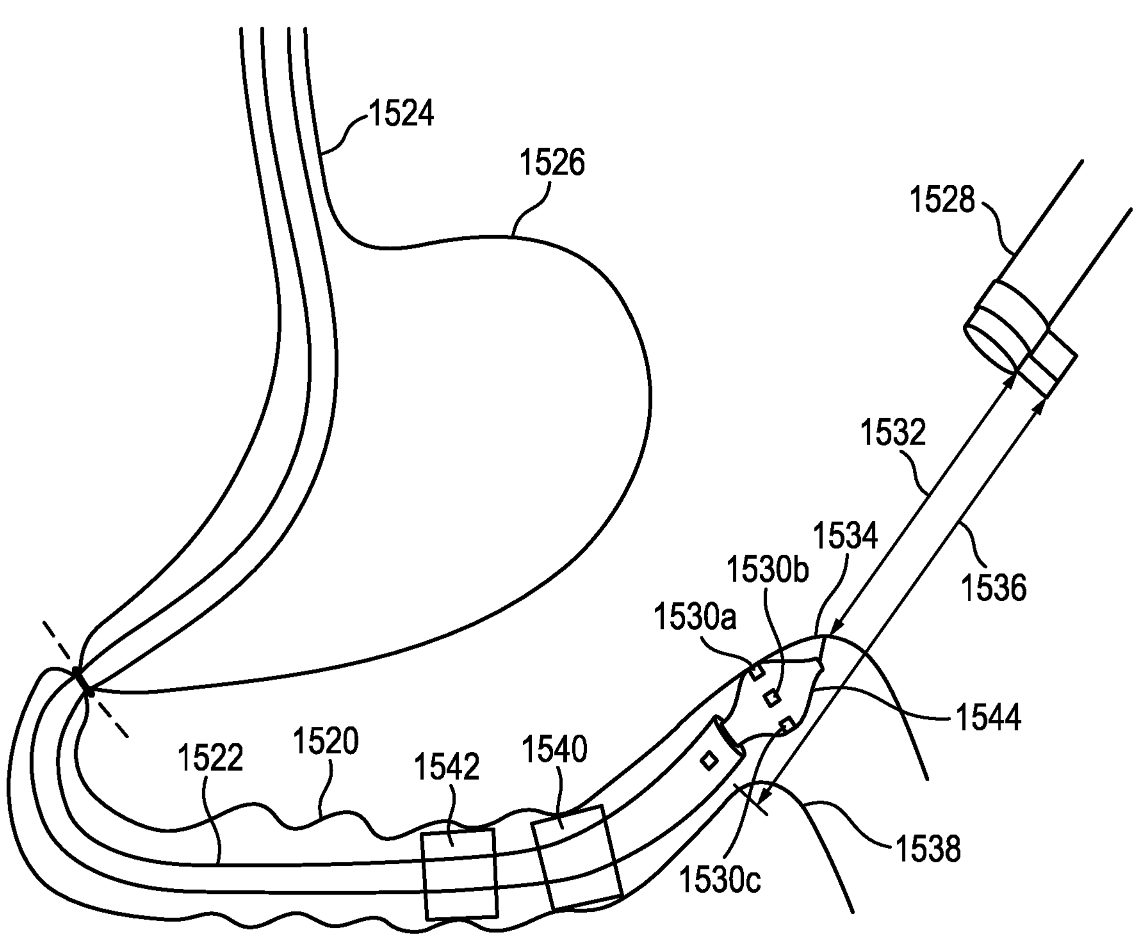
FIG. 38 is a perspective partially cross-sectional view of one embodiment of a scope and ablation device positioned in a body lumen and an imaging device positioned external to the body lumen.
Figure 39:
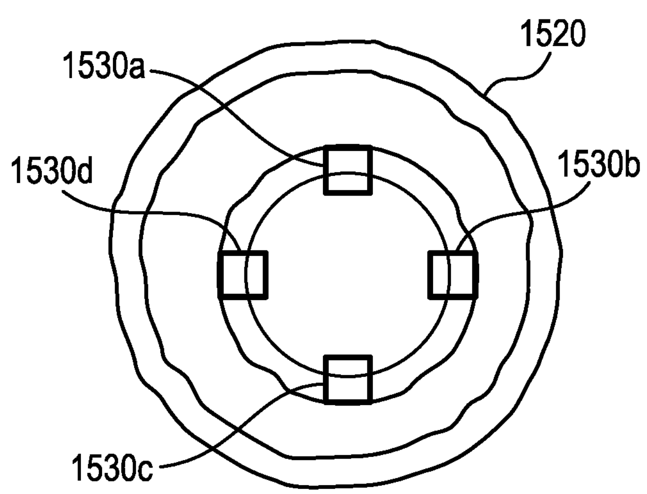
FIG. 39 is a schematic cross-sectional view of a portion of FIG. 38.

FIG. 38 illustrates one embodiment of scope movement being a function of power level of the ablation device's electrodes, measured temperature, tissue impedance, pressure of the electrodes on the tissue, and tissue conductivity. FIG. 38 shows a duodenum 1520 being ablated such as in a DMR procedure, but other surgical procedures can be performed with scope movement as described herein. In this illustrated embodiment, a scope 1522, such as an endoscope, has been introduced into the duodenum 1520 through the patient's esophagus 1524 and stomach 1526. An ablation device has been introduced into the duodenum 1520 through a working channel of the scope 1522 so as to extend distally from the scope 1522. As shown in FIG. 38 and FIG. 39, the ablation device in this illustrated embodiment includes first, second, third, and fourth electrodes 1530*a*, 1530*b*, 1530*c*, 1530*d* each attached to an inflatable or expandable balloon 1544. An imaging device 1528, such as a laparoscope, is positioned within the patient outside the duodenum 1520. FIG. 38 illustrates that the visualization provided by the imaging device 1528 allows, as discussed herein, a first distance 1532 between a near wall 1534 of the duodenum 1520 and the imaging device 1528 and a second distance 1536 between a far wall 1538 of the duodenum 1520 and the imaging device 1528 to be determined.

In this illustrated embodiment, the scope 1522 is moved proximally, e.g., is retracted, in a continuous motion from its illustrated location to a first location 1540 proximal to the illustrated location and from the first location 1540 to a second location 1542 proximal to the first location 1540. The electrodes 1530*a*, 1530*b*, 1530*c*, 1530*d* can ablate tissue in the duodenum 1520 in more than these two locations 1540, 1542.

Figure 40:
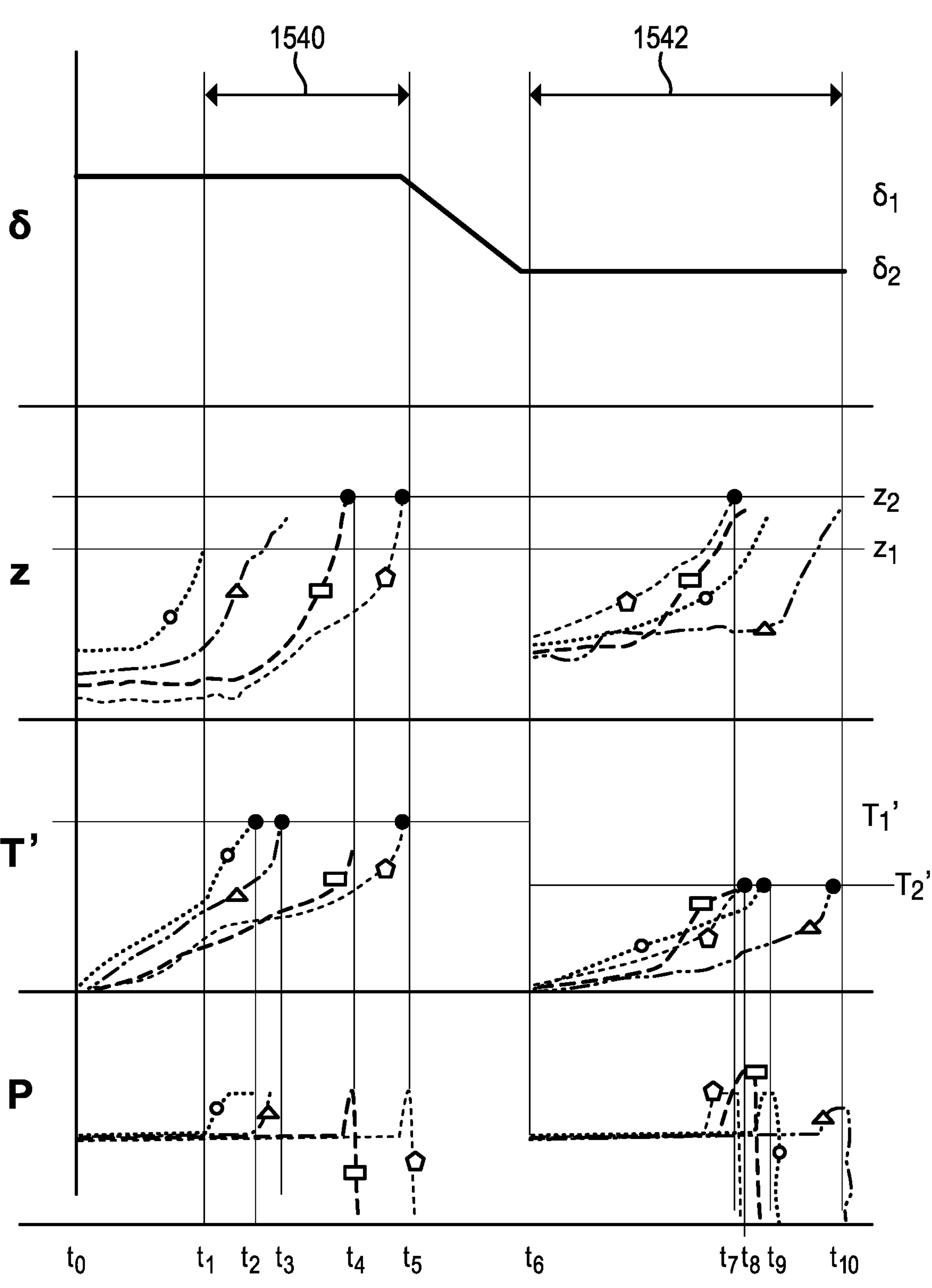
FIG. 40 is a graph showing time versus power, tissue impedance, tissue temperature, and electrode pressure with respect to the embodiment of FIG. 38.

FIG. 40 shows a graph over time, from time $t_0$ to time $t_{10}$, indicating power (δ), tissue impedance (Z), tissue temperature (T) and electrode pressure (P) on tissue during ablation in which each of the four electrodes 1530*a*, 1530*b*, 1530*c*, 1530*d* are delivering energy in each of the first and second locations 1540, 1542. A circle shape, a triangle shape, a rectangle shape, and a hexagon shape are shown on the lines for the first, second, third, and fourth electrodes 1530*a*, 1530*b*, 1530*c*, 1530*d*, respectively, in FIG. 40 only for identification purposes to help indicate which line corresponds to which electrode 1530*a*, 1530*b*, 1530*c*, 1530*d*.

Controlling electrode power can include monitoring a rate of change of temperature, which can be used to estimate tissue thickness where the temperature was measured. The estimated tissue thickness can then be used in controlling electrode power, e.g., in changing at least one variable parameter of an algorithm for at least one electrode of an ablation device.

Figures 41, 42:
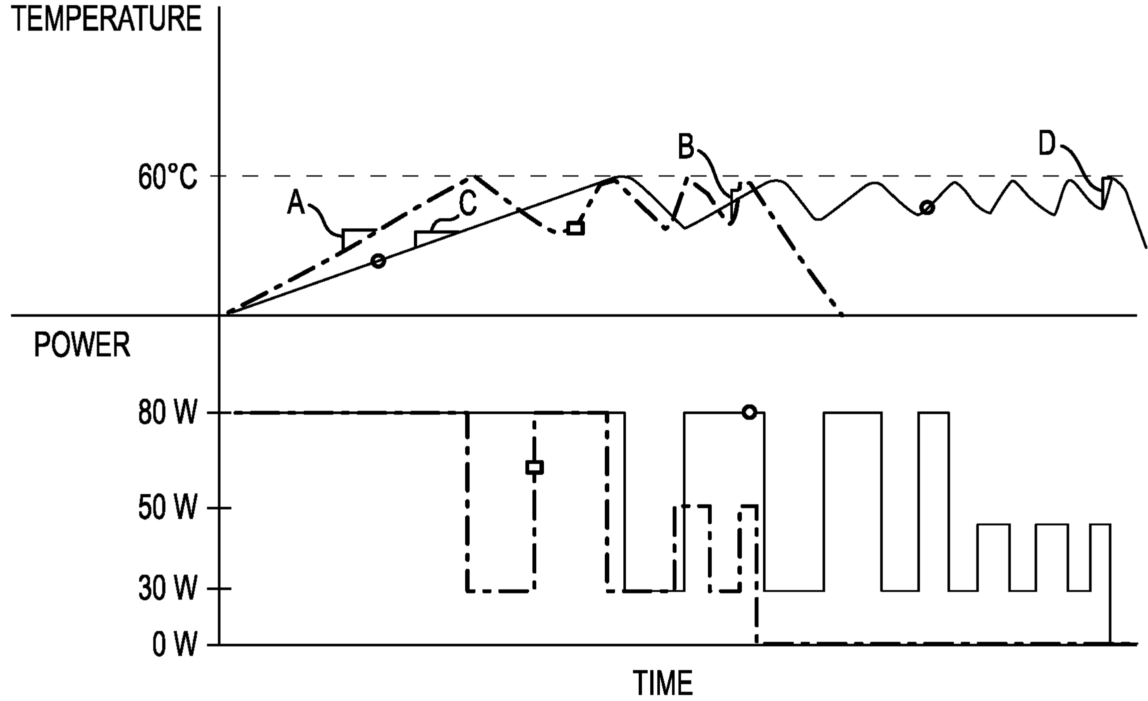
FIG. 41 is another schematic cross-sectional view of a body lumen having first and second electrodes positioned therein.
FIG. 42 is a graph showing temperature and power with respect to the embodiment of FIG. 41.

FIG. 41 and FIG. 42 illustrate one embodiment of controlling electrode power using measured temperature. In this illustrated embodiment, first and second electrodes 1550, 1552 are each positioned to contact an interior surface 1554 of a body lumen 1556. The body lumen 1556 can be, for example, a duodenum being ablated in a DMR procedure using an ablation device that includes the first and second electrodes 1550, 1552 on an inflatable or expandable balloon (see for example FIG. 23, FIG. 37, and FIG. 38) or other expandable member.

A temperature of an external surface 1558 of the body lumen 1556 is measured in this illustrated embodiment. The external surface 1558 temperature is monitored at first and second locations 1560, 1562 around an exterior circumference of the body lumen 1556 that correspond to the locations of the first and second electrodes 1550, 1552. The external surface 1558 temperature can be measured, for example, by using thermal imaging provided by an imaging device (not shown), such as a laparoscope, that is positioned outside of the body lumen 1556, by using a temperature sensor (e.g., a temperature sensor on a flexible force probe or other surgical device advanced through a working channel of the imaging device), or by using an IR sensor (e.g., an IR sensor on a flexible force probe or other surgical device advanced through a working channel of the imaging device). A different number of electrodes can be used in other embodiments, with a corresponding different number of external surface temperature measurements being gathered.

Measuring the external temperature at the first and second locations 1560, 1562 can help ensure that the heating provided by the first and second electrodes 1550, 1552 does not overheat the tissue's outer layers that are unintended targets of the ablation. As discussed above, the therapeutic temperature range for tissue ablation is in a range from about 60° C. to about 100° C., tissue being at a temperature above about 41° C. begins to make the tissue susceptible to or causes the tissue to incur irreversible cell damage, and tissue being at a temperature above about 50° C. is when irreversible tissue damage begins to occur.

FIG. 41 illustrates a first tissue thickness 1566 of the body lumen 1556 where the first electrode 1550 is located and where the first external temperature is being measured, and a second tissue thickness 1568 of the body lumen 1556 where the second electrode 1552 is located and where the second external temperature is being measured. The first tissue thickness 1566 is greater than the second tissue thickness 1568 in this illustrated embodiment.

FIG. 42 shows a graph plotting time versus measured first and second external temperatures at the first and second locations 1560, 1562, respectively, and power level of the ablation device that includes the electrodes 1550, 1552. A circle shape and a rectangle shape are shown on the lines for the first and second locations 1560, 1562, respectively, in FIG. 42 only for identification purposes to help indicate which line corresponds to temperature at which of the locations 1560, 1562 associated with which of the electrodes 1550, 1552. The graph demonstrates rate of change of the measured first and second external temperatures being used to indicate tissue thickness.

When power begins being provided to the electrodes 1550, 1552 for the electrodes 1550, 1552 to deliver energy to the body lumen 1556 (vertical axis line in the graph), the power is at its predetermined energy start level, which is 80 W in this illustrated embodiment. Reference A in the graph shows a starting rate of change for the second measured external temperature, and Reference C in the graph shows a starting rate of change for the first measured external temperature. The tissue is thinner where the second external temperature is being measured, as compared to where the first external temperature is being measured, so the "A" rate of change is greater than the "C" rate of change. As shown in the graph, in response to the measured external temperature at one of the first and second locations 1560, 1562 reaching a predetermined maximum temperature threshold, the power level is reduced for the associated electrode 1550, 1552. The predetermined maximum temperature threshold is 60° C. in this illustrated embodiment, but another value can be set, such as 41° C., 50° C., 70° C., or other value. Changing the power level for an electrode can be accomplished by changing at least one variable parameter of the algorithm being used to control ablation, as discussed herein. The first external temperature initially reaches the predetermined maximum temperature threshold later than the second external temperature due to first tissue thickness 1566 being greater than the second tissue thickness 1568, as reflected by the lower starting "C" rate of change. The power level for each of the first and second electrodes 1550, 1552 is repeatedly increased or decreased in response to the rate of change for each electrode's associated measured temperature and to the measured first external temperature (used in controlling the first electrode's power) and in response to the measured second external temperature (used in controlling the second electrode's power). Reference B in the graph shows an ending rate of change for the second measured external temperature, and Reference D in the graph shows an ending rate of change for the first measured external temperature. In response to detecting the ending rate of change for the second measured external temperature, power is turned off for the second electrode 1552, and the second measured external temperature thereafter decreases as shown in the graph. In response to detecting the ending rate of change for the first measured external temperature, power is turned off for the first electrode 1550, and the first measured external temperature thereafter decreases as shown in the graph. The first external temperature initially reaches the ending rate of change later than the second external temperature due to first tissue thickness 1566 being greater than the second tissue thickness 1568.

In some embodiments, controlling electrode power using a monitored rate of change of temperature can limit or control application of heat to a mucosal layer of tissue versus a serosal layer of the tissue. A flash intensity of energy can be delivered to ablate the mucosal layer with interconnection between the tissue's layers acting as a transient boundary that changes a conductivity of the applied energy. The flash of heat can be sufficient to kill mucosal cells in the mucosal layer, but by the time the heat dissipates to the serosal layer, the heat will not be enough to damage the serosal layer. The flash intensity can be higher than would normally be applied for ablation, but because it is delivered in a very fast, flash fashion, the high amount of power can be used without overly heating the serosal layer.

Controlling electrode power can include monitoring a temperature gradient, which can then be used in controlling electrode power, e.g., in changing at least one variable parameter of an algorithm for at least one electrode of an ablation device.

Figure 43:
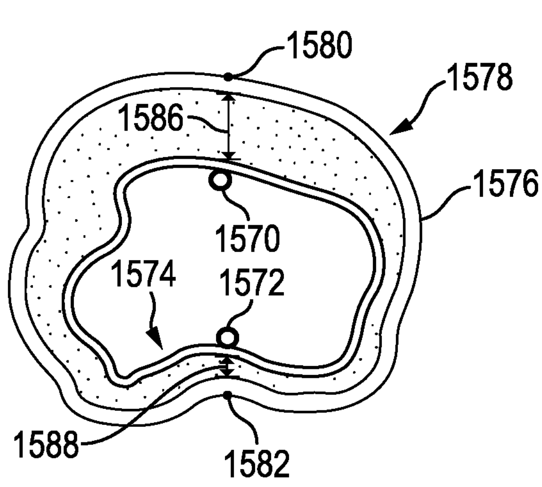
FIG. 43 is yet another schematic cross-sectional view of a body lumen having first and second electrodes positioned therein.
Figure 44:
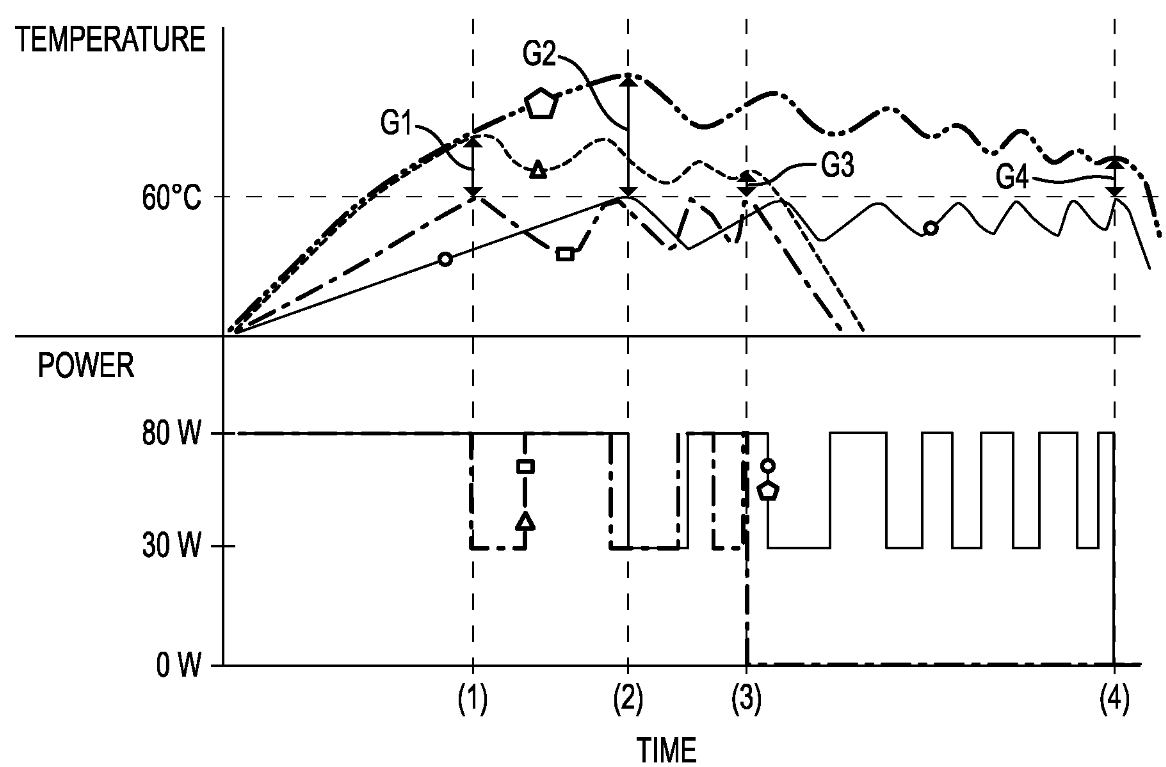
FIG. 44 is a graph showing temperature and power with respect to the embodiment of FIG. 43.

FIG. 43 and FIG. 44 illustrate one embodiment of controlling electrode power using a temperature gradient. In this illustrated embodiment, first and second electrodes 1570, 1572 are each positioned to contact an interior surface 1574 of a body lumen 1576. The body lumen 1576 can be, for example, a duodenum being ablated in a DMR procedure using an ablation device that includes the first and second electrodes 1570, 1572 on an inflatable or expandable balloon (see for example FIG. 23, FIG. 37, and FIG. 38) or other expandable member.

A temperature of an exterior surface 1578 of the body lumen 1576 at first and second locations 1580, 1582 around an exterior circumference of the body lumen 1576 that correspond to the locations of the first and second electrodes 1570, 1572 is measured in this illustrated embodiment similar to that discussed above regarding FIG. 31 and FIG. 41. A temperature of the interior surface 1574 of the body lumen 1576 is measured in this illustrated embodiment at the locations of the first and second electrodes 1570, 1572 similar to that discussed above regarding FIG. 31. A different number of electrodes can be used in other embodiments, with a corresponding different number of external and internal surface temperature measurements being gathered.

FIG. 43 illustrates a first tissue thickness 1586 of the body lumen 1576 where the first electrode 1570 is located and where the first external temperature is being measured, and a second tissue thickness 1588 of the body lumen 1576 where the second electrode 1572 is located and where the second external temperature is being measured. The first tissue thickness 1586 is greater than the second tissue thickness 1588 in this illustrated embodiment.

Similar to that discussed above, measuring internal and external temperatures of the body lumen 1576 allows a temperature gradient to be established from outside the serosal layer to the mucosal layer inside the lumen 1576 such that a temperature of each tissue layer can be established. The internal and external temperatures will not be the same before ablation begins because the inner tissue layer, e.g., mucosal layer, acts as an insulator. The internal and external temperatures will not be the same during ablation since the internal surface 1574 of the body lumen 1576 is having heat applied thereto.

FIG. 44 shows a graph plotting time versus temperature and power level of the ablation device that includes the electrodes 1570, 1572. The first and second measured internal temperatures and the first and second measured external temperatures are shown in the graph. A circle shape, a rectangle shape, a hexagon shape, and a triangle shape are shown on the lines for the first and second measured external temperatures and the first and second measured internal temperatures, respectively, in FIG. 44 only for identification purposes to help indicate which line corresponds to temperature at which of the locations associated with which of the electrode 1570, 1572. The graph demonstrates temperature gradient being used to indicate tissue thickness.

When power begins being provided to the electrodes 1570, 1572 for the electrodes 1570, 1572 to deliver energy to the body lumen 1576 (vertical axis line in the graph), the power is at its predetermined energy start level, which is 80 W in this illustrated embodiment. Power level remains at 80 W for each of the electrodes 1570, 1572 until time (1), when a temperature gradient G1 associated with the second electrode 1572 is determined to not meet a predetermined temperature gradient threshold for the second electrode 1572 when the measured second external temperature reaches a predetermined maximum temperature threshold. The temperature gradient associated with the second electrode 1572 is defined by a difference between the measured second external and internal temperatures. The predetermined maximum temperature threshold is 60° C. in this illustrated embodiment, but another value can be set, such as 41° C., 50° C., 70° C., or other value. The tissue is thinner where the second external and internal temperatures are being measured, as compared to where the first external and internal temperatures are being measured, so the second external temperature reaches the predetermined maximum temperature threshold before the first external temperature reaches the predetermined maximum temperature threshold. As shown in the graph, in response to the temperature gradient G1 associated with the second electrode 1572 not meeting, e.g., exceeding, the predetermined temperature gradient threshold for the second electrode 1572 when the measured second external temperature reaches the predetermined maximum temperature threshold, the power level is reduced for the second electrode 1572 at time (1). Changing the power level for an electrode can be accomplished by changing at least one variable parameter of the algorithm being used to control ablation, as discussed herein.

The first external temperature initially reaches the predetermined maximum temperature threshold at time (2), later than the second external temperature at time (1), due to first tissue thickness 1586 being greater than the second tissue thickness 1588. As shown in the graph, in response to the temperature gradient G2 associated with the first electrode 1570 not meeting the predetermined temperature gradient threshold for the first electrode 1570 when the measured first external temperature reaches the predetermined maximum temperature threshold, the power level is reduced for the first electrode 1570 at time (2). The temperature gradient associated with the first electrode 1570 is defined by a difference between the measured first external and internal temperatures.

The power level for each of the first and second electrodes 1570, 1572 is repeatedly increased or decreased in response to the temperature gradient associated with each electrode 1570, 1572 when the measured external temperature associated therewith reaches the predetermined maximum temperature threshold.

At time (3) the temperature gradient G3 associated with the second electrode 1572 first meets, e.g., is less than, the predetermined temperature gradient threshold for the second electrode 1572 when the measured second external temperature reaches the predetermined maximum temperature threshold. In response, the power is turned off for the second electrode 1572 at time (3). The second measured external and internal temperatures thereafter decrease as shown in the graph. At time (4) the temperature gradient G4 associated with the first electrode 1570 first meets, e.g., is less than, the predetermined temperature gradient threshold for the first electrode 1570 when the measured first external temperature reaches the predetermined maximum temperature threshold. In response, the power is turned off for the first electrode 1570 at time (4). The first measured external and internal temperatures thereafter decrease as shown in the graph. The temperature gradient associated with the first electrode 1570 meets the predetermined temperature gradient threshold later than the temperature gradient associated with the second electrode 1572 due to first tissue thickness 1586 being greater than the second tissue thickness 1588.

Controlling electrode power can include monitoring at least one optical property (absorption, scattering, etc.) of the tissue being ablated, which can then be used in controlling electrode power, e.g., in changing at least one variable parameter of an algorithm for at least one electrode of an ablation device, similar to that discussed above regarding rate of change and temperature gradient.

Controlling electrode power can include monitoring external tissue temperature with or without also monitoring internal tissue temperature, as discussed herein. In some embodiments, monitoring external tissue temperature can include using one or more fiber optic sensors. The fiber optic sensors can be advanced to the tissue through a working channel of an imaging device, such as a laparoscope, positioned outside of the tissue being ablated from within, e.g., being ablated using an ablation device. The fiber optic sensors can include fiber optic pressure sensors and/or fiber optic temperature sensors. One example of a fiber optic pressure sensor is the OPP-M200 fiber optic pressure sensor available from Opsens Solutions Inc. of Qudbec, Canada. Examples of fiber optic temperature sensors include the OTG series of fiber optic temperature sensors available from Opsens Solutions Inc. of Québec, Canada.

Each of the one or more fiber optic sensors can be positioned at a location corresponding to where an electrode of the ablation device is contacting tissue inside the tissue. A number of the fiber optic sensors can thus equal a number of the electrodes. A location of where to position each of the one or more fiber optic sensors outside the tissue at a location that corresponds to the one or more electrodes inside the tissue can be determined, for example, using a fiducial marker that is positioned inside the tissue. Various embodiments of using a fiducial marker to determine a location of an ablation device and/or a scope through which an ablation device has been advanced are discussed further below.

Figure 45:
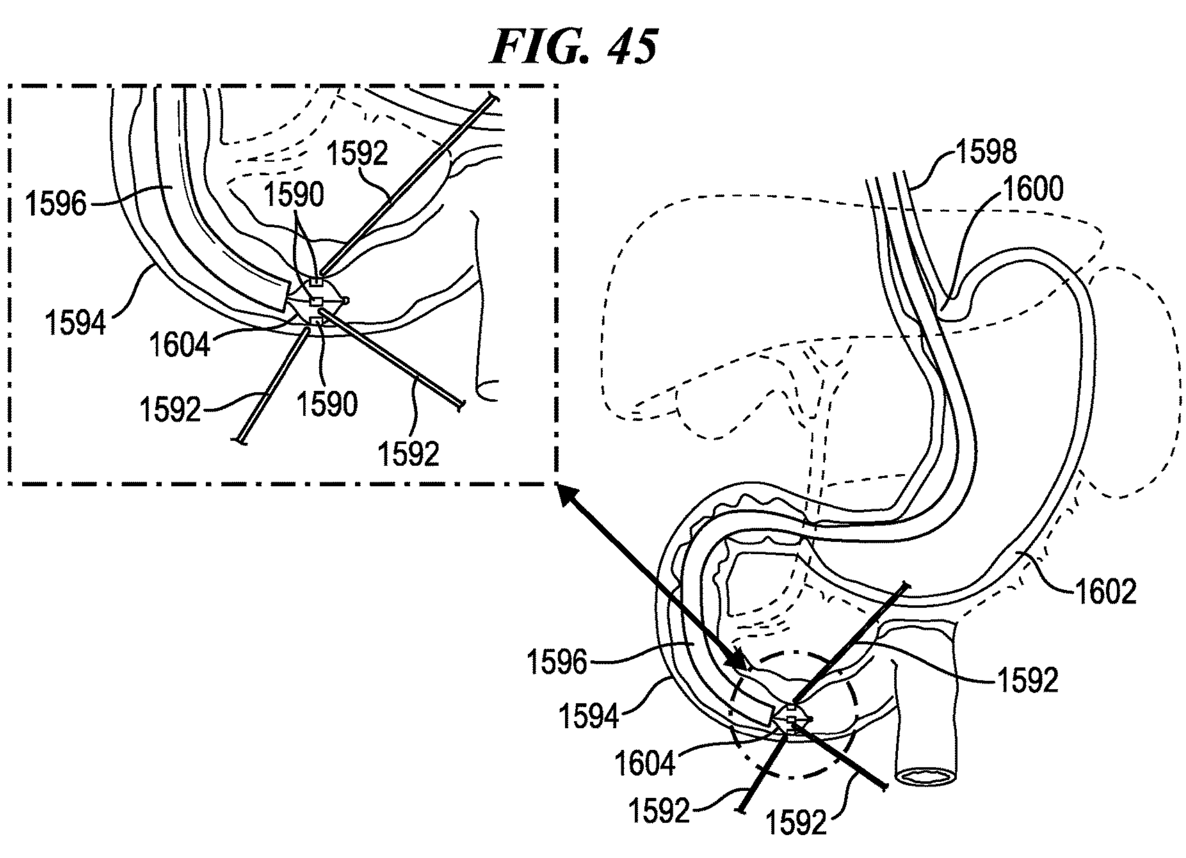
FIG. 45 is a perspective partially cross-sectional view of one embodiment of a scope and ablation device positioned in a body lumen and fiber optic sensors positioned external to the body lumen.
Figure 46:
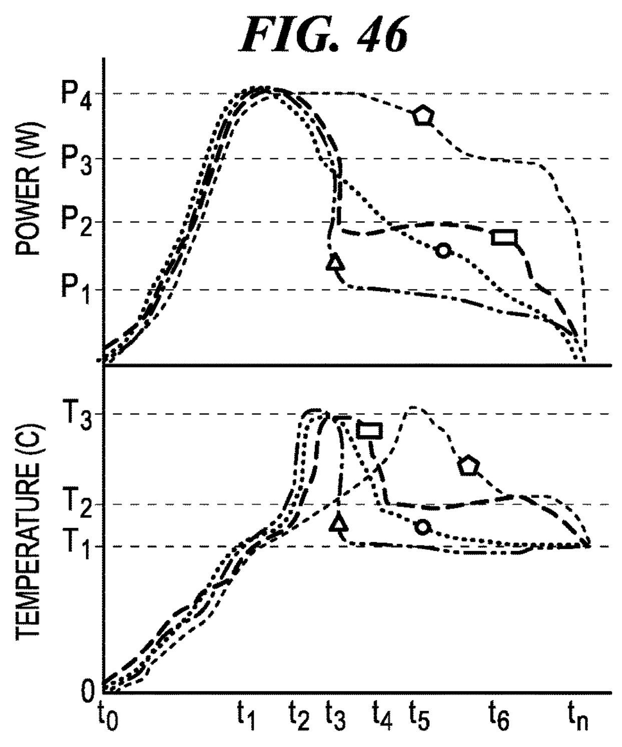
FIG. 46 is a graph showing temperature and power with respect to the embodiment of FIG. 45.

FIG. 45 and FIG. 46 illustrate one embodiment of using one or more fiber optic temperature sensors to monitor external tissue temperature and using the monitored external tissue temperature to control electrode power. Four electrodes 1590 and four fiber optic temperature sensors 1592 are shown in this illustrated embodiment, but another number of electrodes and fiber optic sensors can be used. One of the electrodes 1590 and one of the fiber optic sensors 1592 is obscured in FIG. 45.

FIG. 45 shows a duodenum 1594 being ablated such as in a DMR procedure, but other surgical procedures can be performed using fiber optic sensors. In this illustrated embodiment, a scope 1596, such as an endoscope, has been introduced into the patient's duodenum 1594 through the patient's esophagus 1598, esophageal sphincter 1600, and stomach 1602. An ablation device has been introduced into the duodenum 1594 through a working channel of the scope 1596 so as to extend distally from the scope 1596. Each of the ablation device's first, second, third, and fourth electrodes 1590 is attached to an inflatable or expandable balloon 1604 of the ablation device. An imaging device (not shown), such as a laparoscope, is positioned within the patient outside the duodenum 1594. The fiber optic sensors 1592 have been advanced to the duodenum 1594 through a working channel of an imaging device and positioned outside of the duodenum 1594 with each of the fiber optic sensors 1592 being positioned at an external surface of the duodenum at a location corresponding to one of the electrode's location within the duodenum 1594.

FIG. 46 shows a graph of time, from time $t_0$ to time $t_n$, versus power (in Watts) and tissue temperature (in ° C.) measured by the fiber optic sensors 1592. A circle shape, a triangle shape, a rectangle shape, and a hexagon shape are shown on the lines for the first, second, third, and fourth fiber optic sensors 1592 and the first, second, third, and fourth corresponding electrodes 1590, respectively, in FIG. 46 only for identification purposes to help indicate which line corresponds to which electrode 1590/fiber optic sensor 1592 pair. Ablation begins at time to with each of the electrodes 1590 starting to deliver energy. Temperature $T_3$ in the graph defines a predetermined maximum threshold that, when measured by a particular fiber optic sensor 1592, triggers a controller of a surgical hub, a robotic surgical system, or other computer system to adjust the power for the corresponding electrode 1590, e.g., by changing at least one variable parameter of an algorithm, so the tissue temperature can decrease to help protect the duodenum's outer layers unintended for ablation from being overly heated. Power stops being provided to each of the electrodes 1590 at time $t_n$, which corresponds to when each of the four measured external tissue temperatures has reached temperature $T_1$, which is less than temperature $T_3$ and defines a predetermined minimum threshold. The temperatures are not the same for each of the electrode 1590/fiber optic sensor 1592 pairs over time $t_0$ to time $t_n$, indicating that the thickness of the tissue where each electrode 1590/fiber optic sensor 1592 pair is positioned is not the same.

Fiber optic temperature sensors 1592 are used in the embodiment of FIG. 45 and FIG. 46, but as mentioned above, fiber optic pressure sensors can be used. In such embodiments, pressure of the electrodes on tissue can be measured and electrode power controlled accordingly. Fiber optic pressure sensors can be used in addition to or instead of fiber optic temperature sensors or other temperature sensing means.

For an ablation device including a plurality of electrodes, all of the plurality of electrodes can be simultaneously delivering power, one or more of the plurality of electrodes can deliver energy while one or more others of the plurality of electrodes are not delivering energy. As also discussed herein, the plurality of electrodes can be attached to an expandable or inflatable member such as a basket or a balloon. FIG. 47 to FIG. 50 illustrate various ones of a plurality of electrodes 1610 of an ablation device 1616 (partially shown in FIG. 47 to FIG. 50) attached to a basket 1612 of the ablation device 1616 and delivering energy with the basket 1612 in different expansion states. A distal tip 1618 of the ablation device 1616 to which a distal end of the basket 1612 is attached is also shown in FIG. 47 to FIG. 50. Four electrodes 1610 are shown in this illustrated embodiment, but another number of electrodes can be used. Depending on a size of a body lumen in which the basket 1612 is positioned, the basket 1612 can have different amounts of expansion for the electrodes 1610 to each contact an internal surface of the tissue. Depending on measured parameter(s), different ones of the electrodes 1610 can be simultaneously delivering energy and in combinations other than those illustrated in FIG. 47 to FIG. 50.

FIG. 47 illustrates the basket 1612 in a first state of expansion and each of the electrodes 1610 delivering energy in their respective ablation zones 1614. The electrodes 1610 each have a same power and thus have same-sized ablation zones 1614. Adjacent ablation zones 1614 overlap with one another.

More than one electrode 1610 can thus contribute to ablation of a same tissue location. FIG. 48 illustrates the basket 1612 in a second, greater state of expansion and each of the electrodes 1610 delivering energy in their respective ablation zones 1614. The electrodes 1610 each have a same power and thus have same-sized ablation zones 1614. Unlike with the basket 1612 in the first, smaller state of expansion, the ablation zones 1614 do not overlap with the basket 1612 in the second state of expansion even though the electrodes 1610 have a same power in FIG. 47 and FIG. 48. FIG. 49 illustrates the basket 1612 in the first state of expansion with two of the electrodes 1610' not delivering energy (power off) and two of the electrodes 1610 delivering energy in their respective ablation zones 1614. The electrodes 1610 that are delivering energy have a same power in FIG. 47, FIG. 48, and FIG. 49 and thus have same-sized ablation zones 1614. FIG. 50 illustrates the basket 1612 in the second state of expansion with one of the electrodes 1610' not delivering energy (power off) and three of the electrodes 1610, 1610" delivering energy in their respective ablation zones 1614. One of the electrodes 1610" delivering energy has more power than the other two electrodes 1610 delivering energy and thus has a larger ablation zone 1614". The other two electrodes 1610 that are delivering energy have a same power as in FIG. 47, FIG. 48, and FIG. 49 and thus have same-sized ablation zones 1614.

In some embodiments, controlling electrode power can include using previous ablation settings used with a particular patient and a particular ablation device as the ablation device is used at different locations in the patient. Ablation may therefore be performed faster and/or more efficiently. For example, a memory operably coupled to a controller of a surgical hub, a robotic surgical system, or other computer system controlling the ablation device can store therein the one or more variable parameters of an algorithm the controller uses during a surgical procedure to control the ablation device in ablating tissue at a particular location in the patient. As discussed herein, the one or more variable parameters can change during performance of the surgical procedure. After the ablation has stopped and the ablation device has been moved to a second location in the patient to ablate the tissue at the second location, the controller can use the stored one or more variable parameters of the algorithm when beginning ablation at the second location since those variable parameter(s) have already been determined to be effective for that patient and that tissue. The one or more variable parameter(s) may change during the ablation at the second location but may be more likely to not need much or any adjusting by using the previously used parameter settings.

Controlling electrode power can include monitoring a plurality of parameters and using each of the monitored parameters to adjust the power for each of one or more electrodes being used to ablate tissue. The plurality of parameters can include, for example, two or more of tissue impedance, external tissue temperature (e.g., as measured using imaging, using a fiber optic temperature sensor, using a temperature sensor, etc.), internal tissue temperature (e.g., as measured using imaging, using a temperature sensor, etc.), and tissue pressure (e.g., as measured using a fiber optic pressure sensor, using a pressure sensor, etc.).

Controlling electrode power can include communicating measurements of each monitored parameter to a generator supplying energy to an ablation device's one or more electrodes.

In some embodiments, an end effector of a surgical device can include an elongate shaft and opposing jaws that are at the distal end of the elongate shaft. Such an end effector has a dual jaw configuration because the end effector includes two jaws. The jaws are configured to move between open and closed positions. One or both of the jaws can be movable to move the jaws between the open and closed positions. The jaws include at least one electrode configured to deliver energy to tissue engaged between the jaws. The delivered energy seals the tissue, such as sealing after the tissue has been cut by a cutting element of the surgical device. The end effector including at least one electrode can have a variety of configurations.

FIG. 51 illustrates one embodiment of an end effector 1700 including opposed upper and lower jaws 1702, 1704 configured to engage tissue therebetween. FIG. 51 shows the end effector 1700 open. The upper jaw 1702 includes a positive electrode 1706 configured to contact tissue engaged between the jaws 1702, 1704, and the lower jaw 1704 includes a negative electrode 1708 configured to contact tissue engaged between the jaws 1702, 1704. Controlling electrode power for the positive electrode can be similar to that discussed above regarding an ablation device's electrode.

Figure 52:
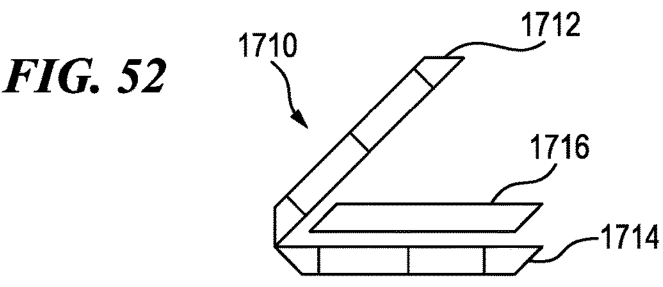
FIG. 52 is a side schematic view of another embodiment of an end effector including upper and lower jaws in an open position with tissue positioned between the upper and lower jaws.
Figure 53:
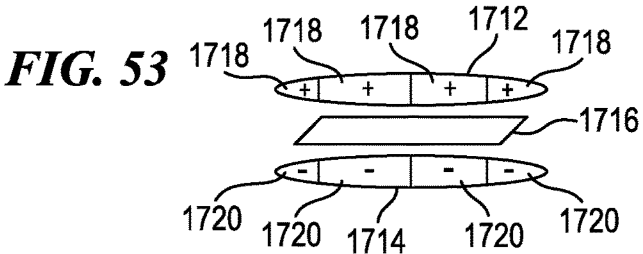
FIG. 53 is a cross-sectional view of one embodiment of an electrode configuration of the end effector of FIG. 52 with the upper and lower jaws in a closed position.
Figure 53A:
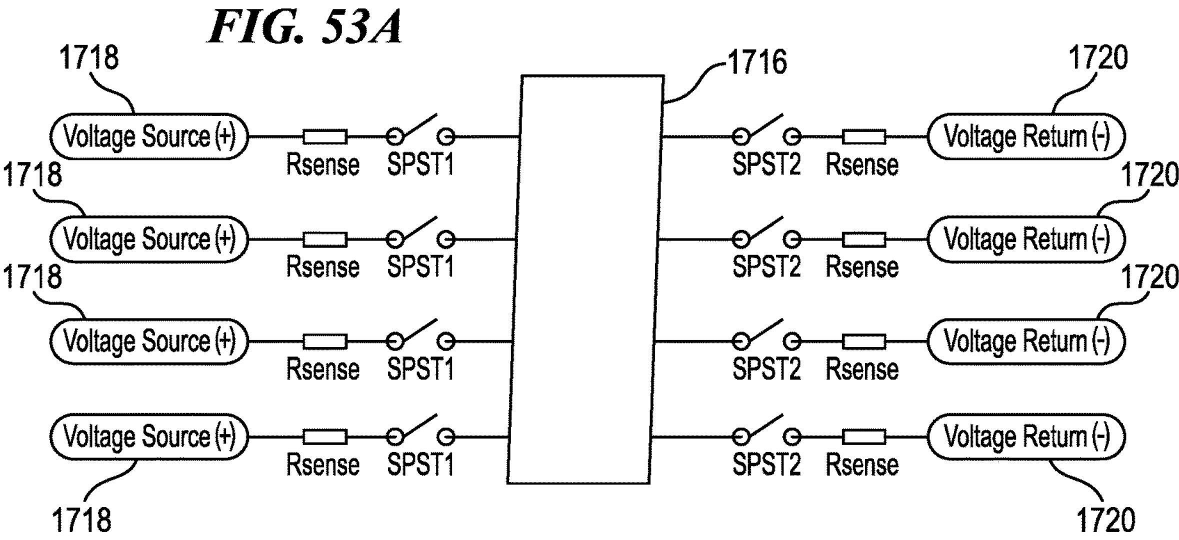
FIG. 53A is a schematic view of the electrode configuration and tissue of FIG. 53.
Figure 54:
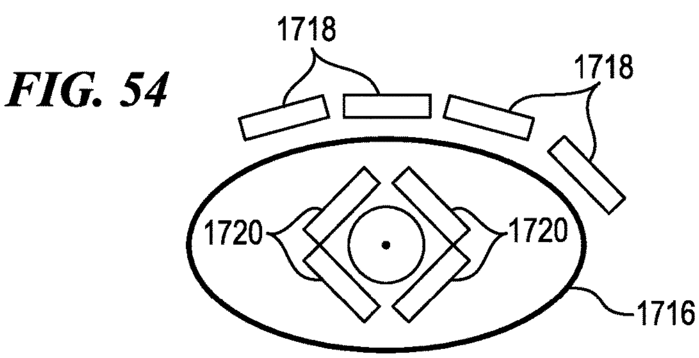
FIG. 54 is another cross-sectional view of the upper and lower jaws and the tissue of FIG. 53.
Figure 55:
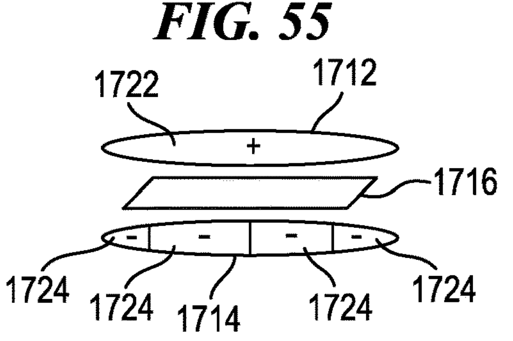
FIG. 55 is a cross-sectional view of another embodiment of an electrode configuration of the end effector of FIG. 52 with the upper and lower jaws in a closed position.
Figure 56:
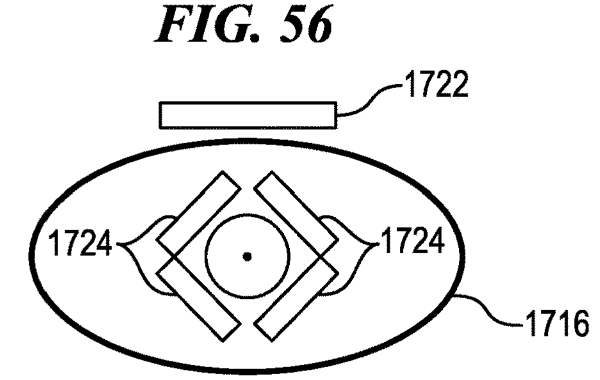
FIG. 56 is a another cross-sectional view of the upper and lower jaws and the tissue of FIG. 55.
Figure 57:
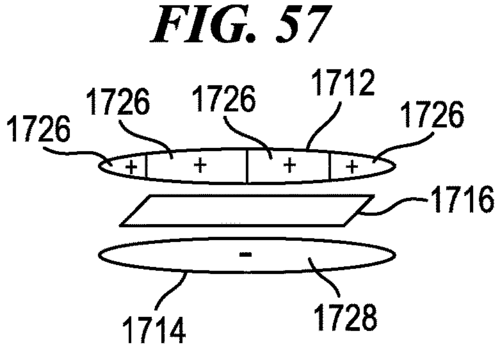
FIG. 57 is a cross-sectional view of yet another embodiment of an electrode configuration of the end effector of FIG. 52 with the upper and lower jaws in a closed position.
Figure 58:
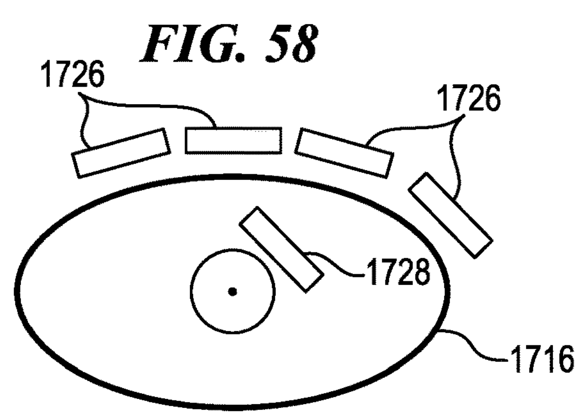
FIG. 58 is another cross-sectional view of the upper and lower jaws and the tissue of FIG. 57.

FIG. 52 illustrates another embodiment of an end effector 1710 including opposed upper and lower jaws 1712, 1714 configured to engage tissue 1716 therebetween. FIG. 52 shows the end effector 1710 closed. One of both of the upper and lower jaws 1712, 1714 includes a segmented electrode. For example, as shown in FIG. 53, FIG. 53A, and FIG. 54, the end effector 1710 can have a multi-source, multi-return configuration in which the upper jaw 1712 includes a segmented positive electrode including four segments 1718 and the lower jaw includes a segmented negative electrode including four segments 1720. Another number of segments can be used. FIG. 53 and FIG. 54 show the end effector 1710 closed. For another example, as shown in FIG. 55 and FIG. 56, the end effector 1710 can have a single-source, multi-return configuration in which the upper jaw 1712 includes one positive electrode 1722 and the lower jaw includes a segmented negative electrode including four segments 1724. Another number of segments can be used. FIG. 55 and FIG. 56 show the end effector 1710 closed. For yet another example, as shown in FIG. 57 and FIG. 58, the end effector 1710 can have a multi-source, single-return configuration in which the upper jaw 1712 includes a segmented positive electrode including four segments 1726 and one negative electrode 1728. Another number of segments can be used. FIG. 57 and FIG. 58 show the end effector 1710 closed.

Controlling electrode power for a segmented electrode can include each of the electrode segments being controlled independently, similar to that discussed above regarding independent control of an ablation device's plurality of electrodes.

Controlling electrode power for an end effector having a dual jaw configuration can include monitoring for collateral thermal damage and using the monitored collateral thermal damage as a control for the power applied to the tissue engaged between the jaws. In general, monitoring for collateral thermal damage includes monitoring at least one parameter, e.g., temperature, impedance, etc., at an external surface of the tissue and controlling power based on the monitored at least one parameter, as discussed herein.

Controlling electrode power for an end effector having a dual jaw configuration can include using an area of tissue engaged between the jaws to monitor one or more parameters of the tissue and using the monitored one or more parameters to control electrode power. In an exemplary embodiment, the parameter(s) are monitored outside an energy zone (similar to an ablation zone) of a particular electrode such that one or more properties of tissue near the tissue intended to be energized by the electrode can be used to control the electrode's power. In other words, tissue not in the return path of the electrode delivering energy can be used in controlling the electrode's power. The nearby tissue may thus be protected from being unintentionally damaged by the electrode's energy delivery while allowing the electrode to apply energy effective to seal the intended tissue. For example, for an end effector engaging tissue between its jaws and including a segmented electrode, tissue contacting one of the segments can be monitored to control another one of the segments.

Examples of the monitored parameter include frequency response, capacitance, pressure, temperature, and impedance. Embodiments of the monitored parameter including at least one of pressure, impedance, and temperature are discussed elsewhere herein. Embodiments of the monitored parameter including at least one of frequency response and capacitance are discussed further below.

Figure 59:
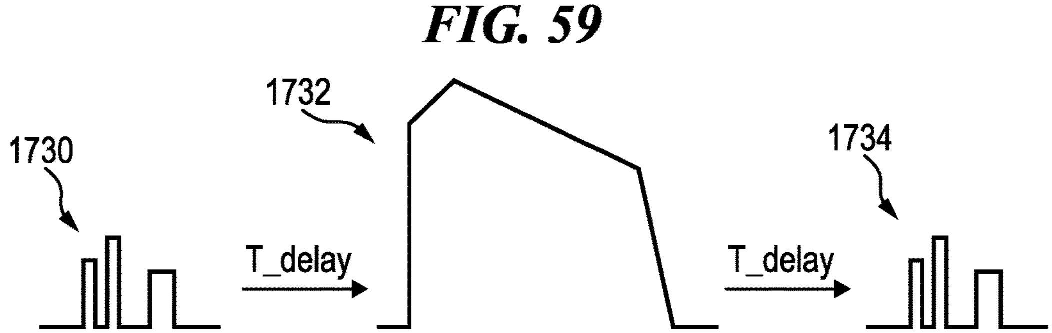
FIG. 59 is one embodiment of a series of pulses that can be applied to tissue.

As mentioned above, one example of a parameter that can be monitored in tissue to control an electrode is frequency response. In some embodiments, frequency response can be used as a detecting or non-therapeutic sweep before or between therapeutic energy applications to tissue engaged by the jaws. FIG. 59 illustrates one embodiment of using frequency response to monitor tissue between therapeutic energy applications. A first low power measurement pulse 1730 (e.g., in a range of about 10 Hz to about 1000 Hz) is applied to tissue near tissue intended to be energized, such as by one electrode segment applying the pulse 1730 to tissue intended to energized by another electrode segment. A controller of a surgical hub, a robotic surgical system or other computer system that is controlling energy delivery can use the first low power measurement pulse to determine a current tissue state using, for example, one or more of implied impedance via voltage/current sampling, signal reflection and measurement (similar to Doppler radar), infrared capacitance measurement, and multiple frequencies. After a time delay T_delay, an energizing, higher frequency treatment pulse 1732 is delivered to the tissue, with the pulse being based on the determined current tissue state. After another time delay T_delay following the delivery of the energizing treatment pulse 1732, a second low power measurement pulse 1734 is applied to tissue near tissue intended to be energized, with the process repeating until energy delivery ceases.

Figure 60:
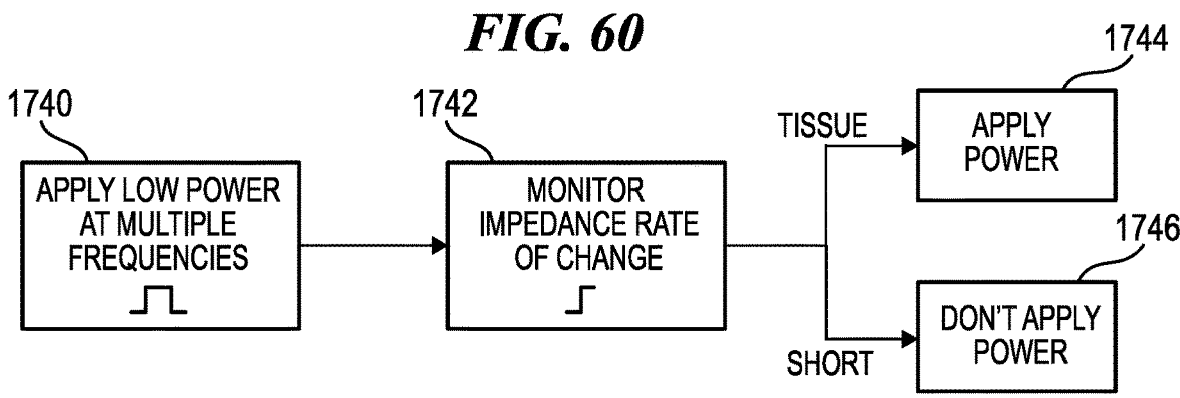
FIG. 60 is a flowchart of one embodiment of a process of using frequency response to monitor tissue between therapeutic energy applications.

FIG. 60 illustrates another embodiment of using frequency response to monitor tissue between therapeutic energy applications. In this illustrated embodiment, nested multi-frequency signals are applied 1740 via one or more electrodes with a discrete therapeutic frequency power level so as to be piggybacked onto the discrete therapeutic frequency power level. FIG. 61 illustrates one embodiment of multi-frequency application using a multiplexor (e.g., on board the surgical device or at a generator supplying energy to the surgical device) and three frequencies. A rate of change of the multi-frequency signals is monitored 1742 and used in controlling electrode power, namely either by determining whether to apply 1744 power or not apply 1746 power. Power is not applied 1746 if there is a short, otherwise power is applied 1744. A source of the multi-frequency signals is known, so the rate of change can be determined, e.g., by a controller of a surgical hub, a robotic surgical system, or other computer system controlling energy delivery. A low frequency pulse (e.g., in a range of about 10 Hz to about 1000 Hz) will have a different lower impedance than the tissue in sweeping the lower frequencies in a low impedance versus short condition. A tissue may respond optimally to a certain frequency over another frequency. An imaging device visualizing the tissue can be used to filter out an appropriate activation frequency.

FIG. 62 shows schematically the process of FIG. 60 using the end effector 1700 of FIG. 51 as an example. A first impedance sensor 1748 measures impedance (local or remote) on a delivery side, and a second impedance sensor 1750 measures impedance (local or remote) on a return side. A low impedance condition differentiates between an electrode short (do not apply 1746 power) versus low impedance (apply 1744 power).

Figures 64, 65:
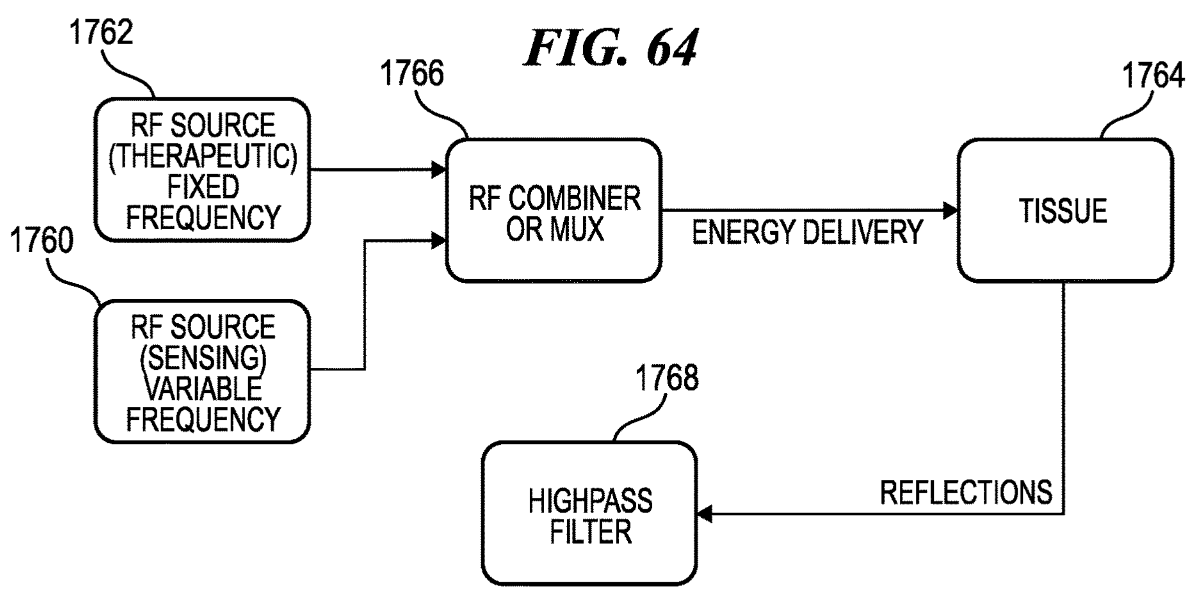
FIG. 64 is a schematic diagram illustrating one embodiment of a process of using the pulses of FIG. 63.
FIG. 65 illustrates one embodiment of a high frequency measurement pulse and a therapeutic treatment pulse that can be applied to tissue.

FIG. 63 and FIG. 64 illustrate another embodiment of using frequency response to monitor tissue. In this illustrated embodiment, a variable frequency measurement pulse 1760 and a therapeutic treatment pulse 1762 at a fixed frequency are applied to tissue 1764 at a same time. A combiner or multiplexor 1766 is used to combined the variable frequency pulse and the therapeutic treatment pulse 1762. Radiofrequency (RF) is used as the energy in this illustrated example but other energy is possible. A high pass filter 1768 differentiates between the high power therapeutic treatment pulse 1762 and the variable frequency sensing pulse 1760. A rate of change of the variable frequency sensing pulse 1760 is used in controlling electrode power similar to that discussed above.

One embodiment of using a high frequency measurement pulse 1780 and a therapeutic treatment pulse 1782 to determine a short (do not apply power) or low impedance (apply power) is illustrated in FIG. 65. FIG. 65 shows the high frequency measurement pulse 1780 relative to the therapeutic treatment pulse 1782 in the time domain. The high frequency measurement pulse 1780 includes four baseline signals in this illustrated embodiment. Typical frequency dependence on permittivity and conductivity of tissues is discussed further in, for example, Miklavčič et al., *Wiley Encyclopedia of Biomedical Engineering*, "Electric Properties of Tissue," John Wiley & Sons, Inc., 2006, p. 1-12, which is hereby incorporated by reference in its entirety.

Figure 66:
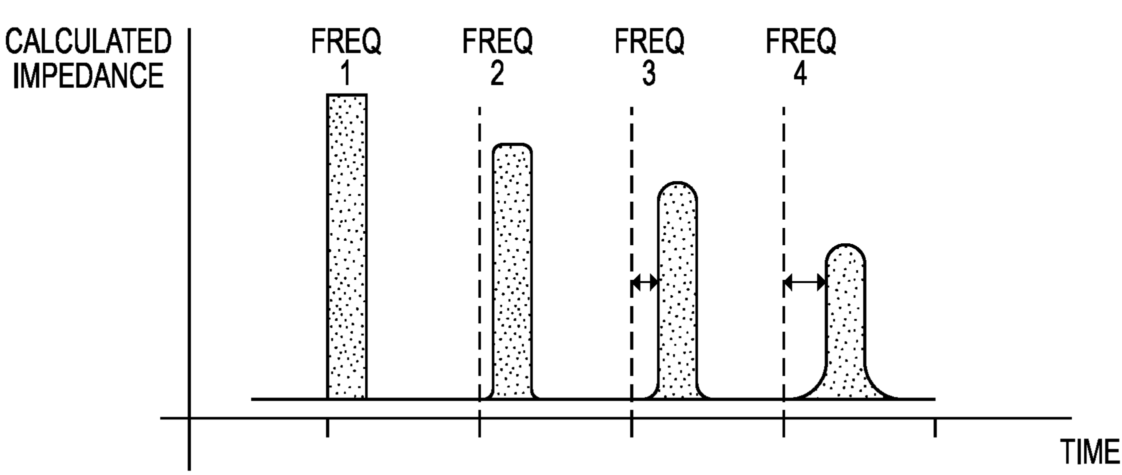
FIG. 66 illustrates a measured acceptable condition of the high frequency measurement pulse of FIG. 65.
Figure 67:
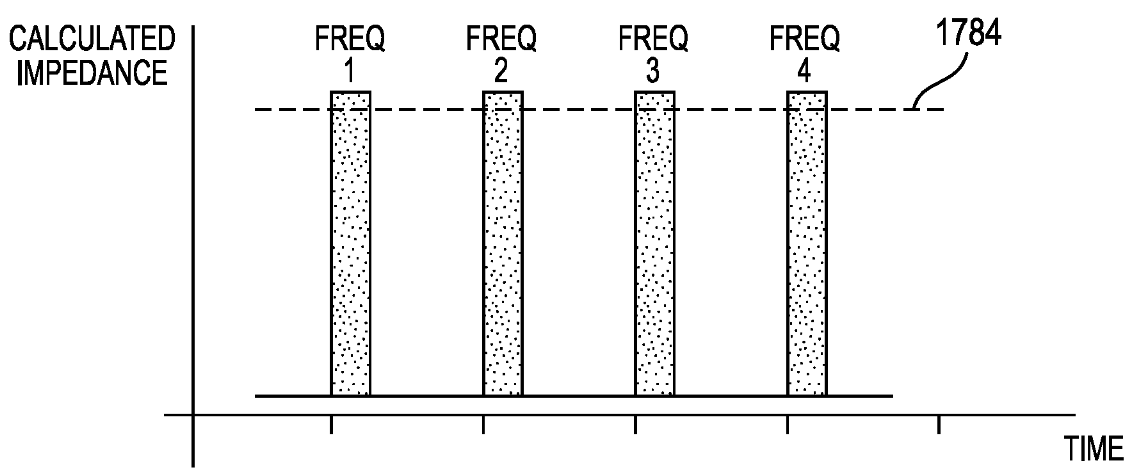
FIG. 67 illustrates a measured fault condition of the high frequency measurement pulse of FIG. 65.
Figure 68:
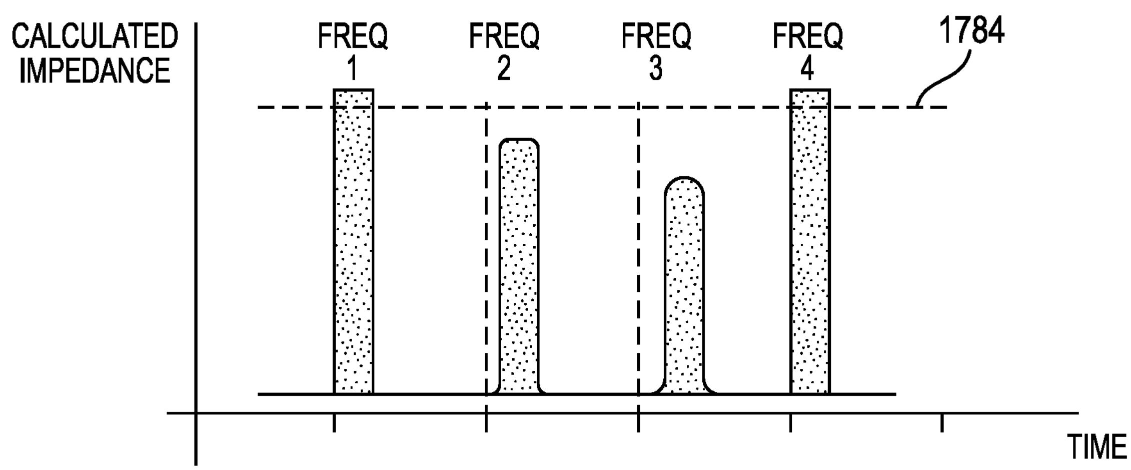
FIG. 68 illustrates a measured marginal condition of the high frequency measurement pulse of FIG. 65.

FIG. 66, FIG. 67, and FIG. 68 illustrate embodiments of a measured acceptable condition, a measured fault condition, and a measured marginal condition, respectively, for the measurement pulse 1780. In the measured acceptable condition, which indicates that power can be delivered, the measured responses show variation in magnitude, phase, and profile across the four baseline signals across various frequencies even with the first frequency signal being unchanged. In the measured fault condition, which indicates that power should not be delivered, the frequency response fails to show a variation below a threshold level 1784, thereby indicating a short. In the measured marginal condition, which indicates that power can be delivered, shorting exists at certain frequencies (frequencies 2 and 3) but not at other frequencies (frequencies 1 and 4). Power delivery may be acceptable because only some frequencies detect a variation while other frequencies do not, so likelihood of a short is small. Some frequencies may fail while others do not due to a condition such as an RF Open presenting as a short due to a quarter wave stub.

Figure 69:
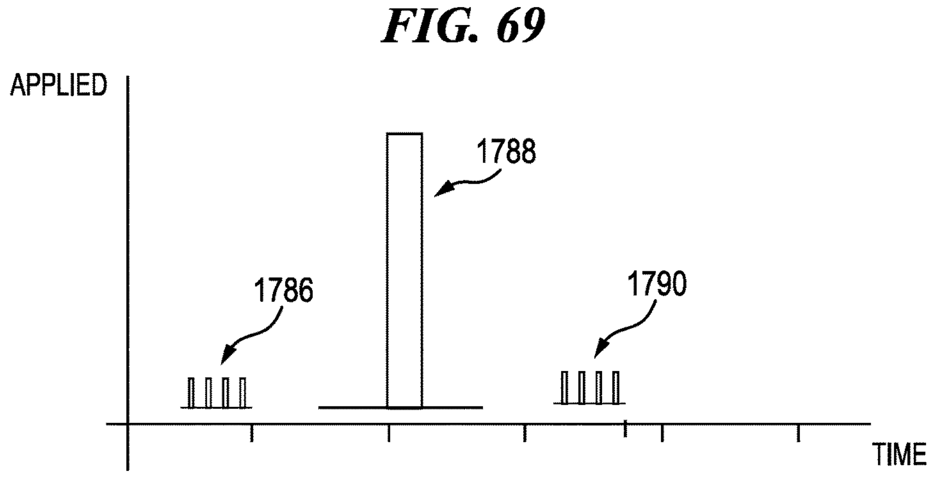
FIG. 69 illustrates one embodiment of first and second measurement pulses and a therapeutic treatment pulse that can be applied to tissue.

Nested multi-frequency signals are applied in the embodiment of FIG. 65 to FIG. 68, but the condition analysis described can be similarly used with a detecting or non-therapeutic sweep before or between therapeutic energy applications. For example, FIG. 69 shows in the time domain a first measurement pulse 1786, a therapeutic treatment pulse 1788 applied after a first time delay, and a second measurement pulse 1790 after a second time delay.

Figure 70:
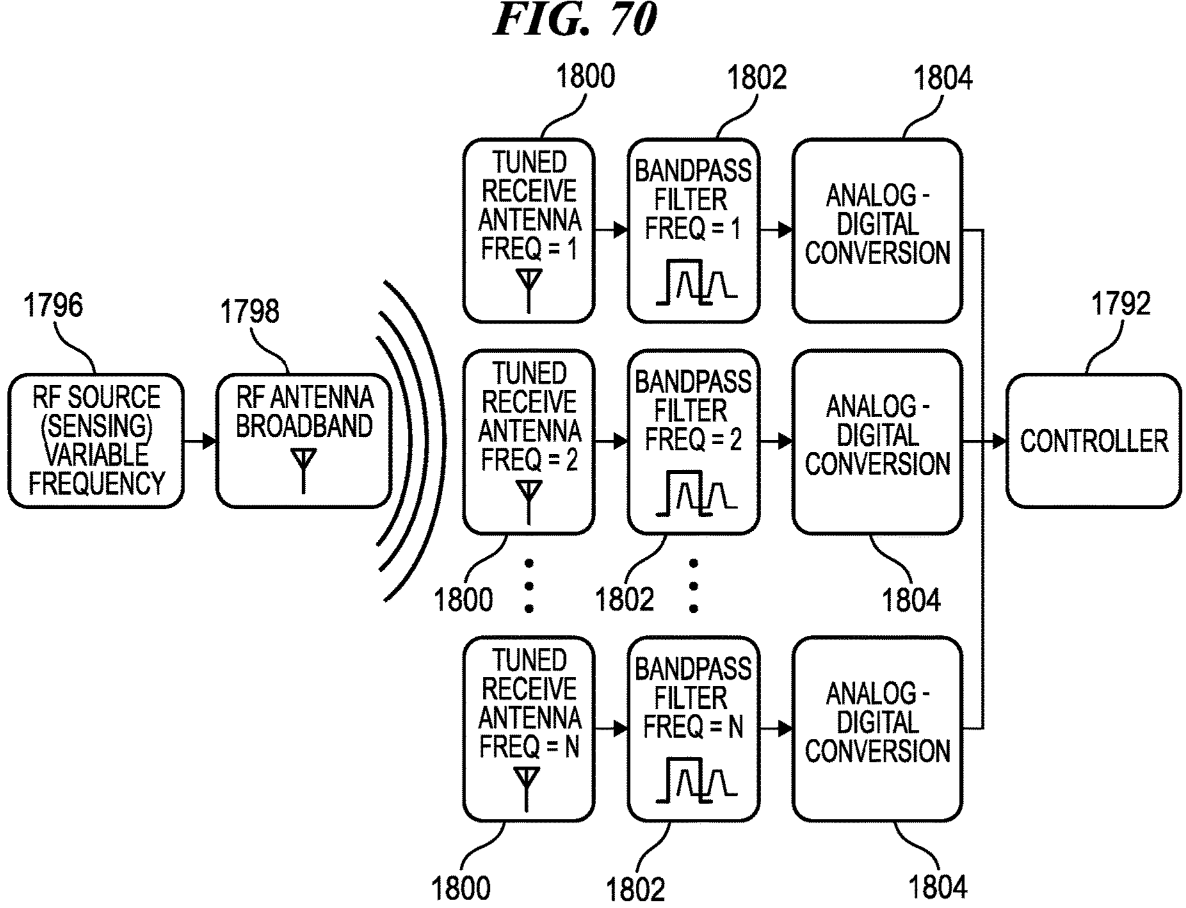
FIG. 70 is a schematic diagram of one embodiment of providing a variable frequency measurement pulse.
Figure 71:
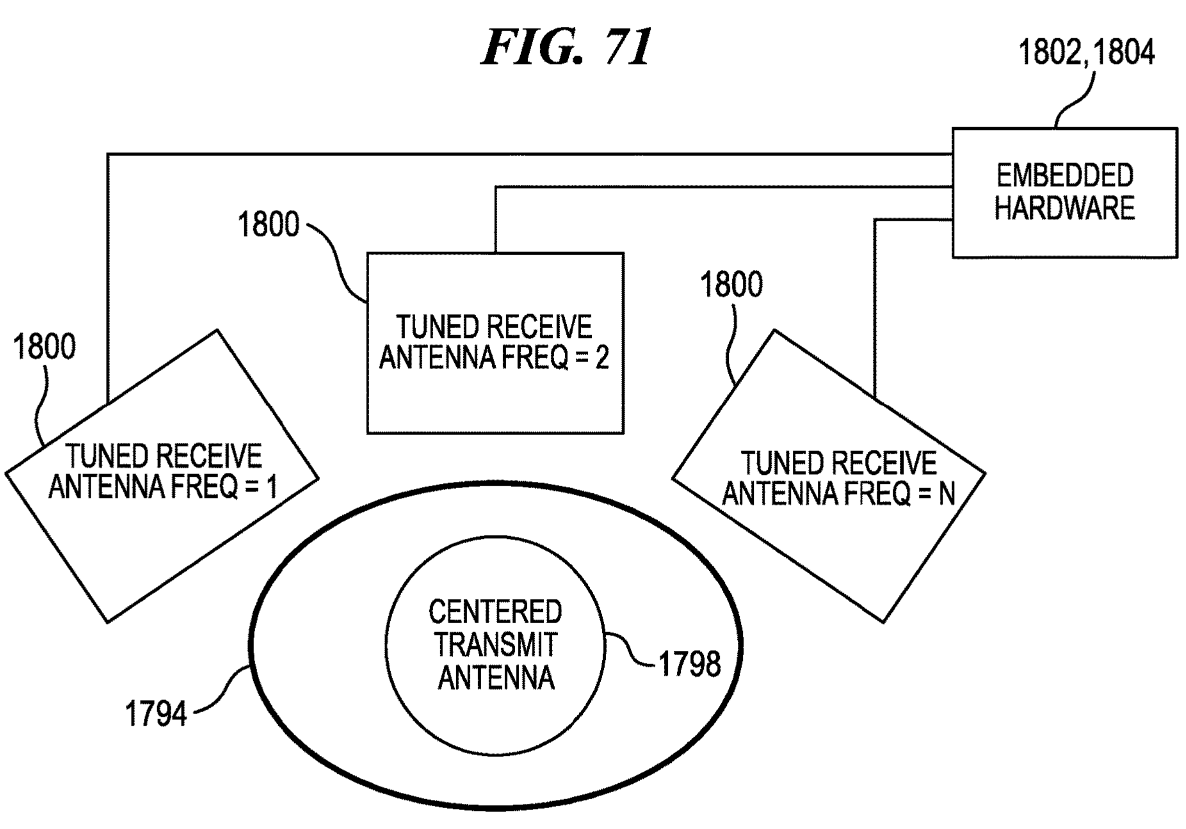
FIG. 71 is another schematic diagram of a portion of the diagram of FIG. 70.

FIG. 70 and FIG. 71 illustrate one embodiment of providing a variable frequency measurement pulse and a controller 1792 (e.g., of a surgical hub, a robotic surgical system, or other computer system) receiving data in response therefrom that the controller can use in determining whether to apply power to tissue 1794. The variable frequency measurement pulse is provided in this illustrated embodiment by an RF source 1796, which may be provided, for example, via an endoscope. The RF source 1796 generates a first frequency (Freq=1) at a first time and loops through additional frequencies from a second frequency (Freq=2) at a second time through an Nth frequency (Freq=N) at an Nth time, where N is an integer greater than two. An RF antenna 1798 broadcasts the generated first through Nth frequencies. Receiver antennas 1800 each tuned to one of the first through Nth frequencies and positioned outside the tissue 1794 receive the signal broadcast at the frequency to which the receiver antenna 1800 is tuned. The received signals each pass through a corresponding tuned bandpass filter 1802 and through an analog-to-digital converter 1804 before being passed to the controller 1792. Since the construction and arrangement of the receiver antennas 1800 is known a priori, the relative positioning of the receiver antennas 1800 to the RF antenna 1798 can be known. Based on changes in signal properties (amplitude and phase delay), the signals received by the controller 1792 provide information regarding the tissue 1794 in the direction indicated by the relative positioning.

As mentioned above, one example of a parameter that can be monitored in tissue to control an electrode of a dual jaw end effector is capacitance. Dielectric change can be used to determine a type of the tissue engaged by the jaws and to control electrode power. A non-therapeutic RF signal, e.g., a signal with power below the level that induces therapeutic effects on the tissue, can be delivered to the tissue, e.g., by an electrode on one of the jaws, to determine a density or a change of tissue type along the jaws. A ratio of power in the electrode to capacitance of tissue adjacent to the electrode can be used to balance pressure, conductivity, or power.

For example, tissue engaged by the jaws can have variable compressibility and thickness due to adhesions or chronic disease. Measuring a rate of change of capacitance adjacent to the electrode that will deliver therapeutic energy can be used to determine between variation of pressure or variation of power to complete the electrode weld. Upper and lower thresholds can be used to induce different effects.

For another example, resistance versus parasitics (parasitic capacitance and parasitic inductance) can be measured during energy application, as the ratio may change during the energy application due to the tissue's variable compressibility and thickness. Power delivery may therefore not be as expected. A shift in frequency of the power based on the ratio may minimize the parasitic leaching effect. The tissue could have a high impedance at low frequency, a low impedance at high frequency, or vice versa, which enables the controller to tune the frequency to the tissue to improve the power level's effectiveness on the tissue.

Providing a variable frequency measurement pulse that can be received by a tuned antenna array, similar to that discussed above regarding FIG. 70, may allow for detection of the tissue's orientation and properties. Also, filters may be used as part of the electrodes, which may allow the RF source, e.g., a generator, to have full output with the filters controlling measures.

In some embodiments in which one or more parameters of tissue are monitored, a previously sealed area of tissue can be used to monitor and control sealing of an adjacent area of the tissue. A previously sealed area of tissue has functional characteristics of a denatured zone having higher impedance and lower conductivity since collagen has already fused and water has been removed, thereby allowing for a more stable measurement albeit a measurement that may be less sensitive. In some embodiments in which one or more parameters of tissue are monitored, an area of tissue that has not yet been sealed or that is not intended for sealing (non-targeted tissue) can be used to monitor and control sealing of an adjacent area of the tissue. Such a tissue area not yet sealed will have more water, a higher conductivity, and lower impedance than a previously sealed area of tissue and will therefore be more sensitive to monitoring effects of the adjacent area of tissue. In some embodiments in which one or more parameters of tissue are monitored, both a previously sealed area of tissue and an area of tissue that has not yet been sealed or that is not intended for sealing can be used to monitor and control sealing of an adjacent area of the tissue.

Monitoring tissue adjacent an area of tissue to be sealed can be accomplished, for example, using a first, non-therapeutic set of electrodes on an edge of a jaw of the end effector, while a second, therapeutic set of electrodes on the jaw located radially inward of the first set of electrodes can be used to seal the intended, targeted tissue. The non-therapeutic set of electrodes can "float" on the energized state of the therapeutic circuit. An isolation element such as a transformer can be used to power the non-therapeutic set of electrodes.

The therapeutic set of electrodes can have a high impedance coating to prevent therapeutic high power flow through while allowing for low current sensing. An aspect of the high impedance coating can be characterized to determine if an individualized resistive fingerprint would be able to respond to the higher sensing signal.

Controlling electrode power for an end effector having a dual jaw configuration can include monitoring a power parameter or electrode aspect of the surgical device's connection to a return path or a generator supplying energy to the surgical device, thereby allowing distally controlled power delivery to be monitored. Return loss monitoring (remote monitoring away from the surgical site) may therefore be performed for a monopolar array.

Optimizing impedance of the source with the tissue may maximize effective power delivery to the surgical device by allowing an inadvertent change of tissue path return to be identified. A ratio of the delivered power (power supplied to the surgical device) and the reflected power (power returned back from the surgical device) can match impedance to the patient, which may allow for maximum power efficiency. If delivery efficiency is detected to suddenly shift, the energy focal point is likely to have shifted. Current would show an inadvertent short to trigger power level adjustment, while impedance would show an inadvertent change of tissue path return and not trigger power level adjustment.

Scope and Electrode Location Monitoring and Control

Devices, systems, and methods for multi-source imaging provided herein may allow for scope and electrode location monitoring and control.

As discussed herein, a surgical procedure can include a scope and an ablation device positioned in a hollow organ or a body lumen that is being visualized from an external point of view (extraluminal visualization) using an imaging device. For example, in a DMR procedure, a scope such as an endoscope can be positioned in a duodenum, an ablation device including an electrode (which may be a single electrodes or a plurality of electrodes) can be positioned in a duodenum distal to the scope, and an imaging device such as a laparoscope can be positioned external to the duodenum. In other surgical procedures, the scope and the ablation device can be positioned in a different hollow organ or body lumen.

The scope and the ablation device within the hollow organ or body lumen can be difficult to visualize from within the hollow organ or body lumen, e.g., due to curvature of the hollow organ or body lumen and/or due to the limited space within the hollow organ or body lumen to allow an imaging device to be positioned within the hollow organ or body lumen to achieve a full view or even a partial view of the scope and/or the ablation device. Therefore, it can be difficult to determine whether the electrode(s) of the ablation device are properly positioned before being energized to ablate target tissue within the hollow organ or body lumen because the location of the electrode(s) may not be known, and/or it can be difficult to determine that each intended target of ablation within the hollow organ or body lumen has been ablated as intended because it may not be known whether the scope has moved enough within the hollow organ or body lumen to allow the ablation device to access and ablate each target.

The imaging device's visualization of the scope and/or the ablation device from outside the hollow organ or body lumen can be used to determine a location of the scope and/or the ablation device within the hollow organ or body lumen. A location of electrode(s) of the ablation device can thus be determined before the electrode(s) are energized to ablate target tissue within the hollow organ or body lumen and/or while the electrode(s) are energized and ablating target tissue, which may help ensure that the electrode(s) are properly located to ablate the target tissue. In addition to or instead of determining the location of the scope and/or the ablation device, the imaging device's visualization of the scope and/or the ablation device can be used to control movement of the scope and/or the ablation device within the hollow organ or body lumen, which may help ensure that each intended target of ablation within the hollow organ or body lumen is reached for ablation.

In some embodiments, scope and electrode location monitoring and control can include controlling scope movement based on at least one parameter monitored from outside a hollow organ or body lumen in which the scope is positioned. An imaging device positioned outside the hollow organ or body lumen can be configured to gather images, as discussed herein, and thereby monitor the at least one parameter. A controller in communication with the imaging device and the scope can receive a signal from the imaging device regarding the monitored parameter(s). The controller can receive the signal directly from the imaging device or through one or more intermediary devices. As discussed above, an algorithm stored on board the scope or stored elsewhere can include one or more variable parameters. The controller can be configured to adjust at least one variable parameter of the algorithm based on the monitored parameter(s), as indicated by the received signal. The at least one variable parameter can be related to movement of the scope within the hollow organ or body lumen, such as advancement rate (rate of distal movement) or retraction rate (rate of proximal movement). Movement of the scope can thus be controlled based on information gathered by the imaging device despite the imaging device being located outside the hollow organ or body lumen in which the scope is positioned. Consequently, a location of an ablation device advanced through the scope and/or advanced outside the scope and positioned distal to the scope can thus also be controlled, which may help ensure that each intended target for ablation is ablated.

The parameter monitored using the imaging device's visualization can include one or more of, for example, tissue temperature, current flow in tissue, tissue impedance, tissue thickness, and tissue water density. For example, the imaging device can be configured to gather thermal information using, e.g., an infrared (IR) camera, to monitor a temperature of an external surface of the hollow organ or body lumen in which the scope and the ablation device are located. The images can be gathered while the ablation device is delivery energy to the tissue, e.g., using one or more electrodes contacting an internal surface of the tissue, so as to be heating the tissue. In response to the external temperature reaching a predetermined maximum threshold, the controller can cause the scope and/or the ablation device to move, e.g., to be retracted, and can adjust at least one variable parameter of the algorithm to adjust a rate of the scope's and/or ablation device's movement based on a rate of change of the monitored temperature. Monitoring the tissue's temperature using IR thermal imaging can also be used to determine a width of the energy seal provided by the ablation based on the starting and stopping temperatures monitored.

FIG. 28 illustrates one embodiment in which thermal information gathered by an imaging device can be used to control position of the ablation device. As discussed above, FIG. 28 illustrates an ablation device (ablation probe) 1440 positioned in a lung and illustrates an imaging device 1444 that is positioned outside the lung and that is configured to gather images using at least infrared light, e.g., by using an IR camera. As indicated in the graph of FIG. 28, the IR thermal camera monitors the temperature of an external surface of the lung as shown by the "Lung Tissue" line in the temperature versus time portion of the graph. The graph also shows position of the ablation device 1440 versus time. In response to the measured external surface temperature at time $t_2$ reaching a predetermined maximum threshold, which is 41° C. in this illustrated embodiment, the ablation device's position is changed, such as by a controller of a surgical hub, a robotic surgical system, or other computer system causing movement of the ablation device or of a scope in which the ablation device 1440 is located. At time $t_2$, the ablation device 1440 is shown in the graph to move in the x, y, and z dimensions. In response to the measured external surface temperature at time $t_4$ again reaching the predetermined maximum threshold, the ablation device's position is again changed. At time $t_4$, the ablation device 1440 is shown in the graph to move in the y and z dimensions.

In some embodiments, scope and electrode location monitoring and control can include controlling a centering of an ablation device's electrodes within a hollow organ or body lumen.

As discussed herein, an ablation device can include a plurality of electrodes. For example, the ablation device 1410 of FIG. 23 can include a plurality of electrodes attached to the balloon 1412. For another example, the ablation device 1490 of FIG. 34 includes a plurality of electrodes. For yet another example, the ablation device 1500 of FIG. 37 includes a plurality of electrodes 1506.

Figure 72:
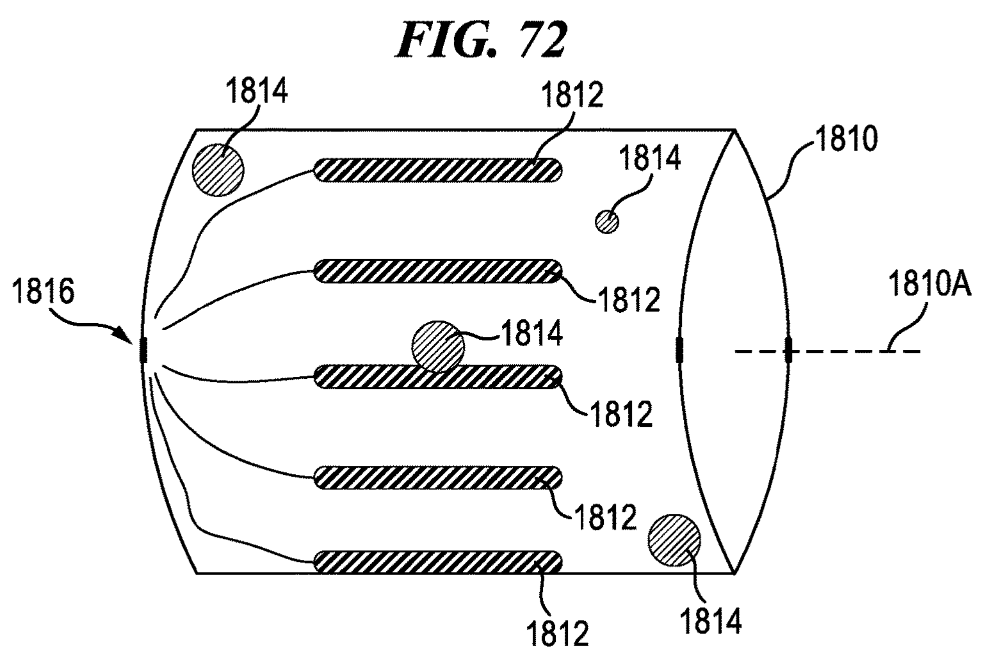
FIG. 72 is a perspective view of a distal portion of another embodiment of an ablation device.

For still another example, as shown in FIG. 72, an ablation device can include a balloon 1810 and a plurality of electrodes 1812. FIG. 72 shows a longitudinal axis 1810A of the balloon 1810, which is coaxial with a longitudinal of the ablation device. The electrodes 1812 are segmented in this illustrated embodiment so can be independently controlled, such as by providing power to only certain ones of the electrodes 1812 via power lines extending distally for operative coupling with a power supply. The balloon 1810 in this illustrated embodiment is formed of a flexible circuit material. The electrodes 1812 in this illustrated embodiment are spaced equidistantly around a circumference of the balloon 1810 and are printed on an outer surface of the flexible circuit material.

The ablation device in this illustrated embodiment also includes a plurality of fiducial markers 1814 that are printed on the outer surface of the flexible circuit material. The fiducial markers 1814 can be otherwise applied to the balloon's outer surface, such as being a small coil adhered to the outer surface of the balloon 1810 (in which case the material can but need not be flexible circuit material). The balloon 1810 is configured to selectively expand and compress by selectively introducing fluid into and withdrawing fluid from an interior of the balloon 1810. The balloon 1810 is enclosed except at a valve 1816 that can be selectively opened to allow fluid introduction and withdrawal. In some embodiments, the fluid can be hot water, which when inside the balloon 1810 can heat the electrodes 1812 enough for the electrodes 1812 to ablate tissue without being supplied with energy from a power supply.

Centering an ablation device's electrodes within a hollow organ or body lumen may help maximize contact of each of the electrodes against an interior surface of the hollow organ or body lumen, thereby helping to ensure that ablation occurs around an entire inner circumference of the hollow organ or body lumen. A longitudinal axis of the ablation device's balloon or other expandable member can be used in centering the ablation device's electrodes within the hollow organ or body lumen since the electrodes are attached to the balloon or other expandable member. Coaxially aligning the longitudinal axis of the ablation device's balloon or other expandable member with a longitudinal axis of the hollow organ or body lumen in which the ablation device is positioned will center the ablation device's electrodes within a hollow organ or body lumen. The hollow organ or body lumen's longitudinal axis can be known through imaging, such as via visualization provided by the imaging device positioned outside the hollow organ or body lumen, and/or by a centered projection line visualized by the imaging device. The projection line can be projected distally, for example, by a scope through which the ablation device has been advanced and from which the ablation device distally extends. A controller of a surgical hub, a robotic surgical system, or other computer system in communication with the imaging device can thus know each of the hollow organ or body lumen's longitudinal axis and the longitudinal axis of the ablation device's balloon or other expandable member, thereby allowing the controller to move the ablation device so the longitudinal axes are coaxially aligned and thus so the electrodes are centered.

The ablation device's electrodes can be centered in a variety of ways. For example, each of the electrodes can be configured to emit a low level electromagnetic pulse. The imaging device located outside the hollow organ or body lumen in which the ablation device is located can receive the emitted pulses, such as with an electromagnetic sensor, to allow each of the electrode's positions to be determined, such as by a controller of a surgical hub, a robotic surgical system, or other computer system in communication with the imaging device, since a strength of the magnetic field indicates relative distances of each electrode to the receiver. Based on the electrodes' positions, the controller can cause the ablation device to move within the hollow organ or body lumen to center the electrodes.

For another example, each of an ablation device's fiducial markers can be magnetic and used to detect location of the ablation device. The fiducial markers can, for example, be attached to the ablation device's balloon or other expandable member. The imaging device located outside the hollow organ or body lumen in which the ablation device is located can include a magnetoresistive sensor configured to determine location of the fiducial markers, and thus location of the balloon or other expandable member and the electrodes thereon, based on the magnetic signatures of the fiducial markers. Based on the balloon or other expandable member's position, the controller can cause the ablation device to move within the hollow organ or body lumen to center the electrodes.

A location of the fiducial markers can facilitate determination of the balloon or other expandable member's location and thus facilitate determining location of the electrodes. For example, in the embodiment of FIG. 72, a first fiducial marker 1814 (in an upper left position in the view of FIG. 72) is positioned at a rear or proximal end of the balloon 1810, a second fiducial marker 1814 (in a bottom right position in the view of FIG. 72) is positioned at a front or distal end of the balloon 1810, a third fiducial marker 1814 (in a center position in the view of FIG. 72) is positioned equidistantly between the front and rear ends of the balloon 1810, and a fourth fiducial marker 1814 is positioned at a front or distal end of the electrodes 1812. The fourth fiducial marker 1814 positioned relative to the electrodes 1812 for facilitating determination of electrode location has a smaller size than the first, second, and third fiducial markers 1814 positioned relative to the balloon 1810 for facilitating determination of balloon 1810 location. The fiducial markers 1814 can be detected as discussed herein, thereby allowing the controller to determine a location of the balloon 1810, e.g., based on the larger first, second, and third fiducial markers 1814, and a location of the electrodes 1812, e.g., based on the centered, third and the smaller, fourth fiducial markers 1814. In some embodiments, the fourth fiducial marker 1814 and/or the third fiducial marker 1814 can be omitted, while in other embodiments, the first, second, and third fiducial markers 1814 can be omitted.

In some embodiments, scope and electrode location monitoring and control can include detecting completion of ablation to determine when to stop supplying power to the ablation device's electrode(s) so as to stop ablation. For example, CT imaging provided by an imaging device positioned outside the hollow organ or body lumen in which the ablation device is positioned can gather thermal images indicative of tissue temperature. The CT imaging device can be located entirely outside the patient, such as with intraoperative CT imaging using a C-arm. In response to the measured temperature reaching a predetermined maximum temperature indicative of ablation completion, power can stop being supplied to the ablation device's electrode(s).

In some embodiments, scope and electrode location monitoring and control can include using a magnet. The magnet can allow for determining movement and/or location, and/or can for determining tissue thickness.

Figure 73:
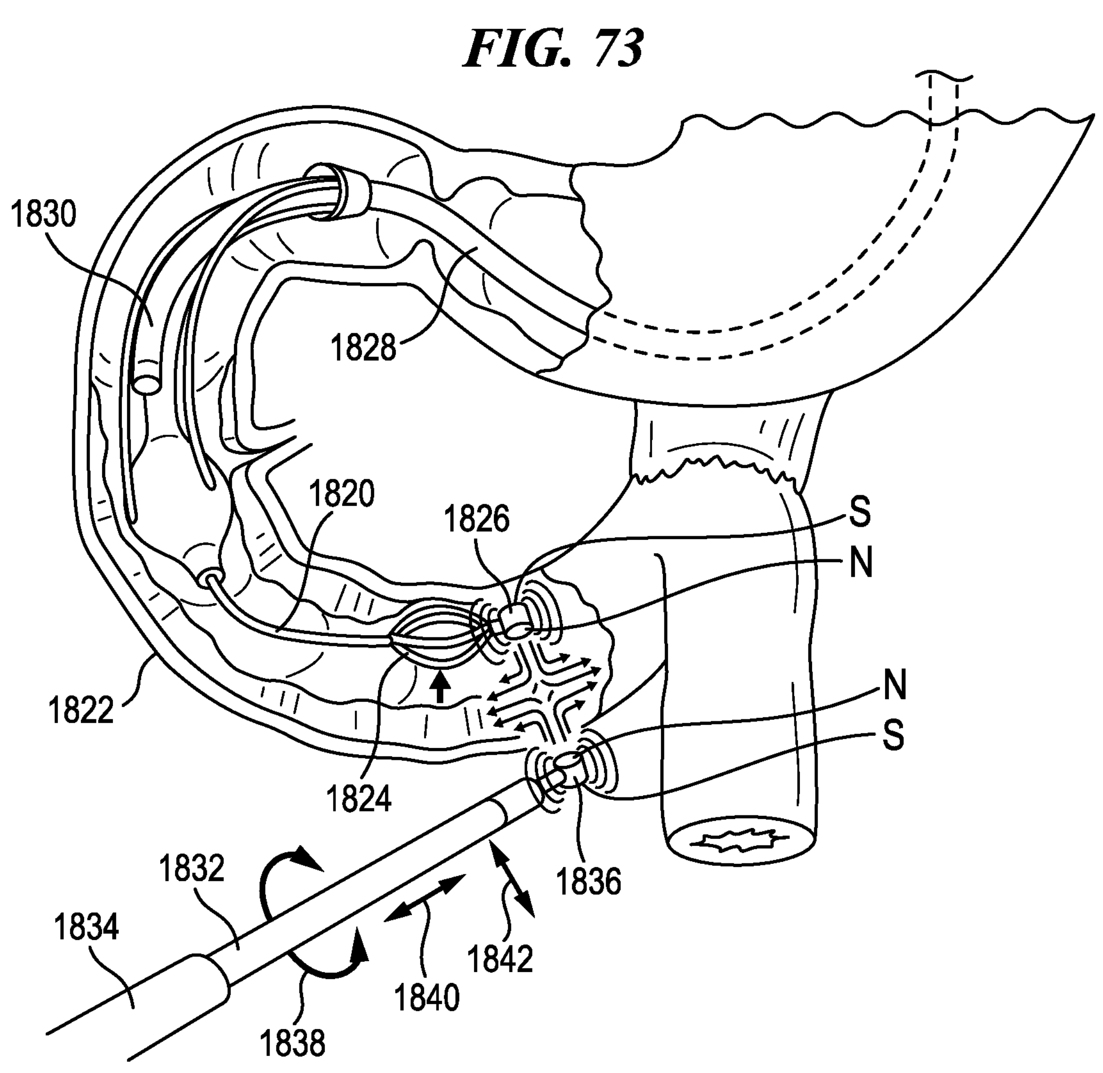
FIG. 73 is a perspective partial cross-sectional view of one embodiment of an ablation device including a first magnet positioned inside a duodenum and a surgical device including a second magnet positioned outside the duodenum.

FIG. 73 illustrates one embodiment of location monitoring and control using a magnet. FIG. 73 shows an ablation device 1820 positioned in a duodenum 1822 of a patient, but a magnet can be similarly used in other hollow organs and body lumens. The ablation device 1820 includes an expandable member 1824, in the form of a basket, to which a plurality of electrodes are attached. A first magnet 1826 is at a distal tip of the ablation device 1820 distal to the expandable member 1824. South (S) and north (N) poles of the first magnet 1826 are shown in FIG. 73.

An ablation device can be advanced into a hollow organ or body lumen through an overtube and/or a scope (e.g., a working channel of the scope). In this illustrated embodiment, the ablation device 1820 is advanced into the duodenum 1822 through an overtube 1828. An endoscope 1830 has also been advanced through the overtube 1828 and is also positioned in the duodenum 1822. However, the endoscope 1830 cannot visualize the expandable member 1824 (or any of the electrodes attached thereto) as positioned in FIG. 73 due to the curvature of the duodenum 1822 and the relative positions of the endoscope 1830 and the expandable member 1824.

As shown in FIG. 73, a surgical device 1832 is positioned outside of the duodenum 1822. The surgical device 1832 can be so positioned in any of a variety of ways, such as by being advancing laparoscopically through a laparoscope 1834, as in this illustrated embodiment. The surgical device 1832 includes a second magnet 1836 at a distal tip thereof. South (S) and north (N) poles of the second magnet 1836 are shown in FIG. 73. The second magnet 1836 is configured to be moved outside the duodenum 1822 to cause movement of the first magnet 1826, and thus the expandable member 1824 and the electrodes, within the duodenum 1822 by magnetically interacting with the first magnet 1826. The second magnet's movement can be any combination of rotation (shown by a first arrow 1838), translational movement (shown by a second arrow 1840), or lateral movement (shown by a third arrow 1842).

Figure 74:
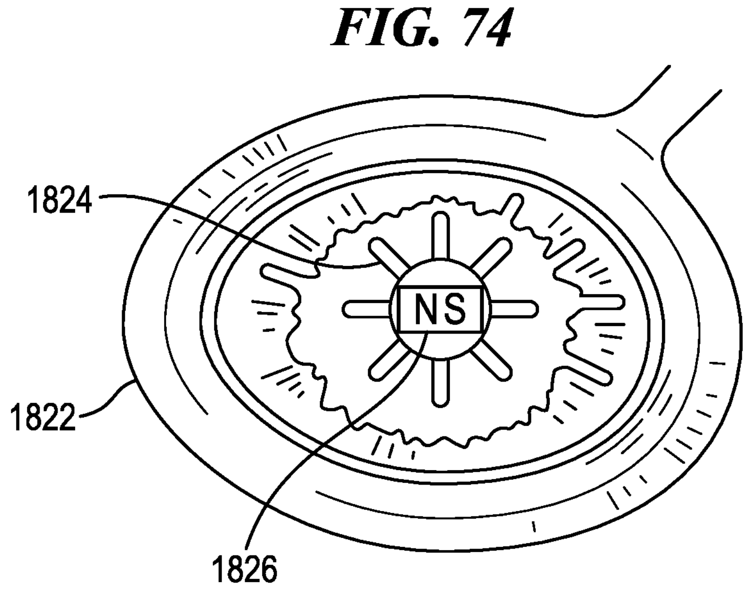
FIG. 74 is a cross-sectional view of the first magnet of FIG. 73 in a passive configuration in the duodenum.

The movement of the first magnet 1826 in response to the movement of the second magnet 1836 depends on a relative position of the north and south poles of the first and second magnets 1826, 1836. FIG. 74 illustrates the first magnet 1826 in the duodenum 1822 in a passive configuration in which the second magnet 1836 is not magnetically interacting with the first magnet 1826. FIG. 75 illustrates the first magnet 1826 in the duodenum 1822 in an attraction configuration in which the second magnet 1836 is positioned relative to the first magnet 1826 such that the first magnet 1826 is attracted to the second magnet 1836. Therefore, the first magnet 1826, and thus the expandable member 1824 and the electrodes attached thereto, have moved closer to an interior wall of the duodenum 1822 in a direction toward the second magnet 1836. In FIG. 75 the first magnet 1826 is attracted to the second magnet 1836 by the south (S) pole of the second magnet 1836 being positioned adjacent to the north (N) pole of the first magnet 1826 with a tissue wall of the duodenum 1822 being positioned therebetween. Instead of the south (S) pole of the second magnet 1836 being positioned adjacent to the north (N) pole of the first magnet 1826 in the attraction configuration, the north (N) pole of the second magnet 1836 can be positioned adjacent to the south (S) pole of the first magnet 1826. FIG. 76 illustrates the first magnet 1826 in the duodenum 1822 in a repulsion configuration in which the second magnet 1836 is positioned relative to the first magnet 1826 such that the first magnet 1826 is repulsed by the second magnet 1836. Therefore, the first magnet 1826, and thus the expandable member 1824 and the electrodes, have moved closer to the interior wall of the duodenum 1822 in a direction away from the second magnet 1836. FIG. 76 also shows with a fourth arrow 1844 (similar to the first arrow 1838) that the second magnet 1836 has been rotated from its position in FIG. 75 so as to cause the first magnet's movement from the attraction configuration to the repulsion configuration. In FIG. 76 the first magnet 1826 is repulsed by the second magnet 1836 by the north (N) pole of the second magnet 1836 being positioned adjacent to the north (N) pole of the first magnet 1826 with a tissue wall of the duodenum 1822 being positioned therebetween. Instead of the north (N) pole of the second magnet 1836 being positioned adjacent to the north (N) pole of the first magnet 1826 in the repulsion configuration, the south (S) pole of the second magnet 1836 can be positioned adjacent to the south (S) pole of the first magnet 1826.

In some embodiments, a magnetic element can be attached to an ablation device configured to be positioned within a hollow organ or body lumen, such as in the embodiment of FIG. 73. In other embodiments, a magnetic element can be attached to a scope configured to be positioned within a hollow organ or body lumen. The magnetic element being attached to the scope may allow a location of the scope to be tracked within the hollow organ or body lumen from outside the body lumen and/or may allow tissue thickness to be determined.

Figure 77:
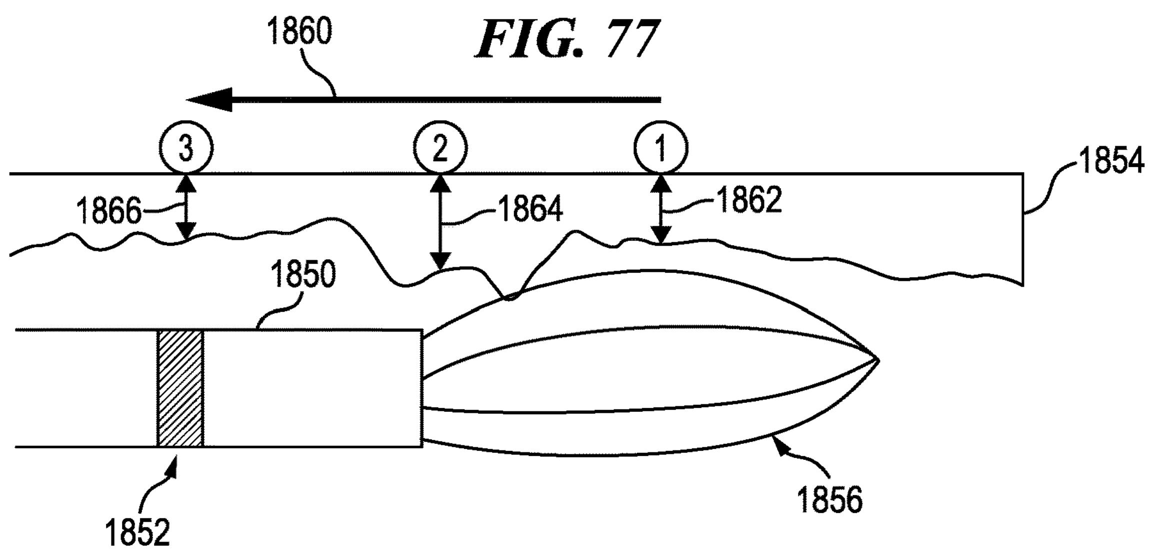
FIG. 77 is a side schematic partial cross-sectional view of another embodiment of an ablation device extending distally from a scope located within a hollow organ or body lumen.
Figure 78:
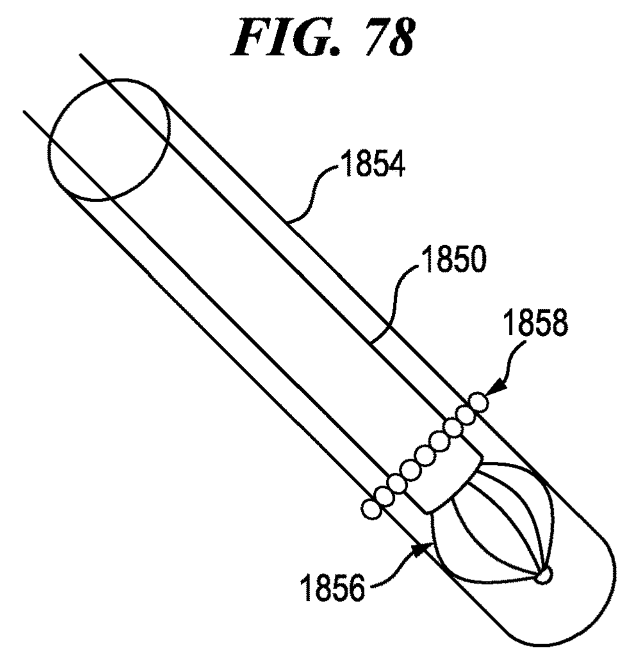
FIG. 78 is a perspective partial transparent view of the scope and the ablation device of FIG. 77 with a magnet positioned around an external surface of the hollow organ or body lumen.

FIG. 77 illustrates one embodiment of a scope 1850 that includes a first magnet 1852. The first magnet 1852 in this illustrated embodiment is in the form of a magnetic collar extending circumferentially around the scope 1850 just proximal to a distal end of the scope 1850. FIG. 77 and FIG. 78 show the scope 1850 positioned within a hollow organ or body lumen 1854 and with an expandable member 1856, in the form of a basket, of an ablation device extending distally from the scope 1850. The first magnet 1852 is configured to be magnetically detected from outside the hollow organ or body lumen 1854 using a second magnet 1858. The second magnet 1858 in this illustrated embodiment includes a plurality of magnets in a chain configured to be wrapped circumferentially around an external surface of the hollow organ or body lumen 1854, as shown in FIG. 78. The second magnet 1858 can be wrapped around the external surface in a variety of ways, such as similar to that discussed above regarding a sleeve or stent being positioned around a hollow organ or body lumen's outer diameter.

Figure 79:
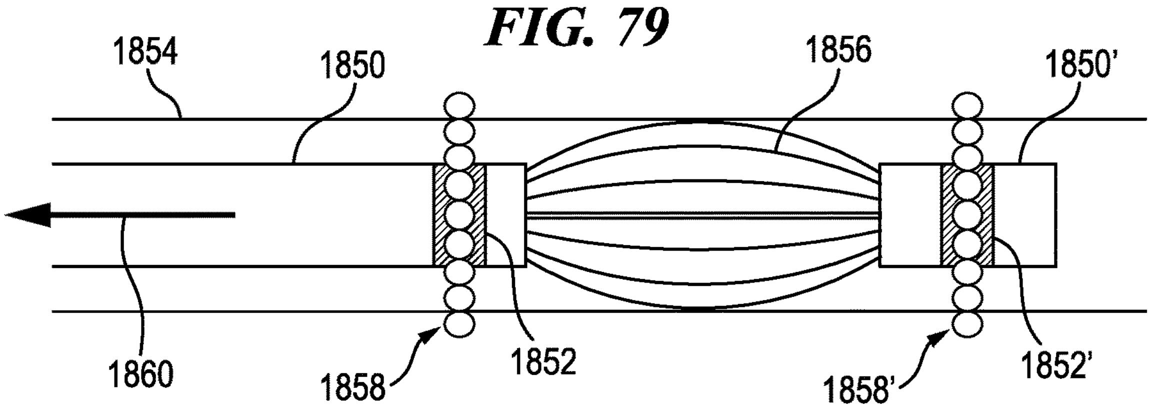
FIG. 79 is a side schematic partial cross-sectional view of the scope, the ablation device, and the magnet moved between first and second positions.

The second magnet 1858 is configured to move along the hollow organ or body lumen's external surface corresponding to movement of the scope 1850, and thus of the first magnet 1852, within the hollow organ or body lumen 1854 due to the attraction of the first and second magnets 1852, 1858. FIG. 79 illustrates one embodiment of scope 1850 movement within the hollow organ or body lumen 1854. The scope 1850 is retracted proximally from a first, distal position to a second, proximal position as shown by an arrow 1860. The first and second magnets 1852, 1858 thus also move proximally. The first, distal position of the scope 1850', the first magnet 1852', and the second magnet 1858' is noted by those elements being numbered with an apostrophe.

A first magnet positioned within a hollow organ or body lumen and a second magnet positioned outside the hollow organ or body lumen with a tissue wall located between the first and second magnets are configured to cooperate to allow determination of a thickness of the tissue wall. A strength of magnetic attraction between the first and second magnets will vary based on a thickness of the tissue wall therebetween. Thus, strength of the magnetic attraction at different locations along an axial length of the hollow organ or body lumen can indicate a thickness of the tissue wall at that location.

Figure 80:
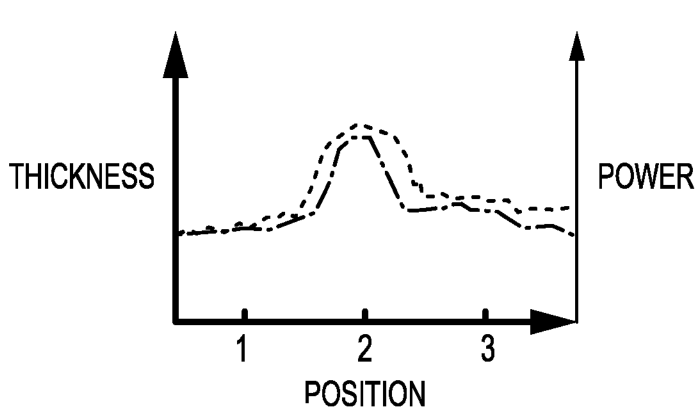
FIG. 80 is a graph showing tissue thickness and magnetic attraction for three positions of the scope of FIG. 77.

For example, the first and second magnets 1852, 1858 of FIG. 77 to FIG. 79 are configured to allow determining thickness of the hollow organ or body lumen 1854 positioned between the first and second magnets 1852, 1858. As shown in FIG. 77, a thickness of the hollow organ or body lumen 1854 is different at different axial locations along a length of the hollow organ or body lumen 1854. The tissue has a first thickness 1862 at a first axial location (1), a second thickness 1864 at a second axial location (2) proximal to the first axial location (1), and a third thickness 1866 at a third axial location (3) proximal to the second axial location (2). In this illustrated embodiment the first thickness 1862 is less than the third thickness 1866, which is less than the second thickness 1868. As the scope 1850 is retracted (moved proximally) within the hollow organ or body lumen 1854, as discussed above, the magnetic attraction between the first and second magnets 1852, 1858 varies as indicated in a graph shown in FIG. 80 plotting tissue thickness and power (magnetic attraction) for each of the first, second, and third positions (1), (2), (3). Different magnetic attractions between the first and second magnets 1852, 1858 are known for each of a plurality of different tissue thicknesses, so detected magnetic attractions can be correlated to known tissue thicknesses, such as by using a lookup table stored in a memory accessible to a controller of a surgical hub, a robotic surgical system, or other computer system.

Figure 81:
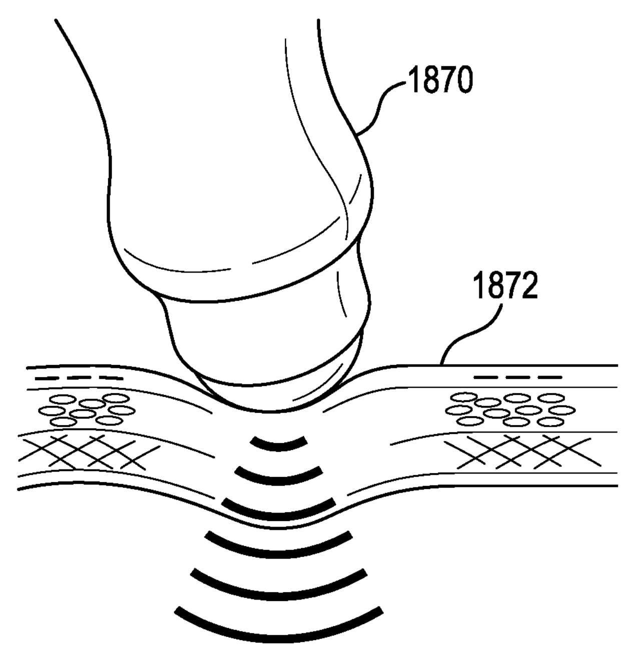
FIG. 81 is a side partial cross-sectional view of an ultrasound imaging device visualizing through a tissue wall.

In addition to or instead of using a magnet for scope and electrode location monitoring and control, ultrasound imaging can be used to determine scope and/or electrode location. The ultrasound imaging can be used to locate a scope and/or electrode(s) within a hollow organ or body lumen. The magnet can then be positioned outside the hollow organ or body lumen near the determined location and used to control electrode movement, as discussed above. Additionally or alternatively, the ultrasound imaging can be used to locate electrode(s) within a hollow organ or body lumen during the magnetically controlled electrode movement to confirm the electrode movement visually, e.g., by display of gathered ultrasound images. FIG. 81 illustrates one embodiment of an ultrasound imaging device 1870 visualizing through a tissue wall 1872, such as an abdominal wall for visualizing a duodenum or other portion of an intestine.

In some embodiments, location monitoring and control can include controlling ablation device rotation. Controlling rotation of an ablation device may help control cauterization exposure and/or may help ensure complete ablation of an internal surface of a hollow organ or body lumen around a circumference thereof. When a portion of the internal surface is determined to be ablated, such as by temperature monitoring, the ablation device can be rotated so an electrode that was ablating the now-completed area of tissue can now deliver energy to another area along the internal surface of the tissue. A rate and/or amount of the rotation can be controlled by adjusting at least one variable parameter of a control algorithm. The ablation device's rotation can be controlled via rotation of the ablation device, via rotation of a scope in which the ablation device is positioned (such as in a working channel thereof) so as to rotate the ablation device with the scope, or via rotation of an overtube in which the ablation device is positioned (such as in an inner lumen thereof) so as to rotate the ablation device with the overtube. An ablation device can also be translated longitudinally, as discussed herein, to help ensure that all target tissue is ablated.

Devices and systems disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It can be preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 issued Feb. 14, 2012 and entitled "System And Method Of Sterilizing An Implantable Medical Device." It is preferred that device, if implanted, is hermetically sealed. This can be done by any number of ways known to those skilled in the art.

The present disclosure has been described above by way of example only within the context of the overall disclosure provided herein. It will be appreciated that modifications within the spirit and scope of the claims may be made without departing from the overall scope of the present disclosure. All publications and references cited herein are expressly incorporated herein by reference in their entirety for all purposes.

What is claimed is:

1. A surgical system, comprising:
a controller configured to at least:
receive, from an imaging device located in a first anatomic space of a patient, images associated with a tissue of the patient, wherein the tissue is in a second anatomic space of the patient,
based on the received images from the imaging device located in the first anatomic space, determine a location and an orientation of each electrode of a plurality of electrodes of a surgical device, wherein the surgical device is located in the second anatomic space of the patient,
for each electrode of the plurality of electrodes, determine a property of the tissue at the location and orientation of the respective electrode using the received images,
for each electrode of the plurality of electrodes, associate the property of the tissue determined at the location and orientation of the respective electrode with that electrode,
for each electrode of the plurality of electrodes, automatically adjust at least one parameter associated with the respective electrode based on the property of the tissue associated with that electrode, wherein the at least one parameter associated with the respective electrode is adjusted independently, and
send the at least one parameter to the surgical device.

2. The surgical system of claim 1, wherein, based on the received images, the controller being configured to automatically adjust the at least one parameter associated with the respective electrode comprises the controller being configured to automatically adjust the at least one parameter to prevent the property of the tissue associated with that electrode from exceeding a threshold value.

3. The surgical system of claim 1, wherein the controller being configured to automatically adjust the at least one parameter associated with the respective electrode comprises the controller being configured to automatically adjust longitudinal and multi-axial movement of that electrode.

4. The surgical system of claim 1, wherein the tissue is a mucosal tissue that is longitudinally and circumferentially irregular, and wherein, based on the received images, the controller is configured to confirm full thickness and full circumferential mucosal ablation of the tissue.

5. The surgical system of claim 1, wherein the controller is configured to activate a subset of the plurality of electrodes and deactivate remaining electrodes of the plurality of electrodes of the surgical device.

6. The surgical system of claim 1, wherein the received images comprise infrared images indicating a thermal effect of the tissue, and wherein the controller being configured to automatically adjust the at least one parameter associated with the respective electrode comprises the controller being configured to automatically adjust a retraction rate of the respective electrode based on the thermal effect.

7. The surgical system of claim 1, wherein the surgical device comprises an expandable balloon, wherein the plurality of electrodes are printed on an exterior of the expandable balloon, and wherein the controller being configured to automatically adjust the at least one parameter of associated with the respective electrode comprises the controller being configured to automatically adjust expansion of the expandable balloon.

8. The surgical system of claim 1, wherein the surgical device comprises an ablation device, wherein the plurality of electrodes are attached to an expandable basket of the ablation device, and wherein the controller being configured to automatically adjust the at least one parameter of the respective electrode comprises the controller being configured to automatically adjust expansion of the expandable basket.

9. The surgical system of claim 1, wherein the surgical device comprises a magnet, wherein the surgical system further comprises a magnetic element configured to be positioned in the first anatomic space, and wherein the controller is configured to determine a thickness of the tissue based on a magnetic attraction between the magnet and the magnetic element.

10. The surgical system of claim 1, wherein the controller being configured to automatically adjust the at least one parameter of the respective electrode comprises the controller being configured to automatically adjust radial rotation of the respective electrode.

11. The surgical system of claim 1, wherein a surgical hub comprises the controller.

12. A surgical method comprising:

advancing a first distal portion of an imaging device into a first anatomic space of a patient and a second distal portion of a surgical device comprising a plurality of electrodes into a second anatomic space of the patient;

delivering energy to a tissue of the patient using at least one of the plurality of electrodes of the surgical device located in the second anatomic space of the patient;

receiving images from the imaging device located in the first anatomic space;

based on the received images from the imaging device located in the first anatomic space, determining a location and an orientation of each electrode of the plurality of electrodes of the surgical device located in the second anatomic space of the patient;

for each electrode of the plurality of electrodes, determining a property associated with the tissue at the location and orientation of that electrode using the received images from the imaging device located in the first anatomic space;

for each electrode of the plurality of electrodes, associating the property of the tissue determined at the location and orientation of the electrode with that electrode;

for each electrode of the plurality of electrodes, automatically adjusting at least one parameter associated with the respective electrode based on the property of the tissue associated with that electrode, wherein the at least one parameter associated with the respective electrode is adjusted independently; and sending the at least one parameter to the surgical device.

13. The surgical method of claim 12, further comprising, based on the received images, automatically adjusting the at least one parameter to prevent the property of the tissue from exceeding a threshold value.

14. The surgical method of claim 12, further comprising automatically adjusting longitudinal and multi-axial movement of the respective electrode.

15. The surgical method of claim 12, wherein the tissue is a mucosal tissue that is longitudinally and circumferentially irregular, and further comprising confirming full thickness and full circumferential mucosal ablation of the tissue.

16. The surgical method of claim 12, wherein the received images comprise infrared images indicating a thermal effect of the tissue, and wherein automatically adjusting the at least one parameter comprises automatically adjusting a retraction rate of the respective electrode based on the thermal effect.

17. The surgical method of claim 12, wherein the surgical device comprises an expandable balloon, wherein the plurality of electrodes are printed on an exterior of the expandable balloon, and wherein automatically adjusting the at least one parameter of the respective electrode comprises automatically adjusting expansion of the expandable balloon.

18. The surgical method of claim 12, wherein the surgical device comprises an ablation device, wherein the plurality of electrodes are attached to an expandable basket of the ablation device, and wherein automatically adjusting the at least one parameter of the respective electrode of comprises automatically adjusting expansion of the expandable basket of the ablation device.

19. The surgical method of claim 12, wherein the surgical device comprises a magnet, wherein a magnetic element is positioned in the first anatomic space, and wherein the surgical method further comprises determining a thickness of the tissue based on a magnetic attraction between the magnet and the magnetic element.

20. The surgical method of claim 12, wherein automatically adjusting the at least one parameter of the respective electrode comprises automatically controlling radial rotation of the respective electrode.

* * * * *